United States Patent [19]

Farge et al.

[11] Patent Number: 4,496,560
[45] Date of Patent: Jan. 29, 1985

[54] CEPHALOSPORIN DERIVATIVES, AND PHARMACEUTICAL COMPOSITIONS CONTAINING THEM

[75] Inventors: Daniel Farge; Pierre Le Roy, both of Thiais; Claude Moutonnier, Le Plessis Robinson; Jean-Francois Peyronel, Palaiseau; Bernard Plau, Creteil, all of France

[73] Assignee: Rhone-Poulenc Sante, Courbevoie, France

[21] Appl. No.: 408,676

[22] Filed: Aug. 16, 1982

[30] Foreign Application Priority Data

Aug. 17, 1981 [FR] France .................. 81 15804

[51] Int. Cl.³ .................. C07D 501/24; A61K 31/545
[52] U.S. Cl. ..................... 514/204; 544/26; 544/27; 544/21; 514/206
[58] Field of Search ............. 544/26, 25, 27; 424/246, 248.4

[56] References Cited

U.S. PATENT DOCUMENTS 3,962,223 6/1976 Martel et al. .
4,060,687 11/1977 Christensen et al. .................. 544/27
4,182,866 1/1980 Miki et al. ..................... 544/27

FOREIGN PATENT DOCUMENTS 2206085 6/1974 France .

*Primary Examiner*—Nicholas S. Rizzo
*Attorney, Agent, or Firm*—Stevens, Davis, Miller & Mosher

[57] ABSTRACT

New cephalosporin derivatives, of the formula:

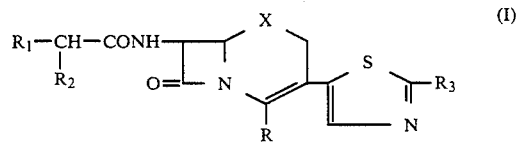

in which $R_1$ is a heterocyclic, phenyl, p-hydroxyphenyl, phenoxy or dichlorophenylthio radical and $R_2$ is a hydrogen atom, or $R_1$ is phenyl or p-hydroxyphenyl and $R_2$ is an amino radical, $R_3$ is hydrogen, phenyl, substituted phenyl, alkylthio or substituted amino or a radical of the structure $-A-R'_3$, which A is $-CH_2-$, $-NH-$ or $-NHCO-$ and $R'_3$ is a substituted pyridinio radical, R is a carboxyl radical or a carboxylato radical if $R_3$ is a $-AR'_3$ radical and X is a sulphur or oxygen atom, the said alkyl moieties or radicals containing 1 to 4 carbon atoms each in their D, L and D,L forms, where these exist, and their salts are narrow-spectrum anti-bacterial agents which are active against gram-positive bacteria.

9 Claims, No Drawings

CEPHALOSPORIN DERIVATIVES, AND PHARMACEUTICAL COMPOSITIONS CONTAINING THEM

The present invention relates to cephalosporin derivatives, their salts, their preparation and pharmaceutical compositions which contain them.

Belgian Pat. No. 793,448 has described 3-heterocyclyl-cephalosporins which are active against gram-positive germs, and the preparation of these compounds.

French patent application No. 2,206,085 describes, inter alia, heterocyclylcephalosporins defined by a very wide general formula (and, in particular, 3-thiazolyl-cephalosporins), which are prepared by total synthesis and which are active against gram-positive germs and gram-negative germs.

The publication by T. Sugawara et al, Chem. Pharm. Bull. 28 (7), 2116 (1980), refers to thiadiazolyl-cephalosporins whose principal value is that they have a good activity against gram-negative germs.

It has now been found that a particular class of 3-thiazolyl-cephalosporins here represented by the general formula (I) exhibits antibacterial activity specifically against gram-positive germs, whilst its activity against gram-negative germs is virtually nonexistent. Moreover, this novel class of 3-thiazolyl-cephalosporins has the advantage that it is easy to synthesize.

The new cephalosporins have the formula:

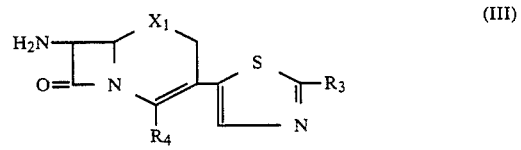

in which $R_1$ represents a heterocyclyl radical chosen from thienyl, furyl or 1,3-dithiol-2-on-4-yl or a phenyl, p-hydroxyphenyl, phenoxy or dichlorophenylthio radical and the symbol $R_2$ represents a hydrogen atom, or the symbol $R_1$ represents a phenyl or p-hydroxyphenyl radical and the symbol $R_2$ represents an amino radical; the symbol $R_3$ represents a hydrogen atom, a phenyl radical (optionally substituted by an acylamino radical), an alkylthio, alkylamino, dialkylamino or anilino radical, or $R_3$ represents an acylamino, benzoylamino or thenoylamino radical, optionally substituted on the nitrogen atom by an alkyl or phenyl radical, an alkoxycarbonylamino, dialkylaminoethylamino, dialkylaminomethyleneamino or alkylidenehydrazo radical, an acetamido radical substituted by an amino, 2-aminoethylthio or L-2-amino-2-carboxy-ethylthio radical, or a radical of the formula $-A-R'_3$, in which A represents a bivalent radical chosen from $-CH_2-$, $-NH-$ or $-NH-CO-$ and $R'_3$ represents a 1-methyl-3- (or -14-) pyridinio, 1-benzoylmethyl-3- (or -4-) pyridinio, or 1-carboxymethyl-3- (or -4-) pyridinio radical, the symbol R represents a carboxyl radical or represents a carboxylato radical if $R'_3$ is a substituted pyridinio radical, and the symbol X represents an atom of sulphur or of oxygen.

It is to be understood that the alkyl and acyl radicals and moieties mentioned above are straight or branched and contain 1 to 4 carbon atoms each.

It is also to be understood that if $R_2$ is an amino radical, the D and L forms of the products of the general formula (I) and their mixtures fall within the scope of the present invention.

A. According to the invention, the products of the general formula (I) can be prepared by the action of an acid of the general formula

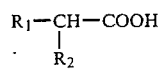

(in which $R_1$ $R_2$ are defined as above, and in which the amine function which $R_2$ may represent is protected beforehand), or of a reactive derivative of this acid, on a 7-amino-cephalosporin derivative of the general formula

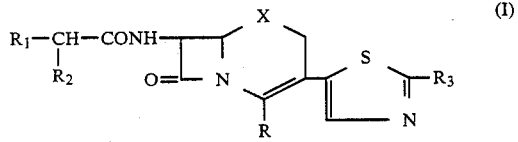

[in which $R_3$, which is defined as above, is protected if it contains an amino radical, $R_4$ is a carboxyl radical which is free or protected by an easily removable group (for example methoxymethyl, t.-butyl, 2,2,2-trichloroethyl, benzhydryl, p-nitrobenzyl or p-methoxybenzyl) or a carboxylato radical, and $X_1$ is defined like X above, or represents a sulphinyl group], after which, where necessary, the sulphoxide is reduced and, where appropriate, the protecting radicals are removed.

The amine function represented by $R_2$ (and, where necessary, the amine function contained in $R_3$) can be protected by any easily removable group which is used in peptide chemistry and whose introduction and removal do not affect the remainder of the molecule.

It is in particular possible to use groups such as t.-butoxycarbonyl, vinyloxycarbonyl, 2,2,2-trichloroethoxycarbonyl, chloroacetyl, trichloroacetyl, trifluoroacetyl, trityl, benzyl, benzyloxycarbonyl, p-nitrobenzyloxycarbonyl, p-methoxybenzyloxycarbonyl or formyl, or a diphenylphosphinoyl radical or a radical as defined below by the general formula (XVI), which radicals can be introduced by applying the method described by A. MORIMOTO et al., J. Chem. Soc. Perkin I, 1109 (1980).

If $R_1$ contains a hydroxyl radical, this group can be free or protected. Protection is effected, for example, by trityl, tetrahydropyranyl, alkoxycarbonyl (for example t.-butoxycarbonyl), aryloxycarbonyl (for example benzyloxycarbonyl) or p-methoxybenzyl radicals.

If the product of the general formula (II) is used in its acid form, the condensation onto the 7-amino-cephalosporin of the general formula (III), in which $R_4$ is a protected carboxyl radical, or a carboxylato radical, is effected in the presence of a condensing agent such as a carbodiimide (for example dicyclohexylcarbodiimide), N,N'-carbonyldiimidazole or 2-ethoxy-1-ethoxycarbonyl-1,2-dihydro-quinoline, at a temperature of between $-20°$ and $40°$ C., after which, where necessary, the protective groups are removed.

If it is desired to utilize a reactive derivative of the acid of the general formula (II), it is possible to employ the anhydride, a mixed anhydride, or a reactive ester of the general formula $$R_1\text{—}CH\text{—}COOZ \qquad (IV)$$
$$\underset{R_2}{|}$$

in which $R_1$ and $R_2$ are defined as above, Z represents a succinimido, benzotriazol-1-yl, 4-nitrophenyl, 2,4-dinitrophenyl, pentachlorophenyl or phthalimido radical, it being understood that if $R_2$ is an amino radical, the amine function of all these derivatives is protected beforehand.

It is also advantageous to use an acid halide. In this latter case, if $R_2$ is amino, it is possible to carry out the reaction with the hydrochloride of the acid chloride, which in this particular case avoids prior protection of the amino radical.

If the anhydride, a mixed anhydride or an acid halide (which can be prepared in situ) are employed, the condensation is carried out in an inert organic solvent such as an ether (for example tetrahydrofuran or dioxane), a chlorinated solvent (for example chloroform or methylene chloride), an amide (for example dimethylformamide or dimethylacetamide) or a ketone (for example acetone), or in mixtures of the above solvents, in the presence of an acid acceptor such as an epoxide (for example propylene oxide) or such as a nitrogen-containing organic base such as pyridine, dimethylaminopyridine, N-methylmorpholine or a trialkylamine (for example triethylamine) or in the presence of a silylation agent such as bistrimethylsilylacetamide, or in an aqueous organic medium in the presence of an alkaline condensing agent such as sodium bicarbonate, and the reaction is carried out at a temperature of between $-40°$ and $40°$ C., after which the protecting groups are replaced by hydrogen atoms.

If a reactive ester of the general formula (IV) is employed, the reaction is generally carried out in the presence of a tertiary amine (for example triethylamine) in an organic solvent such as dimethylformamide, at a temperature of between $0°$ and $40°$ C., after which the protecting groups are replaced by hydrogen atoms.

Where necessary, the reduction of the sulphoxide is carried out under the conditions described in German patent application No. 2,637,176.

The removal of the protecting groups of an acid may be effected, for example:

in the case of a t.-butyl, p-methoxybenzyl or benzhydryl group, by treatment in an acid medium under the conditions below for the removal of the trityl protecting radical from amino. In the case of the benzhydryl radical, the removal any be carried out in the presence of anisole or by treatment with aluminium chloride under the conditions described by T. Tsuji et al., Tet.-Lett., 30, 2793 (1979);

in the case of a methoxymethyl group, by treatment in a dilute acid medium; and in the case of a 2,2,2-trichloroethyl or p-nitrobenzyl group, by reduction (especially by treatment with zinc in acetic acid or, in the case of a p-nitrobenzyl group, by hydrogenolysis).

The removal of the protecting groups from an amine may be effected, for example:

in the case of a t.-butoxycarbonyl, vinyloxycarbonyl, trityl, p-methoxybenzyloxycarbonyl or formyl radical, by treatment in an acid medium. Preferably, trifluoroacetic acid is used and the process is carried out at a temperature of between $0°$ and $20°$ C., or anhydrous or aqueous formic, phosphoric or polyphosphoric acid is used at a temperature of between $20°$ and $60°$ C., or para-toluenesulphonic or methanesulphonic acid is used in acetone or acetonitrile at a temperature of between $20°$ C. and the reflux temperature of the reaction mixture. Under these conditions, the product of the general formula (I) can be obtained in the form of a trifluoroacetate, a solvate with formic acid, a phosphate, a methanesulphonate or a para-toluenesulphonate, in which the amine function can be liberated by any method known per se for obtaining an amine from one of its salts without affecting the remainder of the molecule. In particular, the process is effected by bringing the compound into contact with an ion exchange resin, or by the action of an organic base;

in the case of a 2,2,2-trichloroethoxycarbonyl or p-nitrobenzyloxycarbonyl radical or of a radical of the general formula (XVI), in which R' is 2,2,2-trichloroethyl or nitrobenzyl, by reduction (especially by treatment with zinc in acetic acid);

in the case of a chloroacetyl or trichloroacetyl radical, by applying the method described in the French patent published under No. 2,243,199;

in the case of a benzyl or benzyloxycarbonyl radical, by catalytic hydrogenation;

in the case of a trifluoroacetyl radical, by treatment in a basic medium;

in the case of a diphenylphosphinoyl radical, according to the method described by P. Haake et al., J. Am. Chem. Soc., 95, 8073 (1973); and in the case of a radical of the general formula (XVI), according to the method described in Belgian Pat. No. 833,619.

The removal of the protecting groups from a hydroxyl radical is effected, where necessary: in the case of trityl, tetrahydropyranyl or methoxybenzyl groups, by acidolysis, for example by means of trifluoroacetic acid, aqueous or non-aqueous formic acid or para-toluenesulphonic acid;

in the case of alkoxycarbonyl or aryloxycarbonyl groups, according to the methods described in Belgian Pat. No. 871,213.

B. According to the invention, the cephalosporin derivatives of the general formula (I), in which $R_1$, $R_2$ and X are defined as above, $R_3$ is defined as above except for representing a $-A-R'_3$ radical and R is a carboxyl radical, can also be prepared by the action of a product of the general formula $$R_3CSNH_2 \qquad (V)$$

in which $R_3$ is defined as above (it being understood that if it contains an amino radical, the latter is protected) on a cephalosporin derivative of the general formula

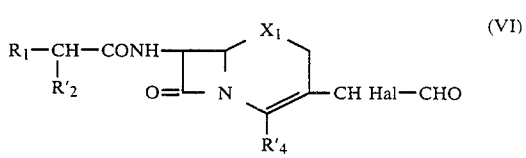

(VI)

(in which $R_1$ and $X_1$ are defined as above, $R'_2$ represents a hydrogen atom or a protected amino radical, $R'_4$ represents a protected carboxyl radical as defined for $R_4$ and Hal represents a halogen atom), followed, where appropriate, by the action of a dehydrating agent and followed, where necessary, by reduction of the sulphoxide and removal of the protective groups.

If R'$_2$ represents a protected amino radical, it can be protected by, for example, a t.-butoxycarbonyl, 2,2,2-trichloro-ethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl radical or by a radical of the general formula (XVI), as defined below.

The symbol Hal can represent a chlorine, bromine or iodine atom.

If R$_1$ contains a hydroxyl radical, the latter can be free or protected. Protection and unblocking are effected under the conditions described above.

The reaction is generally carried out in an organic or aqueous-organic medium, for example in solvents (or mixtures of solvents) such as alcohols (methanol or ethanol), ethers (tetrahydrofuran or dioxane), ketones (acetone), nitriles (acetonitrile), secondary amines (dimethylformamide or dimethylacetamide), esters (ethyl acetate) or acids (acetic acid or formic acid), in the presence or absence of a base (sodium hydroxide, potassium hydroxide, carbonates and bicarbonates of alkali metals, carboxylic acid salts of alkali metals, or tertiary amines), at a temperature of between −50° C. and the reflux temperature of the reaction mixture.

It is sometimes preferable to introduce a dehydrating agent. This is the case, in particular, if R$_3$ represents a phenyl or substituted phenyl radical.

Amongst the dehydrating agents which may be used there may be mentioned the halides of sulphonic acids (for example tosyl chloride, methanesulphonyl chloride or a halide of the type RSO$_2$Cl, in which R is alkyl, trifluoromethyl(or trichloromethyl) or phenyl, optionally substituted by halogen, methyl or nitro), the phosphoryl halides (for example phosphorus oxychloride), or sulphonyl chloride, in a basic solvent [pyridine or an amide (for example dimethylformamide, dimethylacetamide or hexamethylphosphorotriamide)], or in a chlorinated solvent (for example chloroform or methylene chloride), an ether (for example tetrahydrofuran), an ester, a ketone, a nitrile or an aromatic solvent, in the presence of a tertiary amine (for example pyridine, quinoline or triethylamine).

C. According to the invention, the products of the general formula (I) in which R$_3$ represents an acylamino, benzoylamino or thenoylamino radical, optionally substituted at the nitrogen atom, or represents an alkoxycarbonylamino or dialkylaminomethyleneamino radical, a substituted acetamido radical or a radical of the structure —A—R'$_3$, in which A is —NHCO— and R'$_3$ is defined as above, can be obtained from the corresponding amine of the general formula

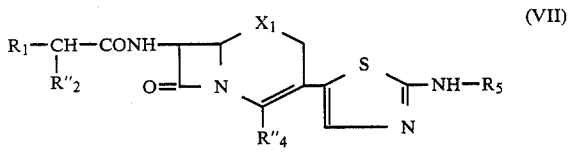

(VII)

in which R$_1$ and X$_1$ are defined as above, R''$_2$ represents a protected amino radical, R''$_4$ is a carboxyl or protected carboxyl radical as defined for R'$_4$ and R$_5$ is a hydrogen atom or an alkyl or phenyl radical, by any method known per se for forming an amide, carbamate or amidine function without affecting the remainder of the molecule, followed, where necessary, by reduction of the sulphoxide obtained, and, where appropriate, by removal of the protecting radicals.

The radical R''$_2$ protecting the amino can be chosen from amongst the groups mentioned above for process A. The radical can be removed, after the reaction, in accordance with the methods mentioned above in A.

If R$_1$ contains a hydroxyl radical, the latter can be free or, preferably, protected. Protection, and removal of the protecting radicals, are carried out as described above.

If it is desired to prepare a product of the general formula (I) in which R$_3$ represents an acylamino, benzoylamino or thenoylamino radical (which radicals may or may not be substituted), an alkoxycarbonylamino radical, a substituted acetamido radical or a radical of the structure —A—R'$_3$, in which A is —NHCO—, the reaction is advantageously carried out by the action of the corresponding acid chloride, anhydride or chloroformate, under the conditions described above for the reaction of the acid chloride of the general formula (II), on the 7-amino-cephalosporin derivative of the general formula (III). It is to be understood that the radicals of primary amines which may be present in the radical R$_3$ are protected beforehand.

If it is desired to prepare a product of the general formula (I) in which R$_3$ is dialkylaminomethyleneamino, the reaction is advantageously carried out by the action of the acetal of the corresponding dialkylformamide on the cephalosporin derivative of the general formula (VII), in which R''$_4$ represents a protected carboxyl radical and R$_5$ represents a hydrogen atom.

D. According to the invention, the products of the general formula (I) in which R$_1$, R$_2$ and X are defined as above, R$_3$ is a radical of the structure —AR'$_3$ and R is a carboxylato radical can be obtained by the action of a methyl halide, benzoylmethyl halide or carboxymethyl halide (in which the acid function is free or protected) on a cephalosporin derivative of the general formula

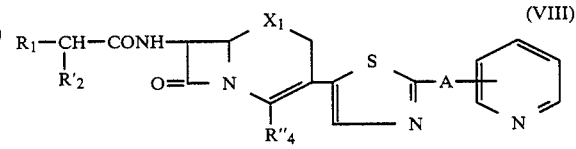

(VIII)

in which the radical A is substituted in the 3- or 4-position of the pyridyl ring, R$_1$, R''$_4$, X$_1$ and A are defined as above and R'$_2$ is defined as for the general formula (VII), followed, where necessary, by reduction of the sulphoxide obtained and removal of the protecting radicals.

The reaction is generally carried out in an organic solvent such as an amide (for example dimethylformamide, hexamethylphosphorotriamide or dimethylacetamide), a nitrile (for example acetonitrile), a ketone (for example acetone) or a nitro derivative (for example nitromethane or nitrobenzene), or in a mixture of such solvents, at a temperature of between 0° and 80° C.

The protected radicals are liberated under the conditions described above.

E. According to the invention, the products of the general formula (I), in which R$_1$, R$_2$ and X are defined as above, R$_3$ represents an acetamido radical substituted by a 2-amino-ethylthio radical or L-2-amino-2-carboxyethylthio radical and R represents a carboxyl radical can also be obtained by the action of cysteamine or cysteine, whose amine function, and where relevent, acid function have beforehand been protected, on a halogenoacetamidothiazolylcephalosporin of the general formula

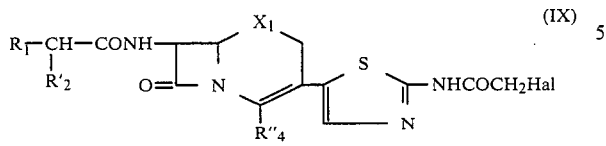 (IX)

[in which R₁, R″₄ and X₁ are defined as above, R′₂ is defined as for the general formula (VII) and Hal represents a chlorine, bromine or iodine atom], after which, where necessary, the sulphoxide obtained is reduced and the protecting radicals are removed.

The reaction is generally carried out in an organic solvent, for example and amide (dimethylformamide), a nitrile (acetonitrile) or a mixture of such solvents, at a temperature of between −20° C. and the reflux temperature of the reaction mixture. Preferably, it is carried out in the presence of a tertiary organic base, for example diisopropylethylamine, diethylphenylamine or triethylamine.

It is not absolutely necessary to isolate the intermediate product before proceeding to the reduction.

The removal of the protecting radicals is carried out under the conditions described above.

The 7-amino-cephalosporin derivatives of the general formula (III) can be obtained from a product of the general formula

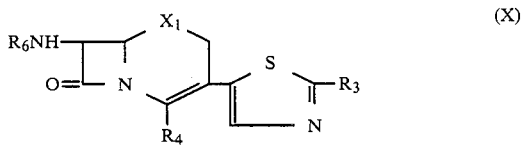 (X)

[in which R₃, R₄ and X₁ are defined as above, it being understood that if R₃ contains an amino radical, the latter is protected, and R₆ represents an easily removable radical], by removal of the radical R₆ or, where necessary, successive or simultaneous removal of the radical R₆ and of the protecting radical contained in R₄, if it is desired to obtain a product of the general formula (III) in which the acid function is free, from a product of the general formula (X) in which the acid function is protected.

By an easily removable radical R₆ there is understood, for example:
(1) benzhydryl or trityl,
(2) an acyl radical of the general formula:

$$R_7CO—$$ (XI)

in which R₇ represents
(a) a hydrogen atom or an alkyl radical containing 1 to 7 carbon atoms or methyl substituted by 1 to 3 halogen atoms,
(b) a phenyl radical (which can be mono-, di- or trisubstituted by halogen atoms or hydroxyl, nitro, cyano, trifluoromethyl, alkyl or alkoxy radicals) or a thien-2-yl or thien-3-yl radical,
(c) a radical of the general formula:

$$R'_7—Y—CH_2—$$ (XIa)

in which R′₇ is a phenyl radical which can be substituted by a halogen atom or by an alkyl, alkoxy or hydroxyl radical, and Y is an oxygen or sulphur atom, or
(d) an arylalkyl radical of the general formula:

$$R''_7CH_2—$$ (XIb)

in which R″₇ is a phenyl radical which can be mono-, di- or tri-substituted by hydroxyl, alkyl or alkoxy radicals, or is a heterocyclyl radical such as thien-2-yl, thien-3-yl, fur-2-yl or fur-3-yl,
(3) a 5-amino-adipoly radical whose amne and acid functions are protected by protective radicals such as those defined above,
(4) a radical of the general formula:

$$R_8OCO—$$ (XII)

in which R₈ is a branched unsubstituted alkyl radical, a straight or branched alkyl radical carrying one or more substituents [such as halogen atoms or cyano, trialkylsilyl, phenyl or substituted phenyl (the substituents being one or more halogen atoms or alkyl, alkoxy, nitro or phenyl radicals) radicals] or a quinolyl radical, or
(5) a radical of the general formula:

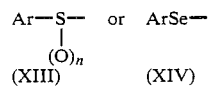

in which the radical Ar is a phenyl radical optionally substituted by one or more halogen atoms or nitro or alkyl radicals and n is 0 or 1;
(6) alternatively, R₆NH— can be replaced by a dialkylaminomethyleneamino radical or by a radical of the general formula:

$$Ar'—CH=N—$$ (XV)

in which Ar′ is a phenyl radical optionally substituted by one or more radicals such as alkyl, alkoxy, hydroxyl or nitro, or
(7) R₆ is a diphenylphosphinoyl radical or a radical of the general formula:

 (XVI)

in which R′ is an alkyl, 2,2,2-trichloroethyl, phenyl or benzyl (the latter two being optionally substituted by a halogen atom or by an alkyl, alkoxy or nitro radical), or the radicals R′ together form an alkylene radical containing 2 or 3 carbon atoms.

Amongst examples of radicals R₆ which can be used, the following may be mentioned: formyl, acetyl, trichloroacetyl, phenylacetyl, phenoxyacetyl, benzoyl, t-butoxycarbonyl, 2-chloro-1,1-dimethyl-ethoxycarbonyl, 2,2,2-trichloroethoxycarbonyl, 2,2,2-trichloro-1,1-dimethylethoxycarbonyl, 2-cyano-1,1-dimethyl-ethoxycarbonyl, 2-trimethylsilyl-ethoxycarbonyl, benzyloxycarbonyl, p-methoxybenzyloxycarbonyl, 3,5-dimethoxy-benzyloxycarbonyl, p-nitrobenzyloxycarbonyl, diphenylmethoxycarbonyl, 2-(biphenyl-4-yl)-isopropoxycarbonyl, quinol-8-yloxycarbonyl, o-nitrophenylthio, p-nitrophenylthio, dimethoxyphosphoryl, diethoxyphosphoryl, diphenoxyphosphoryl and dibenzyloxyphosphoryl.

As examples of methyleneamino radicals defined above in 6), there may be mentioned dimethylaminomethyleneamino, 3,4-dimethoxybenzylideneamino and 4-nitrobenzylideneamino.

It is to be understood that the radical $R_6$ and, where relevant, the amino-protecting radical contained in $R_3$ are different and are so chosen that they can be removed selectively.

The removal of the protecting radical can be effected by any known method for liberating an amine function without affecting the remainder of the molecule.

In particular, the conditions described in Belgian Pat. No. 883,415 and referred to above, under A., can be employed.

The cephalosporin derivatives of the general formula (X) can be obtained, depending on the meaning of the symbol $R_3$, by analogy with one of the processes B, C and D used for the preparation of the products according to the invention, namely:

either by the action of a product of the general formula (V) on a cephalosporin derivative of the general formula:

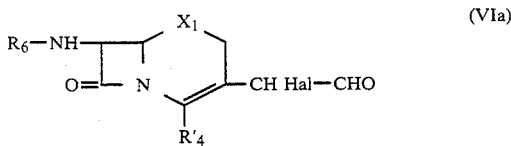

in which $R'_4$, $R_6$, $X_1$ and Hal are defined as above, followed, if appropriate, by the addition of a dehydrating agent and, if appropriate, by liberation of the acid function if it is desired to obtain a product of the general formula (X) in which $R_4$ is a carboxyl radical, or from a product of the general formula:

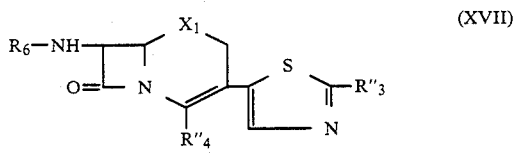

[in which $R''_4$, $R_6$ and $X_1$ are defined as above, and $R''_3$ represents either a radical of the structure $—NHR_5$, in which $R_5$ is defined as above for the general formula (VII), or a radical of the structure

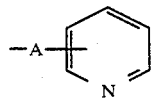

defined as above in the general formula (VIII)], using, depending on the particular case, the conditions described in process C or D.

The conditions of use of these processes are identical to those employed for the preparation of the products of the general formula (I).

The products of the general formula (V) and (Va), described below, can be prepared by the action of ammonia on the corresponding isothiocyanate or dithiocarbamate, or by the action of hydrogen sulphide on the corresponding nitrile, or more precisely according to the methods cited below:

if $R_3$ represents a hydrogen atom: according to the method described by A. W. HOFMANN, Chem. Ber., 11, 340 (1878), if $R_3$ is an acylaminophenyl radical: by applying the method of L. Stephensen et al., J. Chem. Soc. (C), 861 (1969), if $R_3$ represents an alkylthio radical: by the action of ammonium dithiocarbamate on the appropriate alkyl halide, if $R_3$ represents dialkylamino: by applying the method of MAMELI, Ann. Chimica, 46, 545 (1956), if $R_3$ represents acylamino: according to the method described by M. L. MOORE and F. S. CROSSLEY, J. Am. Chem. Soc. 62, 3274 (1940), if $R_3$ or $R''_3$ represent benzoylamino, thenoylamino, nicotinoylamino or isonicotinoylamino: according to the method of W. H. PIKE, Chem. Ber., 6, 755 (1873), if $R_3$ represents acylamino, benzoylamino or thenoylamino substituted on the nitrogen atom by an alkyl radical: by analogy with the method described by KURZER, J. Chem. Soc., 1957, 4461, from N-cyanoacetamides, N-cyanobenzamides or N-cyanothenoylamides obtained respectively by applying the method of R. HUFFMANN and F. C. SCHAEFER, J. Org. Chem. 28, 1816 (1963) or of K. HARTKE and E. PALOU, Chem. Ber., 99 (10) 3155 (1966), if $R_3$ is an acylamino, benzoylamino or thenoylamino radical substituted on the nitrogen atom by a phenyl radical: according to the method described by P. K. SRIVASTAVA, Ind. J. Chem., 7 (4), 323 (1969), if $R_3$ is an alkoxycarbonylamino radical: by applying the method of R. E. DORAN, J. Chem. Soc., 69, 331 (1896), if $R_3$ is a dialkylaminoethylamino radical: according to the method described in German Patent Application No. 2,738,711, if $R_3$ is a dialkylaminomethyleneamino radical: by applying the method described by H. BREDERECK et al., Ber., 97, 61 (1964), and if $R_3$ is alkylidenehydrazo: by the action of thiosemicarbazide on the appropriate ketone or aldehyde.

The cephalosporin derivatives of the general formula (VI) and (VIa) in which $X_1$ is other than the sulphinyl radical can be prepared by the action of a halogenating agent on an enamine of the general formula:

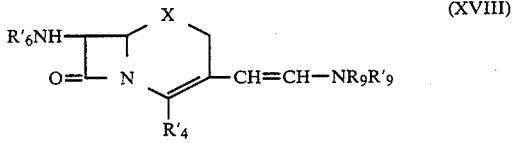

[in which $R'_4$ and X are defined as above, $R'_6$ represents an $R_6$ radical or an $R_1CHR'_2—CO—$ radical (in which $R_1$ and $R'_2$ are defined as above) and $R_9$ and $R'_9$, which may be identical or different, represent alkyl radicals (optionally substituted by an alkoxy or dialkylamino radical) or phenyl radicals, or form, together with the nitrogen atom to which they are attached, a heterocyclic structure with 5 or 6 members, optionally containing another hetero-atom chosen from amongst nitrogen, oxygen or sulphur, and optionally substituted by an alkyl radical], followed by hydrolysis of the product formed.

For example, an enamine of the general formula (XVIII), in which R$_9$ and R$'_9$ each represent a methyl radical, is employed.

Amongst the halogenating agents there may be mentioned the halogens, the N-haloamides [for example N-bromo-(or N-chloro-)succinimide, N-bromo- (or N-chloro-)-acetamide and dibromohydantoin], and the alkyl hypohalites (for example t.-butyl hypochlorite, t.-butyl hypobromite or ethyl hypochlorite).

The reaction is generally carried out in an organic solvent, such as an ether (for example tetrahydrofuran or dioxane), a chlorinated solvent (for example methylene chloride or chloroform), an ester (for example ethyl acetate), an alcohol (for example methanol or ethanol), an amide (for example dimethylformamide or dimethylacetamide), a nitrile (for example acetonitrile) or a ketone (for example acetone), or in a mixture of these solvents, at a temperature of between −70° and 0° C.

The hydrolysis is carried out at a temperature of between −70° and 20° C.

It is not essential to isolate or purify the products of the general formulae (VI) or (VIa) in order to use them in accordance with the invention.

The cephalosporin derivatives of the general formulae (VI) and (VIa), in which X$_1$ is a sulphinyl group can be obtained by oxidising a product of the general formula (VI) or (VIa), in which X$_1$ is a sulphur atom, by applying the methods described in German Patent Application No. 2,637,176.

The enamines of the general formula (XVIII) can be prepared by applying the method described in Belgian Pat. No. 883,416, starting from cephalosporin derivatives of the general formula:

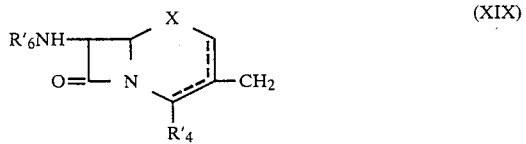

(XIX)

in which R$'_6$, R$'_4$ and X are defined as above.

The cephalosporin derivatives of the general formula (XIX) in which X is a sulphur atom can be obtained as described in Belgian Pat. No. 883,416 or, if R$'_6$ is an easily removable radical, such as defined above for R$_6$ in 7), by applying the method described by A. MORIMOTO et al., J.C.S. Perkin I, 1109 (1980), starting from the corresponding halide R$'_6$-Hal [which can itself be obtained in accordance with one of the methods described by K. SASSE, Methoden den Organischen Chemie, Vol. 12, part 2, page 274, Houben-Weyl, Georg Thieme Verlag, Stuttgart (1964)].

The oxacephalosporins of the general formula (XIX) can be obtained in accordance with the methods described in the literature, for example in Belgian Pat. Nos. 863,998 and 848,288, in U.S. Pat. No. 4,108,992 or by Y. HAMASHIMA et al., Tet. Let. 4943 (1979) and by C. L. BRANCH et al., J. C. S. Perkin I, 2268 (1979), or from oxacephalosporin of the formula

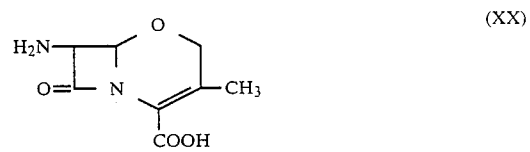

(XX)

by analogy with the methods employed in the chemistry of the cephalosporins, and described, for example, by S. SEKI et al., Tet. Lett., 33, 2915 (1977), R. R. CHAUVETTE et al., J. Org. Chem., 38 (17), 2994 (1973), J. C. SHEEHAN et al., J. Amer. Chem. Soc. 80, 1156 (1958), E. H. FLYNN, Cephalosporins and Penicillins, Acad. Press (1972), L. MORODER et al., Hoppe Seyler's Z. Physiol. Chem. 357 1651 (1976), J. UGI et al., Angew. Chem. Int. Ed. Engl. 17 (5), 361 (1978), L. ZERVAS et al., J. Amer. Chem. Soc. 85, 3660 (1963), J. F. FITT, J. Org. Chem., 42 (15), 2639 (1977), A. MORIMOTO et al., J. Chem. Soc. Perkin I, 1109 (1980), in Belgian Pat. No. 788,885 or in Helv. Chim. Acta., 51, 924 (1968) and also if R$'_6$ represents diphenylmethoxycarbonyl: by the action of the corresponding azidoformate, in an aqueous organic medium, in the presence of an alkali metal bicarbonate, if R$'_6$ represents quinol-8-yloxycarbonyl: by the action of the corresponding carbonate in a basic aqueous organic medium, and if R$'_6$NH— is replaced by 4-nitro-benzylideneamino or 3,4-dimethoxy-benzylideneamino: according to the method described by R. A. FIRESTONE, Tetrahedron Lett., 375 (1972).

The cephalosporin derivatives of the general formulae (VII), (VIII) and (IX) can be prepared by applying the process A described above for the preparation of the products according to the invention, that is to say by acylating a 7-amino-cephalosporin of the general formula

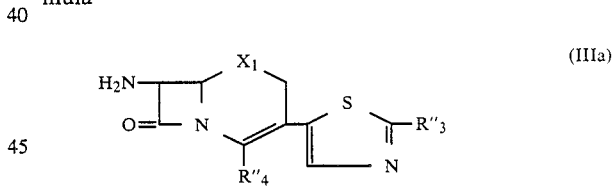

(IIIa)

in which R''$_4$ and X$_1$ are defined as above and R''$_3$ represents a radical of the structure —NHR$_5$, in which R$_5$ is defined as above, a radical of the structure

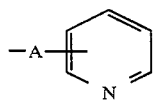

defined as above for the general formula (VIII), or a halogenoacetamido radical as defined for the general formula (IX), followed, where appropriate, by removal of the protecting radicals.

It is to be understood that if R$_5$ represents a hydrogen atom, the —NHR$_5$ radical is preferably protected. Protection is effected by a group as defined above for R'$_2$ in the general formulae (VII), (VIII) and (IX).

Acylation is effected under the conditions described above for the preparation of the products according to the invention by process A.

The removal of the protecting radicals can be effected under the conditions described above.

The 7-amino-cephalosporin of the general formula (IIIa) can be obtained from a cephalosporin of the general formula (XVII) by applying the methods described for the preparation of the 7-amino-cephalosporin of the general formula (III).

It is to be understood that if —NHR$_5$ represents an amino radical, the latter is preferably protected; protection is effected by a group different from R$_6$, in such a way that the protecting radical R$_6$ can be removed selectively.

The cephalosporin of the general formula (XVII), in which R''$_4$, R$_6$ and X$_1$ are defined as above, and R''$_3$ represents a radical having the structure —NHR$_5$ (R$_5$ being defined as above) or the structure

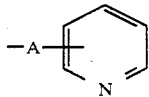

defined as above for the general formula (VIII), can be obtained from a cephalosporin derivative of the general formula (VIa) by analogy with the method described for the preparation of the products according to the invention by process B.

The reaction is effected by the action of a product of the general formula

R''$_3$—CS—NH$_2$ (Va)

in which R''$_3$ is defined as above, using the conditions described above for process B. If appropriate, the protecting group contained in R''$_4$ is removed.

The cephalosporin of the general formula (XVII) in which R''$_3$ is a halogenoacetamido radical can be obtained from a cephalosporin derivative of the general formula (XVII), in which R''$_3$ is a —NHR$_5$ radical, R$_5$ being a hydrogen atom, by the action of a halogenoacetic acid or of one of its derivatives, using the acylation conditions described in process A.

The cephalosporin derivatives of the general formulae (VII) and (VIII) can also be prepared from a cephalosporin of the general formula (VI) by applying process B under the conditions described above.

The cephalosporin derivatives of the general formula (IX) can also be obtained from the corresponding derivative of the general formula (VII), in which R$_5$ is a hydrogen atom, by analogy with the preparation of the products of the general formula (XVII) described above.

The cephalosporin derivatives of the general formula (III), (IIIa), (VI), (VIII), (IX), (X) or (XVII), in which X$_1$ is a sulphinyl radical, can be obtained by oxidising the corresponding derivatives in which X$_1$ is a sulphur atom, under the conditions described in German patent application No. 2,637,176.

The products according to the present invention can be converted to metal salts or to addition salts with nitrogen-containing bases in accordance with methods known per se. These salts can be obtained by the action of a metal base (for example an alkali metal or alkaline earth metal base), of ammonia or of an amine, on a product according to the invention in an appropriate solvent such as an alcohol, an ether or water, or by an exchange reaction with a salt of an organic acid. The salt formed precipitates, where necessary after concentrating its solution, and is separated off by filtration or decanting. It can also be isolated from its solution by evaporation of the solvent, especially by freeze-drying.

The products according to the invention in which R$_2$ is an amino radical or R$_3$ contains an aminosubstituent can also be converted to addition salts with acids; the products according to the invention in which R$_3$ is a —AR'$_3$ radical can be converted to addition salts with strong acids. These addition salts can be obtained by the action of the product on acids in suitable solvents. Organic solvents used are, for example, alcohols, ketones, ethers or chlorinated solvents.

As examples of pharmaceutically acceptable salts there may be mentioned the salts with the alkali metals (sodium, potassium or lithium) or with the alkaline earth metals (magnesium or calcium), the ammonium salts, the salts with nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, N-methylglucamine, diphenylenediamine, benzhydrylamine, quinine, choline, arginine, lysine, leucine or dibenzylamine) or the addition salts with inorganic acids (hydrochlorides, hydrobromides, sulphates, nitrates and phosphates) or organic acids (succinates, fumarates, maleates and p-toluenesulphonates).

The novel products according to the present invention can optionally be purified by physical methods, such as crystallisation, ultrafiltration or chromatography.

The family of cephalosporins according to the present invention, and their pharmaceutically acceptable salts, are particularly valuable narrow-spectrum antibacterial agents, which exhibit a remarkable activity in vitro and in vivo, against gram-positive germs, especially staphylococci and especially against D-streptococci.

To have provided a family of narrow-spectrum products is particularly noteworthy because of the known interest of specialists in such products.

In vitro, the products of the general formula (I) have proved active at a concentration of between 0.03 and 8 μg/cm$^3$ against strains of staphylococci which are sensitive to penicillin G (Staphylococcus aureus Smith), at a concentration of between 0.00006 and 0.03 μg/cm$^3$ against Streptococcus pyogenes Dig 7 and Streptococcus pneumoniae TIL, and especially at concentrations of between 4 and 60 μg/cm$^3$ against Streptococcus faecium ATCC 9790.

In vivo, the products of the general formula (I) have proved active against experimental infections of mice with Staphylococcus aureus Smith, when administered subcutaneously at a dose of between 0.01 and 5 mg/kg per day.

Moreover, the LD$_{50}$ of the products of the general formula (I) is betweem 0.5 g/kg and doses greater than 2.5 g/kg, in the case of subcutaneous administration to mice.

Amongst the products according to the invention, a sub-class of valuable products can be defined by the general formula (I), in which the symbols R$_1$ and R$_2$ are defined as above, and the symbol R$_3$ represents a phenyl, an acylaminophenyl, alkylthio or anilino radical, a benzoylamino or thenoylamino radical optionally substituted on the nitrogen atom (by an alkyl or phenyl radical), an acylamino radical substituted on the nitrogen atom (by an alkyl or phenyl radical), an alkoxycarbonylamino, dialkylaminoethylamino, dialkylaminomethyleneamino or alkylidenehydrazo radical, an acetamido radical substituted by an amino, 2-aminoethylthio or L-2-amino-2-carboxy-ethylthio radical, or a radical of the structure —AR$'_3$, in which A represents a bivalent radical chosen from amongst —CH$_2$—, —NH— or —NHCO— and R$'_3$ represents a 1-methyl-3- (or -4-)pyridinio, 1-benzoylmethyl-3- (or -4-)pyridinio, or 1-carboxymethyl-3- (or -4-)pyridinio radical, or R$_1$ is a 1,3-dithiol-2-on-1-yl radical, R$_2$ is a hydrogen atom and R$_3$ is a hydrogen atom or an alkylamino, dialkylamino or acylamino radical, and the symbols R and X are defined as above.

Further products of particular value are those of the general formula (I) in which R$_1$ represents a thienyl, furyl, phenyl, p-hydroxyphenyl, phenoxy or 3,4-dichlorophenylthio radical and R$_2$ represents a hydrogen atom, or R$_1$ represents a phenyl or p-hydroxyphenyl radical and R$_2$ represents an amino radical, and R$_3$ represents a hydrogen atom or alkylamino, dialkylamino or acylamino radical, X is defined as above and R is a carboxyl radical.

Moreover, amongst the products defined by the general formula (I), more especially valuable products are those in which the symbol R$_1$ is a thienyl radical and the symbol R$_2$ is a hydrogen atom, or the symbol R$_1$ is a phenyl or p-hydroxyphenyl radical and the symbol R$_2$ is an amino radical, the symbol R$_3$ represents a hydrogen atom, a phenyl radical, an acylamino radical which is optionally substituted at the nitrogen atom by an alkyl radical, a dialkylaminoethylamino radical, a 2-aminoethylthioacetamido radical, a L-2-amino-2-carboxyethylthioacetamido radical, or a radical of the structure —AR$'_3$ as defined above, and the symbols R and X are defined as above.

The examples which follow and are given without implying a limitation illustrate the present invention.

EXAMPLE 1

A solution of (thien-2-yl)-acetyl chloride (0.55 cc) in dry tetrahydrofuran (5 cc) is added, in 5 minutes, to a solution of 3-(2-acetamido-thiazol-5-yl)-7-amino-2-benzhydryloxycarbonyl-8-oxo-5-thia-1-azabicyclo[4.2.0]oct-2-ene (2.27 g) in dry tetrahydrofuran (27.5 cc) at 2° C., and after 30 minutes a solution of triethylamine (0.63 cc) in dry tetrahydrofuran (5 cc) is added. After 1 hour's reaction at 2° C., the reaction mixture is filtered and the filtrate is diluted with a mixture of ethyl acetate (200 cc) and half-saturated sodium bicarbonate solution (200 cc). The organic layer is washed with water (100 cc) followed by a saturated sodium chloride solution (100 cc), dried over magnesium sulphate and concentrated to dryness under reduced pressure (30 mm Hg; 4 kPa) at 40° C. The residue is chromatographed on a column (height: 30 cm; diameter: 5 cm) of silica (0.04–0.06 mm), elution being effected under 0.4 bar (40 kPa) with a 30:70 (by volume) mixture of cyclohexane and ethyl acetate, and 50 cc fractions being collected. Fractions 15 to 22, containing the pure product, are combined and concentrated under reduced pressure (30 mm Hg; 4 kPa) at 40° C. 3-(2-Acetamido-thiazol-5-yl)-2-benzhydryloxycarbonyl-8-oxo-7-(thien-2-yl-acetamido)-5-thia-1-azabicyclo[4.2.0]oct-2-ene (0.92 g) is obtained in the form of a yellow powder.

Infra-red spectrum (KBr): characteristic bands (cm$^{-1}$) at 3280, 3200, 2500, 1785, 1770, 1725, 1695, 1670, 1650, 1550, 1530, 1495, 1450, 1220 and 690.

Proton nuclear magnetic resonance spectrum (350 MHz, CDCl$_3$, δ in ppm, J in Hz): 2.09 (s, 3H, CH$_3$CO—); 3.47 (limiting AB system, 2H, —SCH$_2$—); 3.84 (s, 2H, ArCH$_2$CO—); 5.04 (d, J=4.5, 1H, H in the 6-position); 5.88 (dd, J=4.5 and 9, 1H, H in the 7-position); 6.83 (s, 1H, —OCHAr$_2$); 6.9 to 7.0 (m, 2H, H in the 3- and 4-position of the thiophene); 7.13 (s, 1H, H in the 4-position of the thiazole); 7.10 to 7.45 (m, 16H, aromatic protons, H in the 5-position of the thiophene and CONH—C$_7$).

A solution of 3-(2-acetamido-thiazol-5-yl)-2-benzhydryloxycarbonyl-8-oxo-7-(thien-2-yl-acetamido)-5-thia-1-azabicyclo[4.2.0]oct-2-ene (0.85 g) in formic acid (20 cc) is stirred for 30 minutes at 50° C. and then concentrated to dryness under reduced pressure (10 mm Hg; 1.3 kPa). The residue is taken up in ethanol (50 cc), the mixture is stirred for 5 minutes at 50° C. and the solvent is then evaporated to dryness under reduced pressure (30 mm Hg; 4 kPa) at 40° C. The residue is taken up in ethanol (100 cc); the mixture is stirred for 10 minutes at 50° C. and the solid is then filtered off and washed with ethanol (3×15 cc) and ethyl ether (3×10 cc). After drying, 3-(2-acetamidothiazol-5-yl)-2-carboxy-8-oxo-7-(thien-2-yl-acetamido)-5-thia-1-azabicyclo[4.2.0]oct-2-ene (0.53 g) is obtained in the form of a pale yellow powder.

Infra-red spectrum (KBr): characteristic bands (cm$^{-1}$) at 3260, 3200, 3100 to 2200, 1780, 1685, 1650, 1545, 1370 and 700.

Proton nuclear magnetic resonance spectrum (350 MHz, d$_6$-DMSO, δ in ppm, J in Hz): 2.15 (s, 3H, —CO—CH$_3$); 3.74 and 3.80 (2d, J=14, 2H, —CO—CH$_2$—); 3.76 and 3.88 (2d, J=18, 2H, —CH$_2$—S—); 5.16 (d, J=5, 1H, —H in the 6-position); 5.72 (dd, J=5 and 9, 1H, —H in the 7-position); 6.90 to 7 (m, 2H, =CH—CH= thiophene); 7.35 (dd, J=4 and 1, 1H, =CH—S— thiophene); 7.50 (s, 1H, —H of the thiazole); 9.16 (d, J=9, 1H, —CO—NH—); 13.13 (s broad, 1H, —NH—CO—CH$_3$).

The sodium salt of 3-(2-acetamido-thiazol-5-yl)-2-carboxy-8-oxo-7-(thien-2-yl-acetamido)-5-thia-1-azabicyclo[4.2.0]oct-2-ene (4.25 g) is obtained in the form of a white lyophilisate by treating the corresponding acid (5 g), using the working method described below, in Example 4, with sodium bicarbonate (0.85 g) in water (75 cc) and chromatographing the resulting solution on a column of DUOLITE S 861 (250 cc) (prepared as in Example 4), elution being carried out with distilled water (250 cc) and then with mixtures of water and ethanol, successively 95:5 by volume (250 cc), 90:10 by volume (250 cc) and 80:20 by volume (1,250 cc), and 60 cc fractions being collected, and fractions 5 to 24 subsequently being combined and lyophilised.

Proton nuclear magnetic resonance spectrum (350 MHz, d$_6$ DMSO, δ in ppm, J in Hz): 2.10 (s, 3H, >N—CO—CH$_3$); 3.56 and 3.69 (2d, J=18, 2H, —S—CH$_2$—); 3.73 and 3.80 (2d, J=14, 2H, hetCH$_2$—CON<); 5.02 (d, J=5, 1H, —H in the 6-position); 5.49 (dd, J=9 and 5, 1H, —H in the 7-position); 6.92 to 6.98 (m, 2H, =CH—CH= of the thiophene); 7.36 (dd, J=4.5 and 1, 1H, =CH—S— of the thiophene); 7.44 (s, 1H, —H of the thiazole); 9.07 (d, J=9, 1H, —CO—NH— in the 7-position); 11.87 (s, 1H, Ar—NH—CO—).

3-(2-Acetamido-thiazol-5-yl)-7-amino-2-benzhydryloxycarbonyl-8-oxo-5-thia-1-azabicyclo[4.2.0]oct-2-ene can be obtained in the following manner:

3-(2-Acetamido-thiazol-5-yl)-2-benzhydryloxycarbonyl-7-t-butoxycarbonylamino-8-oxo-5-thia-1-azabicyclo[4.2.0]oct-2-ene (4.6 g) is dissolved in acetonitrile (190 cc) at 35° C. and treated with p-toluenesulphonic acid (monohydrate) (2.9 g) dissolved in acetonitrile (20 cc) for 3 hours at 35° C. and 16 hours at 25° C. and then for a further 6 hours at 35° C. after having added further p-toluenesulphonic acid (monohydrate) (0.95 g). The reaction mixture is partially concentrated under reduced pressure (30 mm Hg; 4 kPa) at 30° C. and then diluted with methylene chloride (200 cc) and saturated sodium bicarbonate solution (200 cc). The aqueous layer is extracted with methylene chloride (100 cc) and the combined organic solutions are washed with water (200 cc) and then dried and concentrated under reduced pressure (30 mm Hg; 4 kPa) at 30° C. The residue is dried under reduced pressure (10 mm Hg; 1.3 kPa) at 25° C. Crude 3-(2-acetamido-thiazol-5-yl)-7-amino-2-benzhydryloxycarbonyl-8-oxo-5-thia-1-azabicyclo[4.2.0]oct-2-ene (3.3 g) is obtained in the form of a beige powder.

Infra-red spectrum (CHBr$_3$): characteristic bands (cm$^{-1}$) at 3440, 3400, 3340, 3260, 3160, 1780, 1720, 1695, 1670, 1560, 1515, 1495, 1450, 1370, 1220 and 760.

Proton nuclear magnetic resonance spectrum (350 MHz, CDCl$_3$, δ in ppm, J in Hz): 2.15 (s, 3H, —CO—CH$_3$); 3.57 and 3.74 (2d, J=18, 2H, —S—CH$_2$—); 4.84 (d, J=4.5, 1H, —H in the 7-position); 5.05 (d, J=4.5, 1H, —H in the 6-position); 6.92 (s, 1H, —COO—CH(C$_6$H$_5$)$_2$); 7.03 (s, 1H, —H of the thiazole); 7.05 to 7.50 (m, aromatic protons); 11.45 (b, 1H, —NH—CO—).

3-(2-Acetamido-thiazol-5-yl)-2-benzhydryloxycarbonyl-7-t-butoxycarbonylamino-8-oxo-5-thia-1-azabicyclo[4.2.0]-oct-2-ene can be obtained in accordance with one of the following processes:

(A) A solution of acetylthiourea (1.8 g) in dry tetrahydrofuran (20 cc) is added, in 5 minutes, to a solution, cooled to 3° C., of the mixture of the epimers of 2-benzhydryloxycarbonyl-7-t-butoxycarbonylamino-3-(1-bromo-2-oxoethyl)-8-oxo-5-thia-1-azabicyclo[4.2.0]oct-2-ene (5.87 g) in dry tetrahydrofuran (58.7 cc). The reaction mixture is then stirred for 4 hours 30 minutes at 25° C. after which it is diluted with ethyl acetate (150 cc) and saturated sodium bicarbonate solution (150 cc). The organic layer is washed with distilled water (2×100 cc) and then with saturated sodium chloride solution (100 cc) and dried. After evaporation of the solvent under reduced pressure (30 mm Hg; 4 kPa) at 30° C., the residue is chromatographed on a column (height: 30 cm; diameter: 6 cm) of silica (0.04–0.06 mm), elution being carried out under a pressure of 0.4 bar (40 kPa) with a 70:30 (by volume) mixture (1600 cc) of cyclohexane and ethyl acetate and then with a 30:70 (by volume) mixture (2000 cc) of cyclohexane and ethyl acetate, 100 cc fractions being collected. Fractions 27 to 33, containing the pure product, are combined and evaporated to dryness. 3-(2-Acetylamino-thiazol-5-yl)-2-benzhydryloxycarbonyl-7-t-butoxycarbonylamino-8-oxo-5-thia-1-azabicyclo[4.2.0]oct-2-ene (0.54 g) is obtained in the form of a yellow froth.

Rf=0.45; silica gel chromatographic plate, eluant: a 27:75 (by volume) mixture of cyclohexane and ethyl acetate.

Infra-red spectrum (CHBr$_3$): characteristic bands (cm$^{-1}$) at 3400, 3270, 3220, 3180, 1790, 1730, 1700, 1545, 1510, 1495, 1455, 1370, 1230, 1165, 760, 745 and 700.

Proton nuclear magnetic resonance spectrum (350 MHz, d$_6$-DMSO, δ in ppm, J in Hz): 1.42 (s, 9H, (CH$_3$)$_3$C—); 2.14 (s, 3H, CH$_3$CO—); 3.76 and 3.88 (AB, J=18, 2H, —SCH$_2$—); 5.17 (d, J=4, 1H, H in the 6-position); 5.59 (dd, J=4 and 9, 1H, H in the 7-position); 6.81 (s, 1H, —CHAr$_2$); 7 to 7.4 (m, 11H, H$_4$ of the thiazole and aromatic protons); 8.04 (d, J=9, 1H, —CONH—C$_7$); 12.05 (s, 1H, —NH—COCH$_3$).

A solution of bromine (0.2 cc) in dry methylene chloride (2 cc) is added dropwise, in 5 minutes, to a solution, cooled to −55° C., of 2-benzhydryloxycarbonyl-7-t-butoxycarbonylamino-3-(2-dimethylamino-vinyl)-8-oxo-5-thia-1-azabicyclo[4.2.0]oct-2-ene (E-isomer) (2 g) in dry tetrahydrofuran (11 cc). The reaction mixture is stirred for 1 hour at −60° C. and then poured into a mixture of ethyl acetate (200 cc) and iced water (200 cc). The organic layer is washed with a half-saturated sodium bicarbonate solution (100 cc) and then with water (100 cc) and half-saturated sodium chloride solution (100 cc) and is dried over sodium sulphate in the presence of decolorising charcoal. After filtration, the solvent is evaporated under reduced pressure (30 mm Hg; 4 kPa) at 30° C. The residue is taken up in isopropyl ether (50 cc) and the latter is evaporated under reduced pressure (30 mm Hg; 4 kPa) at 30° C. 2-Benzhydryloxycarbonyl-3-(1-bromo-2-oxoethyl)-7-t-butoxycarbonylamino-8-oxo-5-thia-1-azabicyclo[4.2.0]oct-2-ene (1.8 g) is obtained in the form of a pale beige solid (a mixture of the two epimers of the bromoaldehyde).

Infra-red spectrum (CHBr$_3$): characteristic bands (cm$^{-1}$) at 3420, 1790, 1725, 1505, 1455, 1390, 1370, 1245, 1225, 760 and 745.

Proton nuclear magnetic resonance spectrum (CDCl$_3$, 350 MHz, δ in ppm, J in Hz):

epimer A 1.42 (s, 9H, (CH$_3$)$_3$C—); 3.71 and 3.55 (AB, J=17.5, 2H, —SCH$_2$—); 5.06 (d, J=4, 1H, H in the 6-position); 5.22 (d, J=9, 1H, —NH—); 5.65 (dd, J=4 and 9, 1H, H in the 7-position); 6.01 (s, 1H, —CHBr—); 6.99 (s, 1H, —CHAr$_2$); 7.3 to 7.5 (m, 10H, aromatic protons); 9.31 (s, 1H, —CHO).

epimer B 1.42 (s, 9H, (CH$_3$)$_3$C—); 3.35 and 3.65 (AB, J=17.5, 2H, —SCH$_2$—); 5.01 (d, J=4, 1H, H in the 6-position); 5.29 (d, J=9, 1H, —NH—); 5.72 (dd, J=4 and 9, 1H, H in the 7-position); 6.00 (s, 1H, —CHBr—); 6.92 (s, 1H, —CHAr$_2$); 7.3 to 7.5 (m, 10H, aromatic protons); 9.30 (s, 1H, —CHO).

2-Benzhydryloxycarbonyl-7-t-butoxycarbonylamino-3-(2-dimethylamino-vinyl)-8-oxo-5-thia-1-azabicyclo[4.2.0]oct-2-ene (E-isomer) can be prepared as described in Belgian Pat. No. 883,415.

(B) A solution of acetyl chloride (1.51 cc) in dry tetrahydrofuran (10 cc) is added dropwise, in 5 minutes, to a solution, cooled to 0° C., of 3-(2-aminothiazol-5-yl)-2-benzhydryloxycarbonyl-7-t-butoxycarbonylamino-8-oxo-5-thia-1-azabicyclo[4.2.0]oct-2-ene (10 g) in dry tetrahydrofuran (150 cc), and a solution of triethylamine (2.8 cc) in dry tetrahydrofuran (5 cc) is then added. The reaction mixture is stirred for 1 hour 30 minutes at about 0°-5° C. and is then treated with further acetyl chloride (1.51 cc) in tetrahydrofuran (10 cc). After 1 hour 50 minutes at 5° C., the reaction mixture is filtered and the filtrate is concentrated to 50 cc and diluted with ethyl acetate (250 cc). The organic phase is washed with a saturated sodium bicarbonate solution (100 cc), with distilled water (100 cc) and with a half-saturated sodium chloride solution (100 cc) and is then dried over magnesium sulphate and concentrated to dryness. Crude 3-(2-acetylamino-thiazol-5-yl)-2-benzhydryloxycarbonyl-7-t-butoxycarbonylamino-8-oxo-5-thia-1-azabicylo[4.2.0]oct-2-ene (10 g) is obtained in the form of a brown froth. Crystallisation from acetonitrile (25 cc) gives pure 3-(2-acetylamino-thiazol-5-yl)-2-benzhydryloxycarbonyl-7-t-butoxycarbonylamino-8-oxo-5-thia-1-azabicyclo[4.2.0]oct-2-ene (5.9 g) in the form of a whitish crystalline powder whose characteristics are identical to those of the product obtained in variant (A).

3-(2-Amino-thiazol-5-yl)-2-benzhydryloxycarbonyl-7-t-butoxycarbonylamino-8-oxo-5-thia-1-azabicyclo[4.2.0]oct-2-ene can be obtained in the following manner:

A suspension of iodine (2.54 g) in dry methylene chloride (20 cc) is added, in 5 minutes, to a solution, cooled to −55° C., of 2-benzhydryloxycarbonyl-7-t-butoxycarbonylamino-3-(2-dimethylamino-vinyl)-8-oxo-5-thia-1-azabicyclo[4.2.0]oct-2-ene, E-form (5.35 g) in dry tetrahydrofuran (20 cc). The reaction mixture is stirred for 2 hours, whilst allowing the temperature gradually to return to 0° C., and is then treated with distilled water (0.36 cc) and stirred for 2 hours at 5° C. A solution of thiourea (0.57 g) in a mixture of tetrahydrofuran (5 cc) and water (2 cc) is added to 25 cc of this reaction mixture and this mixture is stirred for 16 hours at 25° C. Thiourea (0.57 g) is added, stirring is continued for 3 hours at 25° C., and the mixture is then diluted with ethyl acetate (150 cc). The organic phase is washed successively with distilled water (100 cc), saturated sodium bicarbonate solution (100 cc), distilled water (100 cc) and a half-saturated sodium chloride solution (100 cc). After having dried the mixture over magnesium sulphate, the solvent is evaporated under reduced pressure (30 mm Hg; 4 kPa) at 30° C. The residue is chromatographed on a column (height: 30 cm; diameter: 2 cm) of silica (0.04–0.06 mm), elution being carried out under 0.4 bar (40 kPa) with a 45:55 (by volume) mixture of cyclohexane and ethyl acetate. After evaporation of the solvents, 3-(2-amino-thiazol-5-yl)-2-benzhydryloxycarbonyl-7-t-butoxycarbonylamino-8-oxo-5-thia-1-azabicyclo[4.2.0]-oct-2-ene (0.08 g) is obtained in the form of an orange froth, whose characteristics are identical to those of the product described below, in Example 2.

EXAMPLE 2

A solution of 3-(2-benzamido-thiazol-5-yl)-2-benzhydryloxycarbonyl-7-t-butoxycarbonylamino-8-oxo-5-thia-1-azabicyclo[4.2.0]oct-2-ene (2.9 g) in acetonitrile (29 cc) is treated with methanesulphonic acid (2.9 cc) using the working method of Example 15. Crude 7-amino-3-(2-benzamido-thiazol-5-yl)-2-benzhydryloxycarbonyl-8-oxo-5-thia-1-azabicyclo[4.2.0]oct-2-ene (2 g) is obtained in the form of a yellow froth.

Rf=0.22 (silica gel chromatographic plate, eluant: a 30:70 (by volume) mixture of cyclohexane and ethyl acetate).

This product is taken up in dry tetrahydrofuran (50 cc) and acylated with (thien-2-yl)-acetyl chloride (0.53 cc) in the presence of triethylamine (0.6 cc), using the working method described in Example 15. The crude product is chromatographed on a column (height: 22 cm; diameter: 4.4 cm) of silica gel (0.04–0.06 mm), elution being carried out under a pressure of 0.4 bar (40 kPa) with a mixture of cyclohexane and ethyl acetate (50:50 by volume), and 125 cc fractions are collected. Fractions 7 to 16, containing the pure product, are concentrated to dryness under reduced pressure (30 mm Hg; 4 kPa) at 30° C. 3-(2-benzamido-thiazol-5-yl)-2-benzhydryloxycarbonyl-8-oxo-7-(thien-2-yl-acetamido)-5-thia-1-azabicyclo[4.2.0]oct-2-ene (1.5 g) is obtained in the form of a yellow froth.

Infra-red spectrum (CHBr$_3$): characteristic bands (cm$^{-1}$) at 3400, 3300–2500, 1785, 1725, 1675, 1600, 1580, 1535, 1505, 1490, 1450, 755 and 740.

Proton nuclear magnetic resonance spectrum (350 MHz, d$_6$-DMSO, δ in ppm, J in Hz): 3.74 and 3.81 (2d, J=14, 2H, —CH$_2$—CO—N<); 3.81 and 3.95 (2d, J=18, 2H, —CH$_2$—S—); 5.24 (d, J=5, 1H, —H in the 6-position); 5.82 (dd, J=5 and 8, —H in the 7-position); 6.84 (s, 1H, —COO—CH(C$_6$H$_5$)$_2$); 6.90 to 7 (m, 2H, =CH—CH= of the thiophene); 7 to 7.4 (m, 10H, aromatic protons); 7.35 (dd, J=4 and 1, 1H, =CH—S— of the thiophene); 7.42 (s, 1H, —H of the thiazole); 7.55 (t, J=7.5, 2H, aromatic protons in the meta-positions of the benzamido group); 7.66 (t, J=7.5, 1H, aromatic proton in the para-position of the benzamido group); 8.08 (d, J=7.5, 2H, aromatic protons in the ortho-positions of the benzamido group); 9.23 (d, J=8, 1H, —CO—NH—); 12.60 (s, 1H, —NHCO—C$_6$H$_5$).

A solution of 3-(2-benzamido-thiazol-5-yl)-2-benzhydryloxycarbonyl-8-oxo-7-(thien-2-yl-acetamido)-5-thia-1-azabicyclo[4.2.0]oct-2-ene (1.5 g) in a mixture of formic acid (43 cc) and distilled water (8 cc) is heated for 30 minutes at 60° C. and then diluted with distilled water (35 cc). The precipitate is filtered off, washed with 50% strength (by volume) formic acid (2×10 cc) and then with isopropyl ether (3×75 cc) and dried; 3-(2-benzamidothiazol-5-yl)-2-carboxy-8-oxo-7-(thien-2-yl-acetamido)-5-thia-1-azabicyclo[4.2.0]oct-2-ene (1 g) is obtained in the form of a white solid.

Infra-red spectrum (KBr): characteristic bands (cm$^{-1}$) at 3400, 3260, 3100–2100, 1785, 1665, 1605, 1585, 1550, 1495, 1450 and 705.

Proton nuclear magnetic resonance spectrum (350 MHz, d$_6$-DMSO, δ in ppm, J in Hz): 3.73 and 3.82 (2d, J=14, 2H, —CH$_2$—CO—N<); 3.80 and 3.95 (2d, J=18, 2H, —CH$_2$—S—); 5.20 (d, J=5, 1H, —H in the 6-position); 5.75 (dd, J=5 and 9, —H in the 7-position); 6.9 to 7 (m, 2H, =CH—CH= of the thiophene); 7.35 (dd, J=4 and 1, 1H, =CH—S— of the thiophene); 7.53 (t, J=7.5, 2H, aromatic protons in the meta-positions of the benzamido group); 7.63 (s, 1H, —H of the thiazole); 7.64 (t, J=7.5, 1H, aromatic proton in the para-position of the benzamido); 8.10 (d, J=7.5, 2H, aromatic protons in the ortho-positions of the benzamido group); 9.18 (d, J=9, 1H, —CO—NH—); 11.60 (b, 1H, —COOH); 12.45 (b, 1H, —NH—CO—C$_6$H$_5$).

On treating 3-(2-amino-thiazol-5-yl)-2-benzhydryloxycarbonyl-7-t-butoxycarbonylamino-8-oxo-5-thia-1-azabicyclo[4.2.0]oct-2-ene (4.5 g) with benzoyl chloride (1.11 cc) in dry tetrahydrofuran (55 cc) in the presence of triethylamine (1.23 cc), using the working method of Example 1 (B), 3-(2-benzamido-thiazol-5-yl)-2-benzhydryloxycarbonyl-7-t-butoxycarbonylamino-8-oxo-5-thia-1-azabicyclo[4.2.0]-oct-2-ene (1.8 g) is obtained in the form of cream-coloured crystals.

Infra-red spectrum (KBr): characteristic bands (cm$^{-1}$) at 3420, 3240, 1790, 1730, 1705, 1675, 1600, 1580, 1545, 1510, 1500, 1455, 1370, 1160, 760 and 700.

Proton nuclear magnetic resonance spectrum (350 MHz, d$_6$-DMSO, δ in ppm, J in Hz): 1.45 (s, 9H, —C(CH$_3$)$_3$); 3.83 and 3.97 (2d, J=18, 2H, —CH- 2—S—); 5.24 (d, J=5, 1H, —H in the 6-position); 5.67 (dd, J=5 and 9, 1H, —H in the 7-position); 6.91 (s, 1H, —COO—CH($C_6H_5$)$_2$); 7.05 to 7.45 (m, 10H, aromatic protons); 7.49 (s, 1H, —H of the thiazole); 7.63 (t, J=7.5, 2H, aromatic protons in the meta-positions of the benzamido group); 7.72 (t, J=7.5, 1H, aromatic proton in the para-position of the benzamido group); 8.13 (d, J=9, 1H, —CO—NH—); 8.16 (d, J=7.5, 2H, aromatic protons in the ortho-positions of the benzamido group); 12.72 (s, 1H, —NH—CO—$C_6H_5$).

A solution of 2-benzhydryloxycarbonyl-7-t-butoxycarbonylamino-3-(2-dimethylamino-vinyl)-8-oxo-5-thia-1-azabicyclo[4.2.0]oct-2-ene, E-isomer (107.13 g) in dry tetrahydrofuran (500 cc) is cooled to −50° C. A solution of bromine (10.25 cc) in dry methylene chloride (30 cc) is added dropwise in 35 minutes. The temperature is allowed to rise to −15° C. in 1 hour and distilled water (7.2 cc) is then added. The reaction mixture is stirred for 45 minutes at between −15° C. and −5° C. and then treated with a solution of thiourea (22.8 g) in a mixture of tetrahydrofuran (100 cc) and distilled water (20 cc). The mixture is stirred for 3 hours at 25° C., then concentrated to a residual volume of 350 cc, and diluted with ethyl acetate (1500 cc). The organic layer is washed successively with a saturated sodium bicarbonate solution (500 cc), a half-saturated sodium bicarbonate solution (500 cc), distilled water (2×500 cc) and a half-saturated sodium chloride solution (2×500 cc), dried over sodium sulphate and concentrated to dryness under reduced pressure (30 mm Hg; 4 kPa) at 40° C. The residue is fixed onto silica (0.2–0.063 mm) (400 cc) and chromatographed on a column (diameter: 9 cm) of silica (0.2–0.063 mm) (900 g), elution being carried out with mixtures of cyclohexane and ethyl acetate, successively of the following compositions (by volume): 70:30 (2 liters); 50:50 (6 liters); 40:60 (2 liters) and 20:80 (2 liters), and then with pure ethyl acetate (4 liters), 800 cc fractions being collected. Fractions 10 to 15, containing the pure product, are combined and concentrated to dryness under reduced pressure (30 mm Hg; 4 kPa) at 40° C. 3-(2-Aminothiazol-5-yl)-2-benzhydryloxycarbonyl-7-t-butoxycarbonylamino-8-oxo-5-thia-1-azabicyclo[4.2.0]oct-2-ene (34.4 g) is obtained in the form of an orange froth.

Infra-red spectrum (CHBr$_3$): characteristic bands (cm$^{-1}$) at 3480, 3420, 3380, 1780, 1720, 1600, 1495, 1455, 1390, 1370, 1240, 1220, 755 and 740.

Proton nuclear magnetic resonance spectrum (350 MHz, CDCl$_3$, δ in ppm, J in Hz): 1.47 (s, 9H, —C(CH$_3$)$_3$); 3.46 and 3.61 (2d, J=18, 2H, —S—CH$_2$—); 5.01 (d, J=4.5, 1H, —H in the 6-position); 5.27 (b, 2H, —NH$_2$); 5.57 (d, J=9, 1H, —CO—NH—); 5.64 (dd, J=9 and 4.5, 1H, —H in the 7-position); 6.85 (s, 1H, —COO—CH(C$_6$H$_5$)$_2$); 6.94 (s, 1H, —H of the thiazole); 7.10 to 7.50 (m, 10H, aromatic protons).

EXAMPLE 3

Following the procedure of Example 2, starting from 3-(2-amino-thiazol-5-yl)-2-benzhydryloxycarbonyl-7-t-butoxycarbonylamino-8-oxo-5-thia-1-azabicyclo[4.2.0]oct-2-ene (4.5 g), triethylamine (1.23 cc) and 2-chlorocarbonyl-thiophene (1.4 g), 2-benzhydryloxycarbonyl-7-t-butoxycarbonylamino-8-oxo-3-[2-(thien-2-yl-carbonylamino)-thiazol-5-yl]-5-thia-1-azabicyclo[4.2.0]oct-2-ene (4.62 g) is obtained, in the form of a cream-coloured powder, after purification over Merck silica gel (0.06–0.2 mm).

Infra-red spectrum (KBr): characteristic bands (cm$^{-1}$) at 3420, 3230, 1790, 1730, 1700, 1660, 1545, 1505, 1165, 850 and 740.

Proton nuclear magnetic resonance spectrum (360 MHz, CDCl$_3$, δ in ppm; J in Hz): 1.49 (s, 9H, —C(CH$_3$)$_3$); 3.55 and 3.71 (2d, J=18, 2H, —SCH$_2$—); 5.07 (d, J=5, 1H, H in the 6-position); 5.33 (d, J=9, 1H, —CONH—); 5.72 (dd, J=5 and 9, 1H, H in the 7-position); 6.94 (s, 1H, —COOCH—); 7.0 (s broad, 1H, H in the 4-position of the thiophene); 7.69 (d, J=4.5, 1H, H in the 3-position of the thiophene); 7.74 (s broad, 1H, H in the 5-position of the thiophene).

2-Benzhydryloxycarbonyl-7-t-butoxycarbonylamino-8-oxo-3-[2-(thien-2-yl-carbonylamino)-thiazol-5-yl]-5-thia-1-azabicyclo[4.2.0]oct-2-ene (4.62 g) is treated with trifluoroacetic acid (45 cc) for 30 minutes at 20° C. The mixture is concentrated to dryness at 20° C. under 0.05 mm Hg (0.007 kPa) and the residue is taken up in ethyl acetate (2×50 cc), in each case concentrated to dryness at 30° C. under 20 mm Hg (2.7 kPa). The solid which remains is triturated in diethyl ether (100 cc). After filtration, 7-amino-2-carboxy-8-oxo-3-[2-(thien-2-yl-carbonylamino)thiazol-5-yl]-5-thia-1-azabicyclo[4.2.0]oct-2-ene (3.45 g) as the trifluoroacetate is obtained in the form of a yellow crude powder.

Infra-red spectrum (KBr): characteristic bands (cm$^{-1}$) at 3300–3200, 1790, 1670, 1555, 1200, 1150, 840, 800 and 725.

On proceeding as in Example 6, starting from 7-amino-2-carboxy-8-oxo-3-[2-(thien-2-yl-carbonylamino)-thiazol-5-yl]-5-thia-1-azabicyclo[4.2.0]oct-2-ene trifluoroacetate (3.45 g) and (thien-2-yl)-acetyl chloride (0.839 cc), a cream-coloured crude powder (1.52 g) is obtained. This is purified in the form of the sodium salt, in aqueous solution, by passage on a column of DUOLITE S 861 resin (20 cc) (column diameter: 2 cm). Elution is carried out with water (250 cc), water containing 5% of ethanol (250 cc), water containing 10% of ethanol (250 cc) and water containing 20% of ethanol (250 cc), and 30 cc fractions are collected. Fractions 9 to 25 are lyohilised. 2-Carboxy-8-oxo-7-[2-(thien-2-yl)-acetamido]-3-[2-(thien-2-yl-carbonylamino)-thiazol-5-yl]-5-thia-1-azabicyclo[4.2.0]oct-2-ene in the form of the sodium salt (0.5 g) is obtained in the form of a cream-coloured lyophilisate.

Infra-red spectrum (KBr): characteristic bands (cm$^{-1}$) at 3300, 1755, 1650, 1610, 1555, 1505, 1410 and 730.

EXAMPLE 4

On treating 2-benzhydryloxycarbonyl-7-t-butoxycarbonylamino-3-(2-N-methylacetamido-thiazol-5-yl)-8-oxo-5-thia-1-azabicyclo[4.2.0]oct-2-ene (5.56 g) with methanesulphonic acid (4 cc) in acetonitrile (50 cc), using the working method of Example 15, crude 7-amino-2-benzhydryloxycarbonyl-3-(2-N-methylacetamido-thiazol-5-yl)-8-oxo-5-thia-1-azabicyclo[4.2.0]oct-2-ene (4.6 g) is obtained, and this is acylated with (thien-2-yl)-acetyl chloride (1.25 cc) in accordance with the working method described in Example 1. The product is chromatographed on a column (height: 30 cm; diameter: 6 cm) of silica gel (0.04–0.06 mm), elution being carried out, under a pressure of 0.5 bar (50 kPa), with a mixture of cyclohexane and ethyl acetate (35:65 by volume), and 100 cc fractions are collected. Fractions 18 to 28, containing the pure product, are combined and concentrated to dryness under reduced pressure (30 mm Hg) at 30° C. 2-Benzhydryloxycarbonyl-3-(2-N-methylacetamido-thiazol-5-yl)-8-oxo-7-[(thien-2-yl)-acetamido]-5-thia-1-azabicyclo[4.2.0]oct-2-ene (3.34 g) is obtained in the form of a cream-coloured froth.

Infra-red spectrum (CHCl$_3$): characteristic bands (cm$^{-1}$) at 3400, 1790, 1730, 1680, 1510, 1465, 1380 and 695.

Proton nuclear magnetic resonance spectrum (350 MHz, CDCl$_3$, δ in ppm, J in Hz): 2.40 (s, 3H, >N—CO—CH$_3$); 3.53 and 3.68 (2d, J=18, 2H, —S—CH$_2$—); 3.54 (s, 3H, >NCH$_3$); 3.88 (limiting AB system, 2H, hetCH$_2$CON<); 5.06 (d, J=5, 1H, —H in the 6-position); 5.92 (dd, J=9 and 5, 1H, —H in the 7-position); 6.33 (d, J=9, 1H, —CO—NH—); 6.89 (s, 1H, —COO—CH(C$_6$H$_5$)$_2$); 7.12 (s, 1H, —H of the thiazole); 7 to 7.35 (m, aromatic protons and thienyl).

2-Benzhydryloxycarbonyl-3-(2-N-methylacetamido-thiazol-5-yl)-8-oxo-7-[(thien-2-yl)-acetamido]-5-thia-1-azabicyclo[4.2.0]oct-2-ene (3.3 g) is dissolved in a mixture of formic acid (20 cc) and anisole (7 cc) at 50° C. After 20 minutes at this temperature, the reaction mixture is concentrated to dryness under reduced pressure (2 mm Hg; 0.3 kPa) at 30° C. The residue is triturated with absolute ethanol (100 cc) and the latter is evaporated under reduced pressure (30 mm Hg; 4 kPa) at 30° C. The residue is triturated with absolute ethanol (150 cc) at 50° C. The insoluble matter is filtered off, washed with absolute ethanol (50 cc) and then with isopropyl ether (3×50 cc) and dried. 2-Carboxy-3-(2-N-methylacetamido-thiazol-5-yl)-8-oxo-7-[(thien-2-yl)-acetamido]-5-thia-1-azabicyclo[4.2.0]-oct-2-ene (1.44 g) is obtained in the form of a creamy white solid which is redissolved in a solution of sodium bicarbonate (0.25 g) in distilled water (15 cc). The solution is filtered and then poured onto a column (diameter: 2 cm) of DUOLITE S 861 resin (70 cc) (the resin having first been washed with alcohol (250 cc), distilled water (250 cc), then with a 1% strength sodium chloride solution until neutral, and then with distilled water until the chloride ions have been removed). Elution is carried out successively with distilled water (450 cc) and with a water-ethanol mixture (95:5 by volume) (450 cc), and 30 cc fractions are collected. Fractions 5 to 24 are combined and lyophilised. The sodium salt of 2-carboxy-3-(2-N-methylacetamido-thiazol-5-yl)-8-oxo-7-[(thien-2-yl)-acetamido]-5-thia-1-azabicyclo[4.2.0]oct-2-ene (1.17 g) is obtained in the form of a pale yellow lyophilisate.

Infra-red spectrum (KBr): characteristic bands (cm$^{-1}$) at 3300, 1760, 1670, 1605, 1530, 1380 and 700.

Proton nuclear magnetic resonance spectrum (350 MHz, d$_6$ DMSO, δ in ppm, J in Hz): 2.35 (s, 3H, >N—CO—CH$_3$); 3.56 and 3.68 (2d, J=18, 2H, —CH$_2$—S—); 3.58 (s, 3H, >N—CH$_3$); 3.78 (limiting AB system, J=14, 2H, het—CH$_2$—CO—N>); 5.04 (d, J=4.5, 1H, —H in the 6-position); 5.50 (dd, J=4.5 and 8, 1H, —H in the 7-position); 6.92 to 6.97 (m, 2H, =CH—CH= of the thiophene); 7.37 (dd, J=4.5 and 1, 1H, =CH—S— of the thiophene); 7.51 (s, 1H, —H of the thiazole); 9.09 (d, J=8, 1H, —CO—NH— in the 7-position).

2-Benzhydryloxycarbonyl-7-t-butoxycarbonylamino-3-(2-N-methylacetamido-thiazol-5-yl)-8-oxo-5-thia-1-azabicyclo[4.2.0]oct-2-ene can be prepared in the following manner:

2-Benzhydryloxycarbonyl-7-t-butoxycarbonylamino-3-(2-methylamino-thiazol-5-yl)-8-oxo-5-thia-1-azabicyclo[4.2.0]oct-2-ene (7 g) is dissolved in dry tetrahydrofuran (45 cc) at 0° C. and treated with a solution of acetyl chloride (1.7 cc) in dry tetrahydrofuran (5 cc) and then with triethylamine (3.1 cc) dissolved in tetrahydrofuran (5 cc). The reaction mixture is stirred for 6 hours at 0° C. and 16 hours at 25° C. and is then diluted with ethyl acetate (250 cc) and washed with water (100 cc) to which saturated sodium bicarbonate solution (50 cc) has been added, thereafter with distilled water (2×250 cc) and then with a saturated sodium chloride solution (100 cc). After drying over magnesium sulphate, filtration and evaporation of the solvent under reduced pressure (30 mm Hg; 4 kPa) at 30° C., the residue obtained is purified by chromatography on a column (height: 30 cm, diameter: 6 cm) of silica gel (0.04–0.06 mm), elution being carried out under a pressure of 50 kPa, using a mixture (35:65 by volume) of cyclohexane and ethyl acetate and collecting 100 cc fractions. Fractions 10 to 18, containing the pure product, are combined and concentrated to dryness under reduced pressure (30 mm Hg; 4 kPa) at 30° C. 2-Benzhydryloxycarbonyl-7-t-butoxycarbonylamino-3-(2-N-methylacetamidothiazol-5-yl)-8-oxo-5-thia-1-azabicyclo[4.2.0]oct-2-ene (5.33 g) is obtained in the form of a cream-coloured froth.

Infra-red spectrum (CHCl$_3$): characteristic bands (cm$^{-1}$) at 3340, 1785, 1720, 1670, 1505, 1460, 1380, 1370, 1160 and 700.

Proton nuclear magnetic resonance spectrum (350 MHz, CDCl$_3$, δ in ppm, J in Hz): 1.48 (s, 9H, —C(CH$_3$)$_3$); 2.4 (s, 3H, >N—CO—CH$_3$); 3.54 (s, 3H, >N—CH$_3$); 3.58 and 3.72 (2d, J=18, 2H, —CH$_2$—S—); 5.07 (d, J=5, 1H, —H in the 6-position); 5.26 (d, J=9, 1H, —CO—NH—); 5.7 (dd, J=9 and 5, 1H, —H in the 7-position); 6.9 (s, 1H, —COO—CH(C$_6$H$_5$)$_2$); 7.05 to 7.45 (m, aromatic protons and —H of the thiazole).

2-Benzhydryloxycarbonyl-7-t-butoxycarbonylamino-3-(2-methylamino-thiazol-5-yl)-8-oxa-5-thia-1-azabicyclo[4.2.0]oct-2-ene can be prepared by following the working method of Example 2, but replacing the thiourea by N-methylthiourea (4 g). Starting from 2-benzhydryloxycarbonyl-7-t-butoxycarbonylamino-3-(2-dimethylamino-vinyl)-8-oxo-5-thia-1-azabicyclo[4.2.0]oct-2-ene (E-form)(20 g), and following purification by chromatography on a column (height: 45 cm, diameter: 4 cm) of silica gel (0.2–0.06 mm), elution being carried out with mixtures of cyclohexane and ethyl acetate, successively 50:50 by volume (1.5 liters), 40:60 by volume (1 liter) and 20:80 by volume (1.5 liters), and then with ethyl acetate (1 liter), and the fractions containing the expected product (according to thin layer chromatography) being combined and evaporated to dryness under reduced pressure (30 mm Hg; 4 kPa) at 30° C., 2-benzhydryloxycarbonyl-7-t-butoxycarbonylamino-3-(2-methylamino-thiazol-5-yl)-8-oxo-5-thia-1-azabicyclo[4.2.0]oct-2-ene (4.74 g) is obtained in the form of a pale brown froth.

Infra-red spectrum (CHCl$_3$): characteristic bands (cm$^{-1}$) at 3440, 1785, 1725, 1560, 1510, 1460, 1396, 1370, 1160 and 700.

Proton nuclear magnetic resonance spectrum (350 MHz, d$_6$-DMSO, δ in ppm, J in Hz): 1.44 (s, 9H, (CH$_3$)$_3$C—); 2.73 (d, J=5, 3H, >N—CH$_3$); 3.72 and 3.80 (AB, J=18, 2H, —SCH$_2$—); 5.16 (d, J=4.5, 1H, H in the 6-position); 5.49 (dd, J=4.5 and 9, 1H, H in the 7-position); 6.84 (s, 1H, —CHAr$_2$); 7.2 to 7.45 (m, 11H, aromatic protons); 7.79 (q, J̄=5, 1H, —NHCH$_3$); 8.04 (d, J=9, 1H, —CONH—).

EXAMPLE 5

Following the working method described in Example 15, but starting from 2-benzhydryloxycarbonyl-7-t-butoxycarbonylamino-8-oxo-3-(thiazol-5-yl)-5-thia-1-azabicyclo[4.2.0]oct-2-ene (3.85 g), the 7-amino derivative is prepared by the action of methanesulphonic acid (3.8 cc) in acetonitrile (38 cc), and thereafter the crude 7-amino-2-benzhydryloxycarbonyl-8-oxo-3-(thiazol-5-yl)-5-thia-1-azabicyclo[4.2.0]oct-2-ene obtained is acylated with (thien-2-yl)-acetyl chloride (0.86 cc) in dry tetrahydrofuran (65 cc) in the presence of triethylamine (0.98 cc). After chromatography on a column (height: 30 cm; diameter=4 cm) of silica gel (0.04–0.06 mm), elution being carried out under a pressure of 0.4 bar (40 kPa) with a 30:70 (by volume) mixture of cyclohexane and ethyl acetate, fractions 11 to 20 (each of 40 cc), containing the pure product, are concentrated to dryness under reduced pressure, giving 2-benzhydryloxycarbonyl-8-oxo-3-(thiazol-5-yl)-7-(thien-2-yl-acetamido)-5-thia-1-azabicyclo[4.2.0]oct-2-ene (2.67 g) in the form of a cream-coloured froth.

Infra-red spectrum (CHCl$_3$): characteristic bands (cm$^{-1}$) at 3400, 1790, 1730, 1690, 1505 and 695.

Proton nuclear magnetic resonance spectrum (350 MHz, CDCl$_3$, δ in ppm, J in Hz): 3.51 and 3.71 (2d, J=18, 2H, —S—CH$_2$—): 3.88 (s, 2H, —CH$_2$CO—N<); 5.09 (d, J=5, 1H, —H in the 6-position); 5.94 (dd, J=5 and 9, 1H, —H in the 7-position); 6.43 (d, J=9, 1H, —CO—NH—); 6.90 (s, 1H, —COO—CH(C$_6$H$_5$)$_2$); 6.98 to 7.05 (m, H$_3$ and H$_4$ of the thiophene); 7.05 to 7.45 (m, 11H, aromatic protons and H$_5$ of the thiophene); 7.55 (s, 1H, H$_4$ of the thiazole); 8.59 (s, 1H, H$_2$ of the thiazole).

On using the working method described in Example 1, but starting from 2-benzhydryloxycarbonyl-8-oxo-3-(thiazol-5-yl)-7-(thien-2-yl-acetamido)-5-thia-1-azabicyclo[4.2.0]-oct-2-ene (2.55 g), 2-carboxy-8-oxo-3-(thiazol-5-yl)-7-(thien-2-yl-acetamido)-5-thia-1-azabicyclo[4.2.0]oct-2-ene (1.03 g) is obtained in the form of a beige solid.

Infra-red spectrum (KBr): characteristic bands (cm$^{-1}$) at 3260, 3150–2200, 1780, 1655, 1540, 1220 and 700.

Proton nuclear magnetic resonance spectrum (350 MHz, d$_6$-DMSO, δ in ppm, J in Hz): 3.80 and 3.87 (2 limiting AB systems, 4H, —CH$_2$—CO—N< and —CH$_2$—S—); 5.20 (d, J=4.5, 1H, —H in the 6-position); 5.76 (dd, J=9 and 4.5, 1H, —H in the 7-position); 6.90 to 7 (m, 2H, H$_3$ and H$_4$ of the thiophene); 7.35 (dd, J=5 and 1, 1H, H in the 5-position of the thiophene); 7.91 (s, 1H, H$_4$ of the thiazole); 9.09 (s, 1H, H in the 2-position of the thiazole); 9.19 (d, J=9, 1H, —CO—NH—); 13.65 (b, 1H, —COOH).

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the epimeric bromoaldehydes) (2.34 g) and of thioformamide (0.3 g) in dry tetrahydrofuran (23 cc) is stirred for 3 hours at 20° C. and then heated at 50° C. for 90 minutes. The reaction mixture is diluted with ethyl acetate (160 cc) and washed with saturated sodium bicarbonate solution (100 cc) and then with half-saturated sodium chloride solution (100 cc). After having dried the organic layer over magnesium sulphate and evaporated the solvent under reduced pressure (30 mm Hg; 4 kPa) at 30° C., the residue obtained is subjected to chromatography on a column (height: 30 cm; diameter: 2.5 cm) of silica gel (0.04–0.06 mm), elution being carried out under a pressure of 0.8 bar (80 kPa) with a 70:30 (by volume) mixture of cyclohexane and ethyl acetate, and 50 cc fractions being collected. Fractions 16 to 25, containing the pure product, are combined and concentrated to dryness under reduced pressure (30 mm Hg; 4 kPa) at 30° C., and the residue is triturated in isopropyl ether (50 cc). After filtration and drying, 2-benzhydryloxycarbonyl-7-t-butoxycarbonylamino-8-oxo-3-(thiazol-5-yl)-5-thia-1-azabicyclo[4.2.0]oct-2-ene (0.85 g) is obtained in the form of a cream-coloured solid.

Infra-red spectrum (CHBr$_3$): characteristic bands (cm$^{-1}$) at 3420, 1790, 1725, 1505, 1500, 1455, 1390, 1370, 870, 760 and 740.

Proton nuclear magnetic resonance spectrum (350 MHz, CDCl$_3$, δ in ppm, J in Hz): 1.49 (s, 9H, —C(CH$_3$)$_3$); 3.56 and 3.74 (2d, J=18, 2H, —S—CH$_2$—); 5.09 (d, J=4.5, 1H, —H in the 6-position); 5.32 (d, J=9, 1H, —CO—NH—); 5.72 (dd, J=9 and 4.5, 1H, —H in the 7-position); 6.91 (s, 1H, —COOCH(C$_6$H$_5$)$_2$); 7 to 7.4 (m, 10H, aromatic protons), 7.58 (s, 1H, H$_4$ of the thiazole); 8.58 (s, 1H, H$_2$ of the thiazole).

EXAMPLE 6

A solution of 7-amino-2-carboxy-8-oxo-3-(2-phenyl-thiazol-5-yl)-5-thia-1-azabicyclo[4.2.0]oct-2-ene (3.3 g) in a mixture of distilled water (35 cc) and acetone (24 cc) containing sodium bicarbonate (2 g) is cooled to −10° C. and then treated with a solution of (thien-2-yl)-acetyl chloride (0.86 cc) in acetone (10 cc), which is added dropwise in 8 minutes. The reaction mixture is stirred for 30 minutes at −10° C. and then for 3 hours at 20° C. The acetone is evaporated under reduced pressure (30 mm Hg; 4 kPa) at 30° C. and ethyl acetate (150 cc) and a saturated sodium bicarbonate solution (100 cc) are added. The aqueous layer is extracted with ethyl acetate (100 cc), then treated with decolorising charcoal (1 g) and a filtration aid (diatomaceous earth powder) (5 g), and filtered on the filtration aid, rinsing with distilled water (2×50 cc). The combined filtrates are acidified to pH 2 with 4N hydrochloric acid. The precipitate is filtered off, washed with ethyl acetate (50 cc) and then triturated with isopropyl ether (100 cc) and dried. 2-Carboxy-8-oxo-3-(2-phenyl-thiazol-5-yl)-7-(thien-2-yl-acetamido)-5-thia-1-azabicyclo[4.2.0]oct-2-ene (0.8 g) is obtained in the form of a cream-coloured solid.

Infra-red spectrum (KBr): characteristic bands (cm$^{-1}$) at 3290, 2700–2200, 1780, 1730, 1690, 1530, 1450 and 690.

Proton nuclear magnetic resonance spectrum (350 MHz, d$_6$-DMSO, δ in ppm, J in Hz): 3.74 and 3.82 (2d, J=14, 2H, —CH$_2$—CO—N<); 3.86 and 3.96 (2d, J=18, 2H, —S—CH$_2$—); 5.23 (d, J=4.5, 1H, —H in the 6-position); 5.77 (dd, J=4.5 and 9, 1H, —H in the 7-position); 6.90 to 7 (m, 2H, =CH—CH= of the thiophene); 7.35 (dd, J=4.5 and 1, 1H, =CH—S— of the thiophene); 7.45 to 7.55 (m, 3H, aromatic —H of the benzene in the meta-positions and in the para-position to the thiazole); 7.92 (d, J=8, 2H, aromatic —H of the benzene in the ortho-positions to the thiazole); 7.93 (s, 1H, —H of the thiazole); 9.21 (d, J=9, 1H, —CO—NH—).

2-Carboxy-8-oxo-3-(2-phenyl-thiazol-5-yl)-7-(thien-2-yl-acetamido)-5-thia-1-azabicyclo[4.2.0]oct-2-ene (0.336 g) is dissolved in a solution of sodium bicarbonate (0.05 g) in water (10 cc). After having been washed with ethyl acetate (25 cc), the aqueous phase is filtered and then lyophilized. The sodium salt of 2-carboxy-8-oxo-3-

(2-phenyl-thiazol-5-yl)-7-(thien-2-yl-acetamido)-5-thia-1-azabicyclo[4.2.0]oct-2-ene (0.32 g) is obtained in the form of a beige lyophilizate.

Infra-red spectrum (KBr): characteristic bands ($cm^{-1}$) at 3280, 1760, 1665, 1605, 1545, 1495, 1450, 1395 and 690.

Proton nuclear magnetic resonance spectrum (350 MHz, $d_6$-DMSO $\delta$ in ppm, J in HZ): 3.68 and 3.81 (2d, J=16, 2H, —$SCH_2$—); 3.77 (s, 2H, —$CH_2CO$—); 5.08 (d, J=5, 1H, H in the 6-position); 5.54 (dd, J=5 and 8, 1H, H in the 7-position); 6.9 to 7 (m, 2H, $H_3$ and $H_4$ of the thienyl); 7.36 (dd, J=1 and 5, 1H, $H_5$ of the thienyl); 7.4 to 7.5 (m, 3H, $H_3$, $H_4$ and $H_5$ of the phenyl); 7.85 (d, J=7.5, 2H, $H_2$ and $H_6$ of the phenyl); 7.90 (s, 1H, H in the 4-position of the thiazole); 9.15 (d, J=9, 1H, —CONH—).

7-Amino-2-carboxy-8-oxo-3-(2-phenyl-thiazol-5-yl)-5-thia-1-azabicyclo[4.2.0]oct-2-ene can be obtained in the following manner:

2-Benzhydryloxycarbonyl-7-t-butoxycarbonylamino-8-oxo-3-(2-phenyl-thiazol-5-yl)-5-thia-1-azabicyclo[4.2.0]-oct-2-ene (5.7 g) is treated with trifluoroacetic acid (57 cc) for 20 minutes at 20° C. and the reaction mixture is then concentrated to dryness under reduced pressure (0.2 mm Hg; 0.03 kPa) at 30° C. The residue is taken up in ethyl acetate (100 cc), which is evaporated under reduced pressure (30 mm Hg; 4 kPa) at 30° C. This residue is triturated with isopropyl ether (100 cc). The solid is filtered off, washed with isopropyl ether (3×50 cc) and dried under reduced pressure (0.2 mm Hg; 0.03 kPa) at 20° C. 7-Amino-2-carboxy-8-oxo-3-(2-phenyl-thiazol-5-yl)-5-thia-1-azabicyclo[4.2.0]oct-2-ene (3.3 g) is obtained in the form of an ochre solid.

Infra-red spectrum (KBr): characteristic bands ($cm^{-1}$) at 3300 to 2000, 1785, 1615, 1400, 760 and 690.

Proton nuclear magnetic resonance spectrum (350 MHz, $d_6$-DMSO, $\delta$ in ppm, J in Hz): 3.82 and 3.92 (d, J=18, 2H, —S—$CH_2$—); 4.92 (d, J=4.5, 1H, —H in the 7-position); 5.13 (d, J=4.5, 1H, —H in the 6-position); 7.40 to 7.60 (m, aromatic —H of the benzene in the meta-positions and in the para-position to the thiazole); 7.85 to 8 (m, aromatic —H of the benzene in the ortho-positions to the thiazole, and —H of the thiazole).

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (a mixture of the bromoaldehyde epimers) (5.87 g) and thiobenzamide (1.5 g) in dry tetrahydrofuran (60 cc) is stirred at 20° C. for 1 hour 20 minutes, and thereafter there are added to the reaction mixture, cooled to 2° C., methanesulphonyl chloride (0.85 cc) followed, in 5 minutes, by triethylamine (5.6 cc). After having been stirred for 2 hours at 2° C., the reaction mixture is poured into a mixture of ethyl acetate (100 cc) and 1N hydrochloric acid (50 cc). The organic phase is washed with a saturated sodium bicarbonate solution (100 cc) and then with a saturated sodium chloride solution (100 cc), dried over magnesium sulphate and concentrated to dryness under reduced pressure (30 mm Hg; 4 kPa) at 30° C. The residue is chromatographed on a column (height: 25 cm; diameter: 5 cm) of silica gel (0.04–0.06 mm), elution being carried out under a pressure of 0.4 bar (40 kPa) with an 80:20 (by volume) mixture of cyclohexane and ethyl acetate, and 125 cc fractions being collected. Fractions 17 to 22, containing the pure product, are combined and concentrated to dryness under reduced pressure (30 mm Hg; 4 kPa) at 30° C. 2-Benzhydryloxycarbonyl-7-t-butoxycarbonylamino-8-oxo-3-(2-phenyl-thiazol-5-yl)-5-thia-1-azabicyclo[4.2.0]oct-2-ene (1 g) is obtained in the form of a yellow froth.

Infra-red spectrum ($CHBr_3$): characteristic bands ($cm^{-1}$) at 3420, 1790, 1720, 1595, 1495, 1450, 1500, 1420, 1390, 1370, 1235, 760 and 740.

Proton nuclear magnetic resonance spectrum (350 MHz, $CDCl_3$ $\delta$ in ppm, J in Hz): 1.48 (s, 9H, —$C(CH_3)_3$); 3.62 and 3.78 (2d, J=18, 2H, —$CH_2$—S—); 5.10 (d, J=5, 1H, —H in the 6-position); 5.29 (d, J=9, 1H, —CO—NH—); 5.73 (dd, J=5 and 9, 1H, —H in the 7-position); 6.96 (s, 1H, —$COOCH(C_6H_5)_2$); 7 to 7.5 (m, aromatic protons); 7.54 (s, 1H, —H of the thiazole); 7.77 (m, 2H, aromatic —H of the phenyl in the ortho-positions to the thiazole).

EXAMPLE 7

On treating 3-[2-(4-acetamido-phenyl)-thiazol-5-yl]-2-benzhydryloxycarbonyl-7-t-butoxycarbonylamino-8-oxo-5-thia-1-azabicyclo[4.2.0]oct-2-ene (3.4 g) with methanesulphonic acid (3.4 cc) in acetonitrile (15 cc), in accordance with the working method described in Example 15, crude 7-amino-3-[2-(4-acetamido-phenyl)-thiazol-5-yl]-2-benzhydryloxycarbonyl-8-oxo-5-thia-1-azabicyclo[4.2.0]oct-2-ene (2.9 g) is obtained, and this is acylated with (thien-2-yl)-acetyl chloride (0.62 cc) in accordance with the working method described in Example 1. The crude product obtained is purified by crystallisation from acetonitrile (200 cc). 3-[2-(4-Acetamido-phenyl)-thiazol-5-yl]-2-benzhydryloxycarbonyl-8-oxo-7-[(thien-2-yl)-acetamido]-5-thia-1-azabicyclo[4.2.0]oct-2-ene (1.33 g) is obtained in the form of a beige crystalline powder.

Infra-red spectrum (KBr): characteristic bands ($cm^{-1}$) at 3280, 1785, 1730, 1680, 1600, 1530, 1230, 850, 760, 750 and 700.

Proton nuclear magnetic resonance spectrum (350 MHz, $CDCl_3$, $\delta$ ppm, J in Hz): 2.25 (s, 3H, >N—CO—$CH_3$); 3.56 and 3.72 (2d, J=18, 2H, —S—$CH_2$—); 3.89 (s, 2H, het-$CH_2$—CON<); 5.09 (d, J=4.5, 1H, —H in the 6-position); 5.94 (dd, J=9 and 4.5, 1H, —H in the 7-position); 6.36 (d, J=9, 1H, —CONH—), 6.94 (s, 1H, —COO—$CH(C_6H_5)_2$); 7 to 7.45 (m, aromatic protons, —H of the thiophene); 7.47 (s, 1H, —H of the thiazole); 7.58 (d, J=7.5, 2H, aromatic —H in the meta-positions to the thiazole); 7.70 (d, J=7.5, 2H, aromatic —H in the ortho-positions to the thiazole).

Following the working method described in Example 4, 3-[2-(4-acetamido-phenyl)-thiazol-5-yl]-2-benzhydryloxycarbonyl-8-oxo-7-[(thien-2-yl)-acetamido]-5-thia-1-azabicyclo[4.2.0]oct-2-ene (1.5 g) is treated with formic acid (25 cc) and anisole (5 cc) at 50° C. for 20 minutes. 3-[2-(4-acetamido-phenyl)-thiazol-5-yl]-2-carboxy-8-oxo-7-[(thien-2-yl)-acetamido]-5-thia-1-azabicyclo[4.2.0]oct-2-ene (0.99 g) is obtained in the form of a yellow solid.

Infra-red spectrum (KBr): characteristic bands ($cm^{-1}$) at 3400, 3320, 2650–1850, 1790, 1695, 1670, 1600, 1540, 840 and 705.

Proton nuclear magnetic resonance spectrum (350 MHz, $d_6$ DMSO, $\delta$ in ppm, J in Hz): 2.09 (s, 3H, >N—CO—$CH_3$); 3.74 and 3.82 (2d, J=14, 2H, het—$CH_2$—CO—N<); 3.86 and 3.96 (2d, J=18, 2H, —S—$CH_2$—); 5.21 (d, J=4.5, 1H, —H in the 6-position); 5.76 (dd, J=8 and 4.5, 1H, —H in the 7-position); 6.94 to 7 (m, 2H, =CH—CH= of the thiophene); 7.37 (dd, J=4.5 and 1, 1H, =CH—S— of the thiophene); 7.71 (d, J=8, 2H, aromatic —H in the meta-positions to the thiazole); 7.82 (d, J=8, 2H, aromatic —H in the ortho-positions to the thiazole); 7.88 (s, 1H, —H of the thiazole); 9.22 (d, J=8, 1H, —NH—CO— in the 7-position); 10.20 (s, 1H, Ar—NH—CO—).

Following the working method described in Example 4, this acid (0.97 g) is treated with sodium bicarbonate (0.15 g) in water (30 cc) and the solution obtained is chromatographed on a column of DUOLITE S 861 resin (60 cc) (prepared as in Example 4), elution being carried out with a mixture of water and ethanol (90:10 by volume) and 15 cc fractions being collected. Fractions 3 to 32 are combined and lyophilized. The sodium salt of 3-[2-(4-acetamidophenyl)-thiazol-5-yl]-2-carboxy-8-oxo-7-[(thien-2-yl)-acetamido]-5-thia-1-azabicyclo[4.2.0]oct-2-ene (0.34 g) is obtained in the form of a pale yellow lyophilizate.

Proton nuclear magnetic resonance spectrum (350 MHz, $d_6$DMSO, δ in ppm, J in Hz): 2.07 (s, 3H, >N—CO—CH$_3$); 3.69 and 3.78 (2d, J=18, 2H, —S—CH$_2$—); 3.75 and 3.81 (2d, J=14, 2H, het—CH$_2$—CO—N<); 5.07 (d, J=5, 1H, —H in the 6-position); 5.52 (dd, J=9 and 5, 1H, —H in the 7-position); 6.93 to 6.97 (m, 2H, =CH—CH= of the thiophene); 7.36 (dd, J=5 and 1, 1H, =CH—S— of the thiophene); 7.71 (d, J=8, 2H, aromatic —H in the meta-positions to the thiazole); 7.77 (d, J=8, 2H, aromatic —H in the ortho-positions to the thiazole); 7.85 (s, 1H, —H of the thiazole); 9.11 (s, 1H, —CO—NH—); 10.5 (s, 1H, Ar—NH—CO—).

3-[2-(4-Acetamido-phenyl)-thiazol-5-yl]-2-benzhydryloxycarbonyl-7-t-butoxycarbonylamino-8-oxo-5-thia-1-azabicyclo[4.2.0]oct-2-ene can be prepared in the following manner:

Following the working method of Example 6, a mixture of the epimers of 2-benzhydryloxycarbonyl-3-(1-bromo-2-oxoethyl)-7-t-butoxycarbonylamino-8-oxo-5-thia-1-azabicyclo[4.2.0]oct-2-ene (8.16 g) is treated with para-acetamidothiobenzamide (2.7 g) prepared according to the method of L. STEPHENSON, W. K. WARBURTON and M. J. WILSON, J. Chem. Soc. (C), 861 (1969), in dry tetrahydrofuran (50 cc), and then with methanesulphonyl chloride (1.18 cc) and triethylamine (4.2 cc). The crude product is chromatographed on a column (height: 35 cm, diameter: 6 cm) of silica gel (0.04-0.06 mm), elution being carried out under a pressure of 0.5 bar (50 kPa) with a mixture of cyclohexane and ethyl acetate (40:60 by volume), and 100 cc fractions being collected. Fractions 28 to 36, containing the pure product, are combined and concentrated to dryness under reduced pressure (30 mm Hg; 4 kPa) at 30° C. A yellow froth (3.43 g) consisting principally of 3-[2-(4-acetamido-phenyl)-thiazol-5-yl]-2-benzhydryloxycarbonyl-7-t-butoxycarbonylamino-8-oxo-5-thia-1-azabicyclo[4.2.0]oct-2-ene is obtained.

Proton nuclear magnetic resonance spectrum (350 MHz, CDCl$_3$, δ in ppm, J in Hz): 1.47 (s, 9H, —C(CH$_3$)$_3$); 2.22 (s, 3H, >N—CO—CH$_3$); 3.61 and 3.75 (2d, J=18, 2H, —CH$_2$—S—); 5.09 (d, J=5, 1H, —H in the 6-position); 5.29 (d, J=9, 1H, —CO—NH—); 5.73 (dd, J=9 and 5, 1H, —H in the 7-position); 6.95 (s, 1H, —COO—CH(C$_6$H$_5$)$_2$); 7 to 7.45 (m, aromatic protons); 7.49 (s, 1H, —H of the thiazole), 7.59 (d, J=8, 2H, aromatic —H in the meta-positions to the thiazole); 7.70 (d, J=8, 2H, aromatic —H in the ortho-positions to the thiazole).

EXAMPLE 8

2-Benzhydryloxycarbonyl-7-t-butoxycarbonylamino-3-(2-methylthio-thiazol-5-yl)-8-oxo-5-thia-1-azabicyclo[4.2.0]oct-2-ene (4 g) dissolved in acetonitrile (40 cc) is treated, at 25° C., with methanesulphonic acid (4 cc), in accordance with the working method of Example 15. Crude 7-amino-2-benzhydryloxycarbonyl-3-(2-methylthio-thiazol-5-yl)-8-oxo-5-thia-1-azabicyclo[4.2.0]oct-2-ene (3.3 g) is obtained in the form of an orange oil.

Infra-red spectrum (CHBr$_3$): characteristic bands (cm$^{-1}$) at 3400, 3320, 1780, 1720, 1495, 1450, 1220, 760 and 755.

Crude 7-amino-2-benzhydryloxycarbonyl-3-(2-methylthiothiazol-5-yl)-8-oxo-5-thia-1-azabicyclo[4.2.0]oct-2-ene (3.3 g) is dissolved in tetrahydrofuran (30 cc) and is then acylated with (thien-2-yl)-acetyl chloride (0.83 cc) in the presence of triethylamine (0.94 cc) in accordance with the working method described in Example 1. The crude product obtained is chromatographed on a column (height: 30 cm; diameter: 4 cm) of silica gel (0.04-0.06 mm), elution being carried out under a pressure of 1 bar (100 kPa), with a 70:30 (by volume) mixture of cyclohexane and ethyl acetate, and 50 cc fractions being collected. Fractions 16 to 27, containing the pure product, are combined and concentrated to dryness under reduced pressure (30 mm Hg; 4 kPa) at 30° C., and the residue is triturated with isopropyl ether (30 cc). 2-Benzhydryloxycarbonyl-3-(2-methylthio-thiazol-5-yl)-8-oxo-7-(thien-2-yl-acetamido)-5-thia-1-azabicyclo[4.2.0]oct-2-ene (1.6 g) is obtained in the form of a yellow solid.

Infra-red spectrum (CHBr$_3$): characteristic bands (cm$^{-1}$) at 3400, 1785, 1720, 1680, 1620, 1505, 1450, 1430, 1220, 955 and 740.

Proton nuclear magnetic resonance spectrum (350 MHz, CDCl$_3$, δ in ppm, J in Hz): 2.56 (s, 3H, —S—CH$_3$); 3.46 and 3.65 (2d, J=18, 2H, —S—CH$_2$—); 3.86 (s, 2H, —CH$_2$—CO—N<); 5.05 (d, J=5, 1H, —H in the 6-position); 5.90 (dd, J=5 and 9, 1H, —H in the 7-position); 6.45 (d, J=9, 1H, —CO—NH—); 6.93 (s, 1H, —COO—CH(C$_6$H$_5$)$_2$); 6.98 to 7.05 (m, 2H, =CH—CH= of the thiophene); 7.10 to 7.5 (m, 2H, aromatic protons, —H of the thiazole =CH—S— of the thiophene).

A solution of aluminium chloride (1.04 g) in nitromethane (25 cc) is added in 10 minutes, to a solution, cooled to −8° C., of 2-benzhydryloxycarbonyl-3-(2-methylthiothiazol-5-yl)-8-oxo-7-(thien-2-yl-acetamido)-5-thia-1-azabicyclo[4.2.0]oct-2-ene (1.61 g) in dry methylene chloride (40 cc) containing anisole (4 cc), and the reaction mixture is stirred for 2 hours at a temperature of between −8° C. and 0° C. The reaction mixture is diluted with ethyl acetate (200 cc) and distilled water (200 cc) acidified with 4N hydrochloric acid (3 drops). After filtration to remove insoluble matter, the organic layer is decanted and is washed with distilled water (50 cc) and then extracted with a 5% strength sodium bicarbonate solution (80 cc). The aqueous solution is washed with ethyl acetate (50 cc) and then acidified to pH 3, at 0° C., with 4N hydrochloric acid. The precipitate is filtered off, washed with water (2×20 cc) and dried. 2-Carboxy-3-(2-methylthio-thiazol-5-yl)-8-oxo-7-(thien-2-yl-acetamido)-5-thia-1-azabicyclo[4.2.0]oct-2-ene (0.8 g) is obtained in the form of a white solid.

Infra-red spectrum (KBr): characteristic bands (cm$^{-1}$) at 3270, 3120-2200, 1780, 1725, 1650, 1540 and 705.

Proton nuclear magnetic resonance spectrum (350 MHz, $d_6$-DMSO, δ in ppm, J in Hz): 2.67 (s, 3H, —S—CH$_3$); 3.75 (limiting AB system, 2H, —CH$_2$—CO—N<); 3.81 (limiting AB system, 2H, —S—CH$_2$—); 5.18 (d, J=5, 1H, —H in the 6-position);

5.73 (dd, J=9 and 5, 1H, —H in the 7-position); 6.90 to 7 (m, 2H, =CH—CH= of the thiophene); 7.35 (dd, J=4 and 1, 1H, =CH—S— of the thiophene); 7.7 (s, 1H, —H of the thiazole); 9.18 (d, J=9, 1H, —CO—NH—).

2-Benzhydryloxycarbonyl-7-t-butoxycarbonylamino-3-(2-methylthio-thiazol-5-yl)-8-oxo-5-thia-1-azabicyclo[4.2.0]oct-2-ene can be prepared in the following manner:

A solution of methyl dithiocarbamate (9 g) in tetrahydrofuran (250 cc) is heated to the reflux temperature, and a solution of 2-benzhydryloxycarbonyl-3-(1-bromo-2-oxoethyl)-7-t-butoxycarbonylamino-8-oxo-5-thia-1-azabicyclo[4.2.0]oct-2-ene (44 g) in ethanol (100 cc) is then added. The reaction mixture is heated at 66° C. for 65 minutes and is then diluted with water (2 liters) and ethyl acetate (1 liter). The aqueous phase is decanted and washed with ethyl acetate (250 cc). The combined organic phases are washed with a half-saturated sodium chloride solution (1 liter), then dried over sodium sulphate, and concentrated to dryness under reduced pressure (30 mm Hg; 4 kPa) at 30° C. The residue is chromatographed on a column (diameter: 8 cm) of silica gel (0.2–0.06 mm) (1 liter), 500 cc fractions being collected. Elution is carried out successively with methylene chloride (3.5 liters) and with a 90:10 (by volume) mixture of methylene chloride and ethyl acetate (8 liters). Fractions 14 to 16, containing the pure product, are combined and concentrated to dryness under reduced pressure (30 mm Hg; 4 kPa) at 30° C. The residue is triturated with isopropyl ether and is then filtered off and dried; 2-benzhydryloxycarbonyl-7-t-butoxycarbonylamino-3-(2-methylthio-thiazol-5-yl)-8-oxo-5-thia-1-azabicyclo[4.2.0]oct-2-ene (7.3 g) is obtained in the form of a cream-coloured solid.

Infra-red spectrum (CHCl$_3$), characteristic bands (cm$^{-1}$) at 3440, 1790, 1720, 1505, 1455, 1390, 1370, 1155 and 695.

Proton nuclear magnetic resonance spectrum (350 MHz, CDCl$_3$, δ in ppm, J in Hz): 1.47 (s, 9H, —C(CH$_3$)$_3$); 2.56 (s, 3H, —S—CH$_3$); 3.50 and 3.68 (2d, J=18, 2H, —S—CH$_2$—); 5.06 (d, J=5, 1H, —H in the 6-position); 5.30 (d, J=9, 1H, —CO—NH—); 5.71 (dd, J=9 and 5, 1H, —H in the 7-position); 6.96 (s, 1H, —COO—CH(C$_6$H$_5$)$_2$); 7 to 7.60 (m, 11H, aromatic protons and —H of the thiazole).

EXAMPLE 9

Following the working method described in Example 15, 2-benzhydryloxycarbonyl-7-t-butoxycarbonylamino-3-(2-dimethylamino-thiazol-5-yl)-8-oxo-5-thia-1-azabicyclo[4.2.0oct-2-ene (5 g) is unblocked by means of methanesulphonic acid (5 cc) in acetonitrile (50 cc), and the crude 7-amino-2-benzhydryloxycarbonyl-3-(2-dimethylaminothiazol-5-yl)-8-oxo-5-thia-1-azabicyclo[4.2.0]oct-2-ene obtained (Rf=0.32; silica gel chromatographic plate; eluant: ethyl acetate) is then acylated with (thien-2-yl)-acetyl chloride (1.04 cc) in tetrahydrofuran (40 cc) in the presence of triethylamine (1.18 cc). Chromatography is then effected on a column (height: 30 cm; diameter: 5 cm) of silica gel (0.04–0.06 mm), elution being carried out under a pressure of 0.8 bar (80 kPa) with mixtures of cyclohexane and ethyl acetate (successively 50:50 by volume (3 liters) and 40:60 by volume (2 liters)), and 100 cc fractions being collected; fractions 33 to 44 are evaporated to dryness under reduced pressure (30 mm Hg; 4 kPa) at 30° C. 2-Benzhydryloxycarbonyl-3-(2-dimethylamino-thiazol-5-yl)-8-oxo-7-(thien-2-yl-acetamido)-5-thia-1-azabicyclo[4.2.0]oct-2-ene (2.4 g) is obtained in the form of a yellow solid.

Infra-red spectrum (CHBr$_3$): characteristic bands (cm$^{-1}$) at 3400, 3330, 1780, 1720, 1680, 1565, 1510, 1475, 1455, 1420, 1410, 755 and 740.

Proton nuclear magnetic resonance spectrum (350 MHz, CDCl$_3$, δ in ppm, J in Hz): 2.95 (s, 6H, —N(CH$_3$)$_2$); 3.47 and 3.54 (2d, J=18, 2H, —CH$_2$—S—); 3.95 (s, 2H, —CH$_2$—CO—N<); 5.03 (d, J=4.5, 1H, —H in the 6-position); 5.82 (dd, J=9 and 4.5, 1H, —H in the 7-position); 6.54 (d, J=9, 1H, —CO—NH—); 6.94 (s, 1H, —COO—CH(C$_6$H$_5$)$_2$); 6.95 to 7.05 (m, 2H, =CH—CH= of the thiophene); 7.03 (s, 1H, —H of the thiazole); 7.10 to 7.40 (m, 11H, aromatic protons and =CH—S— of the thiophene).

2-Benzhydryloxycarbonyl-3-(2-dimethylamino-thiazol-5-yl)-8-oxo-7-(thien-2-yl-acetamido)-5-thia-1-azabicyclo[4.2.0]oct-2-ene (2.4 g) is treated with formic acid (25 cc) in accordance with the working method described in Example 17, and 2-carboxy-3-(2-dimethylamino-thiazol-5-yl)-8-oxo-7-(thien-2-yl-acetamido)-5-thia-1-azabicyclo[4.2.0]oct-2-ene (1.05 g) is obtained, as the inner salt, in the form of a yellow solid.

Infra-red spectrum (KBr): characteristic bands (cm$^{-1}$) at 3280, 3100–2200, 1775, 1695, 1665, 1630, 1560, 1535, 1415, 1240 and 700.

Proton nuclear magnetic resonance spectrum (350 MHz, d$_6$-DMSO, δ in ppm, J in Hz): 3.04 (s, 6H, —N(CH$_3$)$_2$); 3.70 and 3.81 (2d, J=18, 2H, —CH$_2$—S—); 3.78 (s, 2H, —CH$_2$—CO—N<); 5.13 (d, J=4.5, 1H, —H in the 6-position); 5.63 (dd, J=4.5 and 8.5, 1H, —H in the 7-position); 6.90 to 7 (m, 2H, =CH—CH= of the thiophene); 7.30 (s, 1H, —H of the thiazole); 7.35 (dd, J=4 and 1, 1H, =CH—S— of the thiophene); 9.14 (d, J=8.5, 1H, —CO—NH—).

The working method of Example 2 is followed, but replacing the thiourea by N,N-dimethylthiourea (5.25 g) and starting with 2-benzhydryloxycarbonyl-7-t-butoxycarbonylamino-3-(2-dimethylamino-vinyl)-8-oxo-5-thia-1-azabicyclo[4.2.0]oct-2-ene (E-form) (21.4 g). The product obtained is chromatographed on a column (diameter: 4.5 cm) containing silica gel (0.2–0.06 mm)(500 cc), elution being carried out with methylene chloride (5 liters) and then with mixtures of methylene chloride and ethyl acetate, namely 99:1 by volume (5 liters) followed by 97:3 by volume (7.5 liters), and 500 cc fractions being collected; fractions 13 to 34 are concentrated to dryness under reduced pressure (30 mm Hg; 4 kPa) at 30° C. The residue is triturated with isopropyl ether (100 cc) and 2-benzhydryloxycarbonyl-7-t-butoxycarbonylamino-3-(2-dimethylamino-thiazol-5-yl)-8-oxo-5-thia-1-azabicyclo[4.2.0]oct-2-ene (13.8 g) is obtained in the form of a yellow solid.

Infra-red spectrum (CHBr$_3$): characteristic bands (cm$^{-1}$) at 3420, 1780, 1720, 1555, 1500, 1455, 1420, 1390, 1370, 1235, 760 and 740.

Proton nuclear magnetic resonance spectrum (350 MHz, CDCl$_3$, δ in ppm, J in Hz): 1.48 (s, 9H, —C(CH$_3$)$_3$); 2.95 (s, 6H, —N(CH$_3$)$_2$); 3.56 and 3.67 (2d, J=18, 2H, —CH$_2$—S—); 5.05 (d, J=4.5, 1H, —H in the 6-position); 5.27 (d, J=9, 1H, —CO—NH—); 5.64 (dd, J=4.5 and 9, 1H, —H in the 7-position); 6.97 (s, 1H, —COO—CH(C$_6$H$_5$)$_2$); 7.05 (s, 1H, —H of the thiazole); 7.15 to 7.45 (m, 10H, aromatic protons).

EXAMPLE 10

3-(2-Anilino-thiazol-5-yl)-2-benzhydryloxycarbonyl-7-t-butoxycarbonylamino-8-oxo-5-thia-1-azabicyclo[4.2.0]-oct-2-ene (2.3 g) is treated with methanesulphonic acid (2.3 cc) in acetonitrile (23 cc) in accordance with the working method described in Example 2. Crude 7-amino-3-(2-anilino-thiazol-5-yl)-2-benzhydryloxycarbonyl-8-oxo-5-thia-1-azabicyclo[4.2.0]oct-2-ene (1.85 g) is obtained and is acylated with (thien-2-yl)-acetyl chloride (0.445 cc) in tetrahydrofuran (25 cc) in the presence of triethylamine (0.505 cc), using the working method described in Example 1. The crude product obtained is chromatographed on a column (height: 30 cm; diameter: 2.5 cm) of silica gel (0.04–0.06 mm), elution being carried out under a pressure of 1.2 bar (120 kPa) with a 70:30 (by volume) mixture (3 liters) of cyclohexane and ethyl acetate, and 50 cc fractions being collected. Fractions 20 to 50 are combined and concentrated to dryness. After trituration with isopropyl ether, 3-(2-anilino-thiazol-5-yl)-2-benzhydryloxycarbonyl-8-oxo-7-(thien-2-yl-acetamido)-5-thia-1-azabicyclo[4.2.0]oct-2-ene (0.9 g) is obtained in the form of a yellow solid.

Infra-red spectrum (KBr): characteristic bands ($cm^{-1}$) at 3380, 1785, 1720, 1675, 1600, 1530, 1500, 1455, 750, 700, 620 and 605.

Proton nuclear magnetic resonance spectrum (350 MHz, $CDCl_3$, δ in ppm, J in Hz): 3.51 (limiting AB system, 2H, —S—$CH_2$—); 3.84 (s, 2H, —$CH_2$—CO—N<); 5.04 (d, J=4.5, 1H, —H in the 6-position); 5.84 (dd, J=4.5 and 9, 1H, —H in the 7-position); 6.92 (s, 1H, —COO—$CH(C_6H_5)_2$); 6.95 to 7.03 (m, 2H, =CH—CH= of the thiophene); 7.05 to 7.40 (m, 18H, aromatic protons, —H of the thiazole, =CH—S— of the thiophene and —CO—NH—); 8.65 (b, 1H, —NH—).

3-(2-Anilino-thiazol-5-yl)-2-benzhydryloxycarbonyl-8-oxo-7-(thien-2-yl-acetamido)-5-thia-1-azabicyclo[4.2.0]-oct-2-ene (0.9 g) is treated with formic acid (9 cc) in accordance with the working method described in Example 1, and 3-(2-anilino-thiazol-5-yl)-2-carboxy-8-oxo-7-(thien-2-yl-acetamido)-5-thia-1-azabicyclo[4.2.0]oct-2-ene (0.4 g) is obtained in the form of a yellow solid.

Infra-red spectrum (KBr): characteristic bands ($cm^{-1}$) at 3400, 3280, 3150–2000, 1770, 1665, 1625, 1605, 1530, 1500, 1455, 1400, 750 and 700.

Proton nuclear magnetic resonance spectrum (350 MHz, $d_6$-DMSO, δ in ppm, J in Hz): 3.79 (limiting AB system, 2H, —$CH_2$—CO—N<); 3.76 and 3.87 (2d, J=18, 2H, —S—$CH_2$—); 5.16 (d, J=5, 1H, —H in the 6-position); 5.68 (dd, J=5 and 9, 1H, —H in the 7-position); 6.85 to 7 (m, 2H, =CH—CH= of the thiophene); 7.20 to 7.4 (m, 5H, aromatic —H in the meta-positions and para-position of the anilino, =CH—S— of the thiophene and —H of the thiazole); 7.58 (d, J=7.5, 2H, aromatic —H in the ortho-positions of the anilino); 9.15 (d, J=9, 1H, —CO—NH—); 10.27 (s, broad, 1H, —NH—).

N-Phenylthiourea (3.34 g) is added to a solution of 2-benzhydryloxycarbonyl-7-t-butoxycarbonylamino-3-(1-chloro-2-oxoethyl)-8-oxo-5-thia-1-azabicyclo[4.2.0]oct-2-ene (a mixture of the epimers of the chloroaldehyde) (10.3 g) in a mixture of tetrahydrofuran (100 cc) and ethanol (40 cc), and the reaction mixture is then heated at the reflux temperature for 135 minutes. It is diluted with ethyl acetate (250 cc) and a half-saturated sodium bicarbonate solution (500 cc). The organic layer is washed with a half-saturated sodium chloride solution (250 cc) and then dried over magnesium sulphate and concentrated to dryness under reduced pressure (30 mm Hg; 4 kPa) at 30° C. The residue obtained is chromatographed on a column (height: 30 cm; diameter: 7 cm) of silica gel (0.04–0.06 mm), elution being carried out under a pressure of 0.7 bar (70 kPa) with a 70:30 (by volume) mixture of cyclohexane and ethyl acetate. After 1.5 liters of eluate have been collected, 100 cc fractions are collected and fractions 20 and 21 are combined and concentrated to dryness under reduced pressure (30 mm Hg; 4 kPa) at 30° C. The residue is triturated with isopropyl ether (30 cc). 3-(2-Anilino-thiazol-5-yl)-2-benzhydryloxycarbonyl-7-t-butoxycarbonylamino-8-oxo-5-thia-1-azabicyclo[4.2.0]oct-2-ene (2.7 g) is obtained in the form of a yellow solid.

Infra-red spectrum ($CHBr_3$): characteristic bands ($cm^{-1}$) at 3420, 1785, 1720, 1600, 1540, 1500, 1495, 1455, 1390, 1370 and 750.

Proton nuclear magnetic resonance spectrum (350 MHz, $CDCl_3$, δ in ppm, J in Hz): 1.47 (s, 9H, —$C(CH_3)_3$); 3.52 and 3.67 (2d, J=18, 2H, —S—$CH_2$—); 5.03 (d, J=4.5, 1H, —H in the 6-position); 5.41 (d, J=9, 1H, —CO—NH—); 5.66 (dd, J=4.5 and 9, 1H, —H in the 7-position); 6.95 (s, 1H, —COO—$CH(C_6H_5)_2$); 7.05 (s, 1H, —H of the thiazole); 7.05 to 7.4 (m, 15H, aromatic protons); 8.91 (s broad, 1H, —NH—).

On proceeding in a similar manner to Example 1, but treating a solution of 2-benzhydryloxycarbonyl-7-t-butoxycarbonylamino-3-(2-dimethylamino-vinyl)-8-oxo-5-thia-1-azabicyclo[4.2.0]oct-2-ene (E-form) (21.4 g) in dry tetrahydrofuran (100 cc), at −60° C., with a 10% strength (weight/volume) solution (40 cc) of chlorine in methylene chloride, 2-benzhydryloxycarbonyl-7-t-butoxycarbonylamino-3-(1-chloro-2-oxoethyl)-8-oxo-5-thia-1-azabicyclo[4.2.0]oct-2-ene (a mixture of the two epimers of the chloroaldehyde) (21.6 g) is obtained.

Infra-red spectrum ($CHBr_3$): characteristic bands ($cm^{-1}$) at 3420, 1785, 1720, 1505, 1450, 1390, 1365, 755 and 740.

Proton nuclear magnetic resonance spectrum (350 MHz, $CDCl_3$, δ in ppm, J in Hz):

epimer A 1.44 (s, 9H, $(CH_3)_3C$—); 3.46 and 3.60 (AB, J=18, 2H, —$SCH_2$—); 5.06 (d, J=5, 1H, H in the 6-position); 5.24 (d, J=9, 1H, —NH—); 5.67 (dd, J=5 and 9, 1H, H in the 7-position); 5.90 (s, 1H, —CHCl—); 6.96 (s, 1H, —$CHAr_2$); 7.20 to 7.60 (m, 10H, aromatic protons); 9.38 (s, 1H, —CHO).

epimer B 1.44 (s, 9H, $(CH_3)_3C$—); 3.23 and 3.63 (AB, J=18, 2H, —$SCH_2$—); 5.0 (d, J=5, 1H, H in the 6-position); 5.28 (d, J=9, 1H, —NH—); 5.71 (dd, J=5 and 9, 1H, H in the 7-position); 5.94 (s, 1H, —CHCl—); 6.91 (s, 1H, —$CHAr_2$); 7.20 to 7.60 (m, 10H, aromatic protons); 9.45 (s, 1H, —CHO).

EXAMPLE 11

Methanesulphonic acid (6 cc) is added to a solution of 2-benzhydryloxycarbonyl-7-t-butoxycarbonylamino-3-(2-methoxycarbonylamino-thiazol-5-yl)-8-oxo-5-thia-1-azabicyclo[4.2.0]oct-2-ene (6.2 g) in acetonitrile (60 cc). After 15 minutes at 20° C., the reaction mixture is diluted with methylene chloride (150 cc) and with a half-saturated sodium bicarbonate solution (200 cc). The aqueous layer is washed with methylene chloride (3×50 cc) and the combined organic phases are washed with distilled water (2×100 cc), dried over magnesium sulphate and concentrated to dryness under reduced pressure (30 mm Hg; 4 kPa) at 30° C. Crude 7-amino-2-benzhydryloxycarbonyl-3-(2-methoxycarbonylamino-thiazol-5-yl)-8-oxo-5-thia-1-azabicyclo[4.2.0]oct-2-ene (5.2 g) is obtained and is redissolved in dry tetrahydrofuran (50 cc). The solution obtained is cooled to 4° C. and treated with a solution of (thien-2-yl)-acetyl chloride (1.23 cc) in dry tetrahydrofuran (10 cc) and then with a solution of triethylamine (1.4 cc) in dry tetrahydrofuran (5 cc), in accordance with the working method described in Example 1. The crude product is chromatographed on a column (height: 32 cm, diameter: 6 cm) of silica gel (0.04–0.06 mm), elution being carried out under a pressure of 0.4 bar (40 kPa) with a 45.55 (by volume) mixture of cyclohexane and ethyl acetate, and 100 cc fractions being collected. Fractions 8 to 21, containing the pure product, are combined and concentrated to dryness under reduced pressure (30 mm Hg; 4 kPa) at 30° C. 2-Benzhydryloxycarbonyl-3-(2-methoxycarbonylamino-thiazol-5-yl)-8-oxo-7-(thien-2-yl-acetamido)-5-thia-1-azabicyclo[4.2.0]-oct-2-ene (1.91 g) is obtained in the form of a whitish solid.

Infra-red spectrum (CHBr$_3$): characteristic bands (cm$^{-1}$) at 3400, 3335, 3100–2500, 1780, 1730, 1690, 1545, 1515, 1500, 1460, 1430, 1255, 1240 and 705.

Proton nuclear magnetic resonance spectrum (350 MHz, CDCl$_3$, δ in ppm, J in Hz): 3.35 and 3.63 (2d, J=16, 2H, —S—CH$_2$—); 3.54 (s, 3H, —COO—CH$_3$); 3.85 (s, 2H, —CH$_2$—CO—); 5.00 (d, J=4, 1H, —H in the 6-position); 5.82 (dd, J=4 and 9, 1H, —H in the 7-position); 6.86 (s, 1H, —COO—C$\underline{H}$(C$_6$H$_5$)$_2$); 6.80 to 6.95 (m, 2H, =CH—CH= of the thiophene); 7.18 (d, J=4, =CH—S— of the thiophene); 7.20 to 7.60 (m, aromatic protons, —H of the thiazole, —CO—NH—);

12.98 (b smudged, 1H, —NH—C—O—).
$$\overset{\|}{\text{O}}$$

2-Benzhydryloxycarbonyl-3-(2-methoxycarbonylaminothiazol-5-yl)-8-oxo-7-(thien-2-yl-acetamido)-5-thia-1-azabicyclo[4.2.0]oct-2-ene (1.82 g) is treated with formic acid (20 cc) in accordance with the working method described in Example 1. 2-Carboxy-3-(2-methoxycarbonylaminothiazol-5-yl)-8-oxo-7-(thien-2-yl-acetamido)-5-thia-1-azabicyclo[4.2.0]oct-2-ene (0.9 g) is obtained in the form of a yellow solid.

Infra-red spectrum (KBr): characteristic bands (cm$^{-1}$) at 3400, 3260, 3100–2100, 1785, 1730, 1660, 1550, 1530, 1240 and 705.

Proton nuclear magnetic resonance spectrum (350 MHz, d$_6$-DMSO, δ in ppm, J in Hz):

3.77 (s, 3H, —C—O—CH$_3$);
$$\overset{\|}{\text{O}}$$

3.74 and 3.82 (2d, J=14, 2H, —CH$_2$—CO—); 3.79 and 3.89 (2d, J=16, 2H, —CH$_2$—S—); 5.17 (d, J=4, 1H, —H in the 6-position); 5.72 (dd, J=4 and 9, 1H, —H in the 7-position); 6.9 to 7.05 (m, 2H, =CH—CH= of the thiophene); 7.34 (dd, J=4 and 1, 1H, =CH—S— of the thiophene); 7.44 (s, 1H, —H of the thiazole); 9.17 (d, J=9, 1H, —CO—NH—);

11.35 (b, 1H, —COOH or —NH—C—O—);
$$\overset{\|}{\text{O}}$$

13.52 (b smudged, 1H, —NH—C—O— or —COOH).
$$\overset{\|}{\text{O}}$$

3-(2-Amino-thiazol-5-yl)-2-benzhydryloxycarbonyl-7-t-butoxycarbonylamino-8-oxo-5-thia-1-azabicyclo[4.2.0]-oct-2-ene (1.13 g) is treated in accordance with the working method described in Example 1 (B), the acetyl chloride being replaced by methyl chloroformate (0.19 cc). The crude product obtained is chromatographed on a column (height: 30 cm, diameter: 3 cm) of silica gel (0.04–0.06 mm), elution being carried out under a pressure of 0.4 bar (40 kPa) with a 40:60 (by volume) mixture of cyclohexane and ethyl acetate; 50 cc fractions are collected and are analysed by chromatography on a thin layer of silica gel (eluant: a 40:60 (by volume) mixture of cyclohexane and ethyl acetate). The fractions containing the pure expected product (Rf=0.3) are combined and concentrated to dryness under reduced pressure (30 mm Hg; 4 kPa) at 30° C. 2-Benzhydryloxycarbonyl-7-t-butoxycarbonylamino-3-(2-methoxycarbonylamino-thiazol-5-yl)-8-oxo-5-thia-1-azabicyclo[4.2.0]oct-2-ene (0.73 g) is obtained in the form of a yellow froth.

Infra-red spectrum (CHBr$_3$): characteristic bands (cm$^{-1}$) at 3420, 3100–2500, 1785, 1725, 1720, 1575, 1500, 1455 1430, 1390, 1370, 1240, 760, 745 and 605.

Proton nuclear magnetic resonance spectrum (350 MHz, CDCl$_3$, δ in ppm, J in Hz): 1.48 (s, 9H, —C(CH$_3$)$_3$); 3.57 and 3.72 (2d, J=18, 2H, —S—CH$_2$—);

3.86 (s, 3H, —C—O—CH$_3$);
$$\overset{\|}{\text{O}}$$

5.08 (d, J=5, 1H, —H in the 6-position); 5.37 (d, J=9, 1H, —CO—NH—); 5.71 (dd, J=5 and 9, 1H, —H in the 7-position); 6.93 (s, 1H, —COO—C$\underline{H}$(C$_6$H$_5$)$_2$); 7.07 (s, —H of the thiazole); 7.05 to 7.40 (m, aromatic protons);

11.26 (b, 1H, —NH—C—O—).
$$\overset{\|}{\text{O}}$$

EXAMPLE 12

Following the working method described in Example 15, 2-benzhydryloxycarbonyl-7-t-butoxycarbonylamino-3-(2-dimethylaminomethyleneamino-thiazol-5-yl)-8-oxo-5-thia-1-azabicyclo[4.2.0]oct-2-ene (E-form) (0.77 g) is treated with methanesulphonic acid (0.8 cc) in acetonitrile (8 cc). 7-Amino-2-benzhydryloxycarbonyl-3-(2-dimethylaminomethyleneamino-thiazol-5-yl)-8-oxo-5-thia-1-azabicyclo[4.2.0]oct-2-ene (E-form) (0.65 g) is obtained in the form of a crude brown froth (Rf=0.1, silica gel chromatographic plate; eluant: ethyl acetate), and this is redissolved in tetrahydrofuran (15 cc) and acylated, in accordance with the working method described in Example 1, with (thien-2-yl)acetyl chloride (0.15 cc) in the presence of triethylamine (0.17 cc). Chromatography is effected on a column (height: 28 cm; diameter: 2 cm) of silica gel (0.04-0.06 mm), elution being carried out under a pressure of 0.8 bar (80 kPa) by means of ethyl acetate, and 30 cc fractions being collected. Fractions 11 to 19, containing the pure product, are combined and concentrated to dryness under reduced pressure (30 mm Hg; 4 kPa) at 30° C. 2-Benzhydryloxycarbonyl-3-(2-dimethylaminomethyleneamino-thiazol-5-yl)-8-oxo-7-(thien-2-yl-acetamido)-5-thia-1-azabicyclo[4.2.0]-oct-2-ene (E-form) (0.13 g) is obtained in the form of a yellow powder.

Infra-red spectrum (CHBr$_3$): characteristic bands (cm$^{-1}$) at 3400, 1780, 1720, 1680, 1615, 1505, 1490 and 1450.

Proton nuclear magnetic resonance spectrum (350 MHz, CDCl$_3$, δ in ppm, J in Hz): 3.08 and 3.11 (2s, 6H, —N(CH$_3$)$_2$); 3.51 and 3.65 (2d, J=18, 2H, —CH$_2$—S—); 3.86 (s, 2H, —CH$_2$—CO—N<); 5.04 (d, J=4.5, 1H, —H in the 6-position); 5.87 (dd, J=9 and 4.5, 1H, —H in the 7-position); 6.38 (d, J=9, 1H, —CO—NH—); 6.93 (s, 1H, —COOCH(C$_6$H$_5$)); 6.97 to 7.03 (m, 2H, =CH—CH= of the thiophene); 7.03 (s, 1H, —H of the thiazole); 7.1 to 7.4 (m, aromatic protons); 7.95 (s, 1H, —N=CH—N<).

Following the working method described in Example 1, 2-benzhydryloxycarbonyl-3-(2-dimethylaminomethylene-amino-thiazol-5-yl)-8-oxo-7-(thien-2-yl-acetamido)-5-thia-1-azabicyclo[4.2.0]oct-2-ene (0.1 g) is treated with formic acid (15 cc). 2-Carboxy-3-(2-dimethylaminomethyleneaminothiazol-5-yl)-8-oxo-7-(thien-2-yl-acetamido)-5-thia-1-azabicyclo[4.2.0]oct-2-ene (0.045 g) is obtained in the form of a yellow powder.

Infra-red spectrum (KBr): characteristic bands (cm$^{-1}$) at 3260, 3100-2000, 1770, 1680, 1630, 1530, 1390 and 700.

Proton nuclear magnetic resonance spectrum (350 MHz, d$_6$-DMSO, δ in ppm, J in Hz): 2.97 and 3.12 (2s, 6H, —N(CH$_3$)$_2$); 3.65 to 3.85 (b, 4H, —CH$_2$—S— and —CH$_2$—CO—N<); 5.12 (d, J=4.5, 1H, —H in the 6-position); 5.67 (dd, J=4.5 and 9, 1H, —H in the 7-position); 6.9 to 7 (m, 2H, =CH—CH= of the thiophene); 7.3 to 7.45 (m, 2H, =CH—S— of the thiophene and —H of the thiazole); 8.27 (s, 1H, —N=CH—N<); 9.15 (d, J=9, 1H, —CO—NH—).

2-Benzhydryloxycarbonyl-7-t-butoxycarbonylamino-3-(2-dimethylaminomethyleneamino-thiazol-5-yl)-8-oxo-5-thia-1-azabicyclo[4.2.0]oct-2-ene can be prepared in in accordance with either of the following methods:

A. A solution of crude 2-benzhydryloxycarbonyl-3-(1-bromo-2-oxoethyl)-7-t-butoxycarbonylamino-8-oxo-5-thia-1-azabicyclo[4.2.0]oct-2-ene in tetrahydrofuran (50 cc) is prepared by treating, in accordance with the working method described in Example 2, 2-benzhydryloxycarbonyl-7-t-butoxycarbonylamino-3-(2-dimethylamino-vinyl)-8-oxo-5-thia-1-azabicyclo[4.2.0]oct-2-ene (13.4 g) with bromine (1.3 cc) dissolved in methylene chloride (5 cc), and then with water (0.99 cc). A solution of dimethylaminomethylenethiourea (3.28 g) in a mixture of distilled water (10 cc) and tetrahydrofuran (50 cc) is added at −40° C., and the reaction mixture is then stirred for 3 hours, whilst allowing the temperature to rise to 15° C. The reaction mixture is diluted with ethyl acetate (600 cc) and is washed with water (800 cc) to which a saturated sodium bicarbonate solution (100 cc) has been added, and then with distilled water (3×200 cc) and with a saturated sodium chloride solution (200 cc). After having been dried over magnesium sulphate, the organic phase is concentrated to dryness under reduced pressure (30 mm Hg; 4 kPa) at 30° C. and the residue is chromatographed on a column (height: 30 cm, diameter: 5 cm) of silica gel (0.04-0.06 mm), elution being carried out under a pressure of 0.6 bar (60 kPa) with ethyl acetate, and 70 cc fractions being collected. Fractions 19 to 30, containing the pure product, are combined and concentrated to dryness under reduced pressure (30 mm Hg; 4 kPa) at 30° C. 2-Benzhydryloxycarbonyl-7-t-butoxycarbonylamino-3-(2-dimethylaminomethyleneamino-thiazol-5-yl)-8-oxo-5-thia-1-azabicyclo[4.2.0]oct-2-ene (0.78 g) is obtained in the form of an orange froth.

Infra-red spectrum (CHCl$_3$): characteristic bands (cm$^{-1}$) at 3440, 1770, 1725, 1625, 1500, 1460, 1375, 1160 and 700.

Proton nuclear magnetic resonance spectrum (350 MHz, CDCl$_3$, δ in ppm, J in Hz): 1.47 (s, 9H, —C(CH$_3$)$_3$); 3.08 and 3.13 (2s, 6H, —N(CH$_3$)$_2$); 3.58 and 3.71 (2d, J=18, 2H, —S—CH$_2$—); 5.06 (d, J=4.5, 1H, —H in the 6-position); 5.27 (d, J=9, 1H, —CO—NH—); 5.67 (dd, J=9 and 4.5, 1H, —H in the 7-position); 6.95 (s, 1H, —COO—CH(C$_6$H$_5$)$_2$); 7.07 (s, 1H, —H of the thiazole); 7.10 to 7.50 (m, aromatic protons); 7.95 (s, 1H, —N=CH—N<).

B. A solution of 3-(2-amino-thiazol-5-yl)-2-benzhydryloxycarbonyl-7-t-butoxycarbonylamino-8-oxo-5-thia-1-azabicyclo[4.2.0]oct-2-ene (4 g) in tetrahydrofuran (50 cc) is treated with dimethoxy(dimethylamino)methane (1.13 g). The reaction mixture is stirred for 25 minutes at 20° C., then diluted with ethyl acetate (150 cc), washed with distilled water (4×150 cc) and with a saturated sodium chloride solution (150 cc) and dried ove magnesium sulphate. The residue obtained after evaporation of the solvent under reduced pressure (30 mm Hg; 4 kPa) at 30° C. is chromatographed on a column (height: 28 cm; diameter: 5 cm) of silica gel (0.04-0.06 mm), elution being carried out under a pressure of 0.6 bar (60 kPa) with ethyl acetate, and 100 cc fractions being collected. Fractions 9 to 23, containing the pure product, are combined and concentrated to dryness under reduced pressure (30 mm Hg; 4 kPa) at 30° C. 2-Benzhydryloxycarbonyl-7-t-butoxycarbonylamino-3-(2-dimethylaminomethyleneamino-thiazol-5-yl)-8-oxo-5-thia-1-azabicyclo[4.2.0]oct-2-ene (E-form) (2.25 g) is obtained in the form of an orange froth whose characteristics are identical to those of the product obtained in A.

EXAMPLE 13

On treating 2-benzhydryloxycarbonyl-7-t-butoxycarbonylamino-3-(2-isopropylidenehydrazo-thiazol-5-yl)-8-oxo-5-thia-1-azabicyclo[4.2.0]oct-2-ene (4.6 g) with methanesulphonic acid (4.5 cc) in acetonitrile (40 cc) in accordance with the working method described in Example 15, crude 7-amino-2-benzhydryloxycarbonyl-3-(2-isopropylidenehydrazo-thiazol-5-yl)-8-oxo-5-thia-1-azabicyclo[4.2.0]oct-2-ene (3.8 g) is obtained, and this is acylated with (thien-2-yl)-acetyl chloride (0.91 cc) in accordance with the working method described in Example 1. The crude product is chromatographed on a column (height: 35 cm, diameter: 5 cm) of silica gel (0.04-0.06 mm), elution being carried out under a pressure of 0.5 bar (50 kPa) with a mixture (50:50 by volume) of cyclohexane and ethyl acetate, and 90 cc fractions being collected. Fractions 23 to 29, containing the pure product, are combined and concentrated to dryness under reduced pressure (30 mm Hg; 4 kPa) at 30°

C. 2-Benzhydryloxycarbonyl-3-(2-isopropylidenehydrazo-thiazol-5-yl)-8-oxo-7-[(thien-2-yl)-acetamido]-5-thia-1-azabicyclo[4.2.0]oct-2-ene (0.78 g) is obtained in the form of a yellow froth.

Infra-red spectrum (CHCl3): characteristic bands (cm⁻¹) at 3400, 3320, 3160, 3100–2500, 1780, 1720, 1680, 1545, 1510 and 695.

Proton nuclear magnetic resonance spectrum (350 MHz, CDCl3, δ in ppm, J in Hz): 1.85 and 2.05

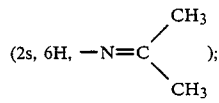

3.50 (b, 2H, —S—CH2—); 3.85 (s, 2H, het-CH2—CO—N<); 5.04 (d, J=4.5, 1H, —H in the 6-position); 5.84 (dd, J=4.5 and 9.5, 1H, —H in the 7-position); 6.93 (s, —COO—CH(C6H5)2); 6.9 to 7 (m, =CH—CH= of the thiophene); 6.9 to 7.4 (m, aromatic protons, —H of the thiazole, =CH—S— of the thiophene, —CO—NH— in the 7-position and —NH—N=).

Following the working method of Example 1, 2-benzhydryloxycarbonyl-3-(2-isopropylidenehydrazo-thiazol-5-yl)-8-oxo-7-[(thien-2-yl)-acetamido]-5-thia-1-azabicyclo[4.2.0]oct-2-ene (0.73 g) is treated with 90% strength formic acid (20 cc) and 2-carboxy-3-(2-isopropylidenehydrazo-thiazol-5-yl)-8-oxo-7-[(thien-2-yl)-acetamido]-5-thia-1-azabicyclo[4.2.0]oct-2-ene (0.28 g) is obtained in the form of a brown solid.

Infra-red spectrum (KBr): characteristic bands (cm⁻¹) at 3260, 1770, 1650, 1615, 1530, 1370 and 700.

Proton nulcear magnetic resonance spectrum (350 MHz, d6-DMSO, δ in ppm, J in Hz): 1.90 and 1.95

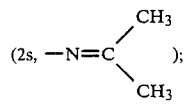

3.71 and 3.84 (2d, J=18, 2H, —S—CH2—); 3.78 (s, 2H, het—CH2—CO—N<); 5.13 (d, J=4.5, 1H, —H in the 6-position); 5.65 (b, 1H, —H in the 7-position); 6.93 to 7 (m, 2H, =CH—CH= of the thiophene); 7.28 to 7.4 (m, 3H, =CH—S— of the thiophene, —H of the thiazole, —NH—N=); 9.15 (d, J=9, 1H, —CO—NH— in the 7-position).

2-Benzhydryloxycarbonyl-7-t-butoxycarbonylamino-3-(2-isopropylidenehydrazo-thiazol-5-yl)-8-oxo-5-thia-1-azabicyclo[4.2.0]oct-2-ene can be obtained in the following manner:

Following the working method of Example 2, but replacing the thiourea by acetone thiosemicarbazide (3.28 g), 2-benzhydryloxycarbonyl-7-t-butoxycarbonylamino-3-(2-dimethylamino-vinyl)-8-oxo-5-thia-1-azabicyclo[4.2.0]oct-2-ene (E-form) (13.4 g) is treated and the product chromatographed on a column (height: 35 cm, diameter: 4 cm) of silica gel (0.06–0.2 mm), elution being carried out with a mixture (50:50 by volume) of cyclohexane and ethyl acetate, and 100 cc fractions being collected. Fractions 11 to 17, containing the pure product, are combined and concentrated to dryness under reduced pressure (30 mm Hg; 4 kPa) at 30° C. 2-Benzhydryloxycarbonyl-7-t-butoxycarbonylamino-3-(2-isopropylidenehydrazo-thiazol-5-yl)-8-oxo-5-thia-1-azabicyclo[4.2.0]oct-2-ene (4.73 g) is obtained in the form of a beige froth.

Infra-red spectrum (CHCl3): characteristic bands (cm⁻¹) at 3440, 3360, 3160, 1780, 1720, 1550, 1505, 1455, 1390, 1370, 1160 and 700.

Proton nuclear magnetic resonance spectrum (350 MHz, CDCl3, δ in ppm, J in Hz): 1.48 (s, 9H, —C(CH3)3); 1.83 and 2.04

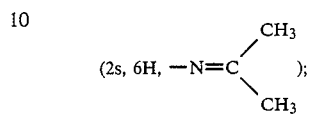

3.53 and 3.67 (2d, J=18, 2H, —S—CH2—); 5.03 (d, J=4.5, 1H, —H in the 6-position); 5.41 (d, J=9, 1H, —CO—NH— in the 7-position); 5.66 (dd, J=4.5 and 9, 1H, —H in the 7-position); 6.92 (s, 1H, —COO—CH(C6H5)2); 6.96 (s, 1H, —H of the thiazole); 7.1 to 7.4 (m, aromatic protons+—NH—N=).

EXAMPLE 14

3-(2-Acetamido-thiazol-5-yl)-7-amino-2-benzhydryloxycarbonyl-8-oxo-5-thia-1-azabicyclo[4.2.0]oct-2-ene (obtained as described in Example 1) (3.4 g) is acylated with (1,3-dithiol-2-on-4-yl)-acetyl chloride (1.95 g) in dry tetrahydrofuran (75 cc) in the presence of triethylamine (1.4 cc), using the working method described in Example 1. The crude product is chromatographed on a column (height: 30 cm; diameter: 6 cm) of silica gel (0.04–0.06 mm), elution being carried out under a pressure of 0.4 bar (40 kPa) with a mixture (20:80 by volume) of cyclohexane and ethyl acetate, and 100 cc fractions being collected. Fractions 11 to 20 are combined and concentrated to dryness under reduced pressure (30 mm Hg; 4 kPa) at 30° C. The expected product (1.87 g) is obtained and is crystallised from acetonitrile (90 cc). 3-(2-Acetamidothiazol-5-yl)-2-benzhydryloxycarbonyl-7-(1,3-dithiol-2-on-4-yl-acetamido)-8-oxo-5-thia-1-azabicyclo[4.2.0]oct-2-ene (0.8 g) is obtained in the form of white crystals.

Infra-red spectrum (KBr): characteristic bands (cm⁻¹) at 3280, 1780, 1730, 1695, 1640, 1545, 1225 and 700.

Proton nuclear magnetic resonance spectrum (350 MHz, d6-DMSO, δ in ppm, J in Hz): 2.14 (s, 3H, —CO—CH3); 3.67 (s, 2H, —CH2—CO—N<); 3.79 and 3.92 (2d, J=18, 2H, —CH2—S—); 5.23 (d, J=4.5, 1H, —H in the 6-position); 5.8 (dd, J=4.5 and 9, 1H, —H in the 7-position); 6.83 (s, 1H, —COOCH(C6H5)2); 7.01 (s, 1H, —S—CH=); 7.03 to 7.4 (m, 11H, aromatic protons and —H of the thiazole); 9.3 (d, J=9, 1H, —CO—NH—); 12.06 (s, 1H, —NH—CO—CH3).

Following the working method described in Example 2, but starting from 3-(2-acetamido-thiazol-5-yl)-2-benzhydryloxycarbonyl-7-(1,3-dithiol-2-on-4-yl-acetamido)-8-oxo-5-thia-1-azabicyclo[4.2.0]oct-2-ene (0.8 g), 3-(2-acetamido-thiazol-5-yl)-2-carboxy-7-(1,3-dithiol-2-on-4-ylacetamido)-8-oxo-5-thia-1-azabicyclo[4.2.0]oct-2-ene (0.2 g) is obtained in the form of a beige solid.

Infra-red spectrum (KBr): characteristic bands (cm⁻) at 3270, 3100 to 2100, 1785, 1685, 1640 and 1545.

Proton nuclear magnetic resonance spectrum (350 MHz, d6-DMSO, δ in ppm, J in Hz): 2.14 (s, 3H, —CO—CH3); 3.65 (s, 2H, —CH2—CO—N<); 3.77 and 3.91 (2d, J=18, 2H, —CH2—S—); 5.18 (d, J=5, 1H, —H in the 6-position); 5.68 (dd, J=5 and 9, 1H, —H in the 7-position); 7.01 (s, 1H, —S—CH=); 7.52 (s, 1H, H of the thiazole); 9.27 (d, J=9, 1H, —CO—NH—); 12.15 (s broad, 1H, —NH—CO—CH$_3$).

EXAMPLE 15

A solution of 3-(2-acetamido-thiazol-5-yl)-2-benzhydryloxycarbonyl-7-t-butoxycarbonylamino-8-oxo-5-thia-1-azabicyclo[4.2.0]oct-2-ene (6.06 g) in acetonitrile (100 cc) is stirred with methanesulphonic acid (6 cc) for 30 minutes at 20° C., then diluted with ethyl acetate (200 cc) and stirred with a saturated sodium bicarbonate solution (300 cc). The aqueous layer is extracted with ethyl acetate (100 cc) and the combined organic solutions are washed with a half-saturated sodium chloride solution (2×250 cc), then dried over magnesium sulphate, and concentrated to dryness under reduced pressure (30 mm Hg; 4 kPa) at 40° C. 3-(2-Acetamido-thiazol-5-yl)-7-amino-2-benzhydryloxycarbonyl-8-oxo-5-thia-1-azabicyclo[4.2.0]oct-2-ene (4.9 g) is obtained in the form of a yellow froth. This product is redissolved in dry tetrahydrofuran (75 cc). The solution, cooled to about 0° C, is treated successively with phenylacetyl chloride (1.54 g) and triethylamine (1.4 cc) and then stirred for 1 hour at between 0° and 4° C. The reaction mixture is diluted with ethyl acetate (100 cc) and a half-saturated sodium bicarbonate solution (200 cc). The organic layer is decanted, washed with water (100 cc) and then with a half-saturated sodium chloride solution (100 cc), dried over magnesium sulphate and concentrated to dryness under reduced pressure (30 mm Hg; 4 kPa) at 40° C. The residue is taken up in methylene chloride (25 cc). The precipitate is filtered off and then taken up in boiling acetonitrile (80 cc). After the mixture has cooled, the precipitate is filtered off, washed with acetonitrile (10 cc) and dried under reduced pressure (2 mm Hg; 0.27 kPa) at 25° C. 3-(2-Acetamido-thiazol-5-yl)-2-benzhydryloxycarbonyl-8-oxo-7-phenylacetamido-5-thia-1-azabicyclo[4.2.0]oct-2-ene (2.65 g) is thus obtained in the form of a white solid.

Infra-red spectrum (KBr): characteristic bands (cm$^{-1}$) at 3410, 3370, 3170, 1780, 1730, 1720, 1700, 1680, 1655, 1540, 1525, 1515, 1495, 1455, 1230, 760, 740 and 700.

Proton nuclear magnetic resonance spectrum (350 MHz, CDCl$_3$/d$_6$-DMSO, δ in ppm, J in Hz): 2.25 (s, 3H, >N—CO—CH$_3$); 3.57 and 3.68 (2d, J=14, 2H, —CH$_2$CO N<); 3.63 and 3.75 (2d, J=18, 2H, —CH$_2$—S—); 5.14 (d, J=4.5, 1H, —H in the 6-position); 5.84 (dd, J=4.5 and 9, 1H, —H in the 7-position); 6.88 (s, 1H, —COO—CH(C$_6$H$_5$)$_2$); 7.12 (s, 1H, —H of the thiazole); 7 to 7.5 (m, 15H, aromatic protons); 9.08 (d, J=9, 1H, —CO—NH—); 11.95 (s broad, 1H, —NH—CO—CH$_3$).

Using a method similar to Example 1, 3-(2-acetamido-thiazol-5-yl)-2-benzhydryloxycarbonyl-8-oxo-7-phenylacetamido-5-thia-1-azabicyclo[4.2.0]oct-2-ene (2.65 g) is treated and the corresponding acid (1.7 g) is obtained. This acid is purified as follows: the product is dissolved in a 5% strength sodium bicarbonate solution. The aqueous solution is washed with ethyl acetate and then acidified to pH 4 with 1N hydrochloric acid. The precipitate is filtered off, washed with water (10 cc), ethanol (10 cc) and ethyl ether (10 cc), and dried. 3-(2-Acetamido-thiazol-5-yl)-2-carboxy-8-oxo-7-phenylacetamido-5-thia-1-azabicyclo[4.2.0]oct-2-ene (1.55 g) is thus obtained in the form of a white solid.

Infra-red spectrum (KBr): characteristic bands (cm$^{-1}$) at 3280, 3200, 3100–2300, 1785, 1710, 1695, 1650, 1540, 1520, 1495 and 1450.

Proton nuclear magnetic resonance spectrum (350 MHz, d$_6$-DMSO, δ in ppm, J in Hz): 2.18 (s, 3H, <N—CO—CH$_3$); 3.53 and 3.63 (2d, J=14, 2H, —CH$_2$—CO—N<); 3.78 and 3.93 (2d, J=18, 2H, —CH$_2$—S—); 5.17 (d, J=4.5, 1H, —H in the 6-position); 5.74 (dd, J=4.5 and 8, 1H, —H in the 7-position); 7.15 to 7.45 (m, 5H, aromatic protons); 7.52 (s, 1H, —H of the thiazole); 9.17 (d, J=9, 1H, —CO—NH—); 12.19 (s broad, 1H, —NH—CO—CH$_3$); 13.54 (b, 1H, —COOH).

Following the working method of Example 1, 3-(2-acetamido-thiazol-5-yl)-2-carboxy-8-oxo-7-phenylacetamido-5-thia-1-azabicyclo[4.2.0]oct-2-ene (1.1 g) is dissolved in a solution of sodium bicarbonate (0.25 g) and distilled water (100 cc) and chromatographed on a column (diameter: 1.8 cm, height: 27 cm) of DUOLITE S 841 resin (washed beforehand as described in Example 4), elution being carried out with distilled water (300 cc) and then with mixtures of water and ethanol in the following ratios by volume: 95:5 (200 cc), 90:10 (200 cc), 80:20 (200 cc) and 60:40 (200 cc); 50 cc fractions are collected. Fractions 8 to 20 are combined and lyophilized after having evaporated the alcohol under reduced pressure (30 mm Hg; 4 kPa) at 30° C. The sodium salt of 3-(2-acetamido-thiazol-5-yl)-2-carboxy-8-oxo-7-phenylacetamido-5-thia-1-azabicyclo[4.2.0]oct-2-ene (1.1 g) is obtained in the form of a white lyophilizate.

Infra-red spectrum (KBr): characteristic bands (cm$^{-1}$) at 3400–2500, 1760, 1670, 1605, 1550, 1395, 1370, 1305 and 1010.

Proton nuclear magnetic resonance spectrum (350 MHz, d$_6$-DMSO, δ in ppm, J in Hz): 2.11 (s, 3H, CH$_3$CO—); 3.50 and 3.59 (2d, J=14, 2H, C$_6$H$_5$CH$_2$CO—); 3.59 and 3.70 (2d, J=16, 2H, —SCH$_2$—); 5.02 (d, J=5, 1H, H in the 6-position); 5.50 (dd, J=9 and 5, 1H, H in the 7-position); 7.20 to 7.35 (m, 5H, phenyl); 7.46 (s, 1H, H in the 4-position of the thiazole); 9.07 (d, J=9, 1H,—CON$\underline{H}$—C$_7$); 11.90 (s broad, 1H, CH$_3$CON$\underline{H}$—).

EXAMPLE 16

Triethylamine (0.65 cc) is added to a solution, cooled to 3° C. of 7-amino-2-benzyhydryloxycarbonyl-3-[2-(2-dimethylamino-ethylamino)-thiazol-5-yl]-8-oxo-5-thia-1-azabicyclo[4.2.0]oct-2-ene (2.6 g) in dry methylene chloride (60 cc). A solution of (3,4-dichlorophenyl)-thioacetyl chloride (1.2 g) in methylene chloride (20 cc) is added dropwise to the mixture obtained. When all has been added, the mixture is stirred at 23° C. for 2 hours 30 minutes. Thereafter, the reaction mixture is diluted with methylene chloride (250 cc) and the organic phase is then washed successively with distilled water (200 cc), a saturated sodium bicarbonate solution (200 cc) and a saturated sodium chloride solution (200 cc). The organic phase is dried over anhydrous magnesium sulphate, filtered and concentrated to dryness under reduced pressure (30 mm Hg; 4 kPa). The residue is purified by chromatography on silica gel (height of the silica layer 18 cm, column diameter 3 cm) (0.04–0.06 mm), elution being carried out under a pressure of 50 KPa with a mixture of methylene chloride and methanol (90:10 by volume), and 30 cc fractions being collected. Fractions 11 to 17, containing the product, are combined and concentrated to dryness under reduced pressure (30 mm Hg; 4 kPa) at 30° C. 2-Benzhydryloxycarbonyl-7-(3,4-dichloro-phenylthio)-acetamido-3-[2-(2-dimethylamino-ethylamino)-thiazol-5-yl]-8-oxo-5-thia-1-azabicyclo[4.2.0]oct-2-ene (1.5 g) is obtained in the form of a yellow froth.

Proton nuclear magnetic resonance spectrum (250 MHz, CDCl₃, δ in ppm, J in Hz); 2.33 (s, 6H, —N(CH₃)₂); 2.60 (t, J=6, 2H, >N—CH₂—); 3.24 (m, 2H, —NH—CH₂—); 3.46 and 3.59 (2d, J=18, 2H, —S—CH₂—); 3.6 and 3.75

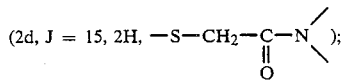

(2d, J = 15, 2H, —S—CH₂—C—N⟨ );
                        ‖
                        O 5.03 (d, J=5, 1H, —H in the 6-position); 5.78 (dd, J=9 and 5, 1H, —H in the 7-position); 6.09 (b, 1H, >NH); 6.96 (s, 1H, —H of the thiazole or —COO—CH(C₆H₅)₂); 6.97 (s, 1H, —COO—CH(C₆H₅)₂ or —H of the thiazole); 7.10 to 7.35 (m, aromatic proton and aromatic —H in the 6-position); 7.39 (d, J=8.5, 1H, aromatic —H in the 5-position); 7.45 (d, J=2, 1H, aromatic —H in the 2-position);

7.47 (d, J = 9, 1H, —NH—C=O).
                          |

A mixture of 2-benzhydryloxycarbonyl-7-(3,4-dichlorophenylthio)-acetamido-3-[2-(2-dimethylamino-ethylamino)-thiazol-5-yl]-8-oxo-5-thia-1-azabicyclo[4.2.0]oct-2ene (1.5 g), anisole (5 cc) and formic acid (25 cc) is stirred for 30 minutes at 50° C. The mixture is concentrated to dryness under reduced pressure (0.1 mm Hg; 0.013 kPa) and the residue is then taken up in ethanol (3×50 cc) and concentrated to dryness under reduced pressure (30 mm Hg; 4 kPa) at 30° C. The solid obtained is washed with acetone (50 cc) and then with ethyl ether (50 cc). It is dried under reduced pressure (0.1 mm Hg; 0.013 kPa), giving 2-carboxy-7-(3,4-dichloro-phenylthio)-acetamido-3-[2-(2-dimethylamino-ethylamino)-thiazol-5-yl]-8-oxo-5-thia-1-azabicyclo[4.2.0]oct-2-ene (1 g) in the form of a yellow powder.

Infra-red spectrum (KBr): characteristic bands (cm⁻¹) at 3260, 1765, 1675, 1605, 1530, 1460, 1380 and 815.

Proton nuclear magnetic resonance spectrum (250 MHz, d₆-DMSO, δ in ppm, J in Hz): 2.69 (s, 6H, —N(CH₃)₂); 3.15 (b, =N—CH₂—); 3.52 (b, —NH—CH₂—); 3.62 and 3.88 (2d, J=18, 2H, —S—CH₂—); 3.82 (s, 2H, —S—CH₂—CO—N=); 5.05 (d, J=5, 1H, —H in the 6-position); 5.58 (dd, J=8 and 5, 1H, —H in the 7-position); 7.24 (s, 1H, —H of the thiazole); 7.35 (dd, J=8.5 and 2, 1H, aromatic —H in the 6-position); 7.55 (d, J=8.5, 1H, aromatic —H in the 5-position); 7.65 (d, J=2, 1H, aromatic —H in the 2-position); 9.07 (b, 1H, =N—H); 9.15 (d, J=8, 1H, —CONH—).

(250 MHz, d₆-DMSO+1γ of the CF₃COOD, δ in ppm, J in Hz): 2.87 (s, —6H, —N(CH₃)₂); 3.37 (t, J=6, 2H, =N—CH₂—); 3.74 (t, J=6, 2H, —NHCH₂—).

7-Amino-2-benzhydryloxycarbonyl-3-[2-(2-dimethylamino-ethylamino)-thiazol-5-yl]-8-oxo-5-thia-1-azabicyclo[4.2.0]oct-2-ene can be obtained in the following manner:

Methanesulphonic acid (0.3 cc) is added to a suspension of 2-benzhydryloxycarbonyl-7-t-butoxycarbonylamino-3-[2-(2-dimethylamino-ethylamino)-thiazol-5-yl]-8-oxo-5-thia-1-azabicyclo[4.2.0]oct-2-ene (0.3 g) in acetonitrile (3 cc). The yellow solution obtained is stirred at 23° C. for 5 minutes and is poured onto a mixture of a saturated sodium bicarbonate solution (50 cc) and ethyl acetate (50 cc). The organic phase is dried over anhydrous magnesium sulphate, filtered and concentrated under reduced pressure (20 mm Hg; 2.7 kPa). 7-Amino-2-benzhydryloxycarbonyl-3-[2-(2-dimethylamino-ethylamino)-thiazol-5-yl]-8-oxo-5-thia-1-azabicyclo[4.2.0]oct-2-ene (0.25 g) is thus obtained in the form of a yellow froth.

Infra-red spectrum (KBr): characteristic bands (cm⁻¹) at 3400, 1770, 1720, 1620, 1540, 1490, 1450, 1220, 760, 745 and 700.

Proton nuclear magnetic resonance spectrum (250 MHz, CDCl₃, δ in ppm, J in Hz): 2.26 (s, 6H, —N(CH₃)₂); 2.53 (t, J=6, 2H, >N—CH₂—); 3.17 (m, 2H, —NH—CH₂—); 3.50 and 3.66 (2d, J=18, 2H, —S—CH₂—); 4.77 (d broad, J=5, 1H, —H in the 7-position); 5.0 (d, J=5, 1H, —H in the 6-position); 6.0 (b, >NH); 6.90 (s, 1H, —H of the thiazole or —COOCH(C₆H₅)₂); 6.95 (s, 1H, —COOCH(C₆H₅)₂ or —H of the thiazole); 7.05 to 7.4 (m, aromatic protons, —NH₂).

2-Benzhydryloxycarbonyl-7-t-butoxycarbonylamino-3-[2-(2-dimethylamino-ethylamino)-thiazol-5-yl]-8-oxo-5-thia-1-azabicyclo[4.2.0]oct-2-ene can be obtained in the following manner:

A mixture of 1-(2-dimethylaminoethyl)-thiourea (22 g) in methylene chloride (200 cc) is added to a solution of 2-benzhydryloxycarbonyl-3-(1-bromo-2-oxoethyl)-7-t-butoxycarbonylamino-8-oxo-5-thia-1-azabicyclo[4.2.0]oct-2-ene (88 g) in anhydrous tetrahydrofuran (500 cc). After having been stirred for 24 hours at 25° C., the reaction mixture is poured onto a mixture of ethyl acetate (1.5 liters) and saturated sodium bicarbonate solution (1.5 liters). The organic phase is washed with saturated sodium bicarbonate solution (1 liter), distilled water (1 liter) and saturated sodium chloride solution (1 liter) and is then dried over anhydrous magnesium sulphate. After filtration, and concentration of the filtrate under reduced pressure (20 mm Hg; 2.7 kPa), the residue is purified by chromatography on silica gel (0.063–0.2 mm) [height of the silica layer: 38 cm, column diameter: 10 cm], elution being carried out with methylene chloride (5 liters) and then with a mixture (11 liters) of methylene chloride and methanol (90:10 by volume), and 1 liter fractions being collected. On concentrating fractions 14 to 16 to dryness, a yellow froth (15 g) is obtained, which is dissolved in hot acetonitrile (100 cc). On cooling, 2-benzhydryloxycarbonyl-7-t-butoxycarbonylamino-3-[2-(2-dimethylamino-ethylamino)-thiazol-5-yl ]-8-oxo-5-thia-1-azabicyclo[4.2.0]-oct-2-ene (3 g) is obtained in the form of white crystals (instantaneous melting point, by the Kofler method, 163° C.).

Infra-red spectrum (KBr): characteristic bands (cm⁻¹) at 3380, 3200, 1780, 1720, 1710, 1555, 1525, 1370, 1165, 755, 740 and 700.

Proton nuclear magnetic resonance spectrum (250 MHz, CDCl₃, δ ppm, J in Hz): 1.47 (s, 9H, —C(CH₃)₃); 2.27 (s, 6H, —N(CH₃)₂); 2.53 (t, J=6, 2H, >N—CH₂—); 3.18 (m, 2H, —NH—CH₂—); 3.52 and 3.66 (2d, J=18, 2H, —S—CH₂—); 5.04 (d, J=5, 1H in the 6-position); 5.40 (d, J=9, 1H, —CONH—); 5.64 (dd, J=9 and 5, 1H, —H in the 7-position); 5.93 (b, 1H, >NH); 6.96 (s, 1H, —H of the thiazole or —COO—CH(C$_6$H$_5$)$_2$); 6.97 (s, 1H, —COOCH(C$_6$H$_5$)$_2$ or —H of the thiazole); 7.15 to 7.40 (m, aromatic protons).

1-(2-Dimethylaminoethyl)-thiourea can be obtained in the following manner:

A solution of methyl N-[2-dimethylamino)-ethyl]-dithiocarbamate (139 g) in ethanol (600 cc) and 28% strength aqueous ammonia solution (275 cc) is heated under reflux for 36 hours. The mixture is concentrated under reduced pressure (20 mm Hg; 2.7 kPa) and the crystalline residue is washed with ethyl ether (200 cc). 1-(2-Dimethylaminoethyl)-thiourea (54 g) is obtained in the form of white crystals.

Infra-red spectrum (KBr): characteristic bands (cm$^{-1}$) at 3306, 2790, 1640, 1560 and 1350.

Methyl N-[2-(dimethylamino)-ethyl]-dithiocarbamate can be obtained in accordance with the method described in German patent application No. 2,738,711.

EXAMPLE 17

D-N-t-Butoxycarbonylphenylglycine (1.59 g) is added to a solution of crude 3-(2-acetamido-thiazol-5-yl)-7-amino-2-benzhydryloxycarbonyl-8-oxo-5-thia-1-azabicyclo[4.2.0]oct-2-ene (as obtained in Example 1) (3.2 g) in methylene chloride (50 cc). The solution is cooled to 4° C. and a solution of N,N'-dicyclohexylcarbodiimide (1.43 g) in methylene chloride (10 cc) is added in 10 minutes. After 50 minutes at about 4° C., the reaction mixture is filtered and then concentrated to dryness under reduced pressure (30 mm Hg; 4 kPa) at 30° C. The residue is taken up in ethyl acetate (150 cc) and the solution is washed successively with 0.1N hydrochloric acid (50 cc), a half-saturated sodium carbonate solution (50 cc), water (2×50 cc) and a saturated sodium chloride solution (50 cc), dried over magnesium sulphate, filtered and concentrated to dryness under reduced pressure (30 mm Hg; 4 kPa) at 40° C. The residue (the crude expected product) is purified by crystallisation from acetonitrile (90 cc). 3-(2-Acetylamino-thiazol-5-yl)-2-benzhydryloxycarbonyl-7-[(D)-α-2-t-butoxycarbonylamino-phenylacetamido]-8-oxo-5-thia-1-azabicyclo[4.2.0]oct-2-ene (2.38 g) is obtained in the form of a pale beige crystalline powder.

Infra-red spectrum (CHBr$_3$): characteristic bands (cm$^{-1}$) at 3400, 3260, 3160, 1780, 1715, 1690, 1560, 1500, 1490, 1450, 1390, 1370, 760 and 740.

Proton nuclear magnetic resonance spectrum (350 MHz, d$_6$-DMSO, δ in ppm, J in Hz): 1.4 (s, 9H, —C(CH$_3$)$_3$); 2.13 (s, 3H, —CO—CH$_3$); 3.67 and 3.81 (2d, J=18, 2H, —S—CH$_2$—); 5.12 (d, J=5, 1H, —H in the 6-position);

5.35 (d, J = 8, 1H, \N—CH—CO—N/ );

5.54 (d, J = 8, 0.5H, —NH—C(=O)O— partly exchanged); 5.83 (dd, J=5 and 9, 1H, —H in the 7-position); 6.82 (s, 1H, —COO—CH(C$_6$H$_5$)$_2$); 7 to 7.5 (m, 16H, aromatic protons and —H of the thiazole); 9.26 (d, J=9, 1H, —CO—NH—); 12.04 (s, 1H, —NH—CO—CH$_3$).

3-(2-Acetylamino-thiazol-5-yl)-2-benzhydryloxycarbonyl-7-[(D)-α-t-butoxycarbonylamino-phenylacetamido]-8-oxo-5-thia-1-azabicyclo[4.2.0]oct-2-ene (2.25 g) is dissolved in trifluoroacetic acid (20 cc). The solution is stirred at 25° C. for 20 minutes and then concentrated to dryness under reduced pressure (5 mm Hg; 0.7 kPa) at 40° C. The residue is taken up in isopropyl ether (30 cc). The mixture is again evaporated to dryness under reduced pressure (30 mm Hg; 4 kPa) at 40° C. This operation is repeated 4 times and the residue is then triturated with ethyl ether (100 cc), filtered off, washed with ethyl ether (3×30 cc) and dried. 3-(2-Acetylamino-thiazol-5-yl)-7-[(D)-α-amino-phenylacetamido]-2-carboxy-8-oxo-5-thia-1-azabicyclo[4.2.0]-oct-2-ene trifluoroacetate (1.45 g) is obtained in the form of a beige powder.

Infra-red spectrum (KBr): characteristic bands (cm$^{-1}$) at 3180, 3100, 2150, 1775, 1680, 1455, 1200, 800, 720 and 700.

Proton nuclear magnetic resonance spectrum (350 MHz, d$_6$-DMSO, δ in ppm, J in Hz): 2.13 (s, 3H, —CO—CH$_3$); 3.66 and 3.78 (2d, J=18, 2H, —S—CH$_2$—);

5.01 (s, 1H, \N—CH—CO—N/ );

5.11 (d, J=4.5, 1H, —H in the 6-position); 5.81 (b, 1H, —H in the 7-position); 7.35 to 7.65 (m, 6H, aromatic protons and —H of the thiazole); 8 to 10 (b smudged, 1H, —COOH); 9.58 (d, J=8, 1H, —CO—NH—); 12.14 (b, 1H, —NH—CO—CH$_3$).

This trifluoroacetate (1.2 g) is redissolved in water (100 cc) and the solution is washed with ethyl acetate (3×20 cc), then decanted, treated with decolorising charcoal (0.5 g), filtered and stirred with Amberlite IR 45 resin (OH$^-$) (20 cc) (washed beforehand with water until neutral), until the pH of the aqueous solution reaches 5.5. After removing the resin by filtration, the aqueous solution is lyophilized. 3-(2-Acetylamino-thiazol-5-yl)-7-[(D)-α-aminophenylacetamido]-2-carboxy-8-oxo-5-thia-1-azabicyclo[4.2.0]oct-2-ene (0.58 g) is obtained in the form of a white lyophilizate.

Infra-red spectrum (KBr): characteristic bands (cm$^{-1}$) at 3240, 3100–2300, 1765, 1685, 1600, 1545, 1510, 1455, 1370, 720 and 700.

The nuclear magnetic resonance spectrum (CF$_3$CO$_2$H) agrees with that of the trifluoroacetate.

EXAMPLE 18

Following the working method described in Example 17, 7-amino-2-benzhydryloxycarbonyl-8-oxo-3-(thiazol-5-yl)-5-thia-1-azabicyclo[4.2.0]oct-2-ene (4.9 g) is acylated with (D)-N-t-butoxycarbonylphenylglycine (2.74 g) in the presence of N,N'-dicyclohexylcarbodiimide (2.5 g), in methylene chloride (40 cc). After chromatography on a column (height: 30 cm, diameter: 4 cm) of silica gel (0.04–0.06 mm), elution being carried out under a pressure of 1 bar (100 kPa) with a mixture of cyclohexane and ethyl acetate (60:40 by volume) and 100 cc fractions being collected, fractions 15 to 24, containing the pure product, are combined and concentrated to dryness under reduced pressure (30 mm Hg; 4 kPa) at 30° C. 2-Benzhydryloxycarbonyl-8-oxo-7-[(D)-α-t-butoxycarbonylaminophenylacetamido]-3-(thiazol-5-yl)-5-thia-1-azabicyclo[4.2.0]oct-2-ene (2.4 g) is obtained in the form of a cream-coloured solid.

Infra-red spectrum (CHBr$_3$): characteristic bands (cm$^{-1}$) at 3400, 1788, 1715, 1690, 1490, 1450, 1390, 1365, 755 and 740.

Proton nuclear magnetic resonance spectrum (350 MHz, CDCl$_3$, δ in ppm, J in Hz): 1.43 (s, J=9, —C(CH$_3$)$_3$); 3.42 and 3.63 (2d, J=18, 2H, —S—CH$_2$—); 5.02 (d, J=5, 1H, —H in the 6-position);

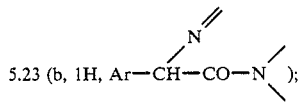

5.23 (b, 1H, Ar—CH—CO—N );

5.65 (d, J=6, 1H, —NH—COO—); 5.89 (dd, J=5 and 9, 1H, —H in the 7-position); 6.65 (b, 1H, —CO—NH—); 6.89 (s, 1H, —COO—CH(C$_6$H$_5$)$_2$); 7 to 7.45 (m, aromatic protons); 7.53 (s, 1H, =CH—N= of the thiazole); 8.56 (s, 1H, —N=CH—S— of the thiazole).

Following the working method of Example 17, 2-benzhydryloxycarbonyl-7-[(D)-α-t-butoxycarbonylaminophenylacetamido]-8-oxo-3-(thiazol-5-yl)-5-thia-1-azabicyclo[4.2.0]oct-2-ene (2.4 g) is treated with trifluoroacetic acid (24 cc). 7-[(D)-α-Aminophenylacetamido]-2-carboxy-8-oxo-3-(thiazol-5-yl)-5-thia-1-azabicyclo[4.2.0]oct-2-ene trifluoroacetate (1.25 g) is obtained in the form of a cream-coloured solid.

Infra-red spectrum (KBr): characteristic bands (cm$^{-1}$) at 3200, 3150–2200, 1770, 1680, 1620, 1550, 1205, 1140, 800 and 725.

Proton nuclear magnetic resonance spectrum (350 MHz, CF$_3$COOD, δ in ppm, J in Hz): 3.60 and 4.01 (2d, J=19, 2H, —CH$_2$—S—); 5.38 (d, J=5, 1H, —H in the 6-position);

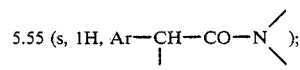

5.55 (s, 1H, Ar—CH—CO—N );

5.98 (d, J=5, 1H, —H in the 7-position); 7 to 7.5 (m, 5H, aromatic protons); 8.32 (s, 1H, H in the 4-position of the thiazole); 9.97 (s, 1H, H in the 2-position of the thiazole).

7-Amino-2-benzhydryloxycarbonyl-8-oxo-3-(thiazol-5-yl)-5-thia-1-azabicyclo[4.2.0]oct-2-ene can be obtained in the following manner:

Following the working method described in Example 15, 2-benzhydryloxycarbonyl-7-t-butoxycarbonylamino-8-oxo-3-(thiazol-5-yl)-5-thia-1-azabicyclo[4.2.0]oct-2-ene (10 g) is treated with methanesulphonic acid (10 cc) in acetonitrile (100 cc). 7-Amino-2-benzhydryloxycarbonyl-8-oxo-3-(thiazol-5-yl)-5-thia-1-azabicyclo[4.2.0]oct-2-ene (8.2 g) is obtained in the form of a yellow solid.

Infra-red spectrum (CHBr$_3$): characteristic bands (cm$^{-1}$) at 3400, 3300, 1780, 1725, 1620, 1495, 1450, 1220, 755 and 740.

Proton nuclear magnetic resonance spectrum (350 MHz, CDCl$_3$, δ in ppm, J in Hz): 3.55 and 3.74 (2d, J=18, 2H, —SCH$_2$—); 4.85 (d, J=5, 1H, H in the 7-position); 5.05 (d, J=5, 1H, H in the 6-position); 6.92 (s, 1H, CH(C$_6$H$_5$)$_2$); 7 to 7.45 (m, 10 aromatic —H); 7.55 (s, 1H, H in the 4-position of the thiazole); 8.55 (s, 1H, H in the 2-position of the thiazole).

EXAMPLE 19

Following the working method described in Example 15, 2-benzhydryloxycarbonyl-7-t-butoxycarbonylamino-8-oxo-3-(2-phenyl-thiazol-5-yl)-5-thia-1-azabicyclo[4.2.0]oct-2-ene (4.9 g) is treated with methanesulphonic acid (4.9 cc) in acetonitrile (49 cc). Crude 7-amino-2-benzhydryloxycarbonyl-8-oxo-3-(2-phenyl-thiazol-5-yl)-5-thia-1-azabicyclo[4.2.0]oct-2-ene (4.1 g) is obtained, and is then acylated in accordance with the working method described in Example 17, using (D)-N-t-butoxycarbonylphenylglycine (1.96 g) in the presence of N,N'-dicyclohexylcarbodiimide (1.78 g) in dry methylene chloride (40 cc). The crude product obtained is purified by chromatography on a column (height: 30 cm, diameter: 4 cm) of silica gel (0.04–0.06 mm), elution being carried out under a pressure of 0.5 bar (50 kPa) with a mixture of cyclohexane and ethyl acetate (60:40 by volume), and 50 cc fractions being collected. Fractions 9 to 33, containing the pure product, are combined and concentrated to dryness under reduced pressure (30 mm Hg; 4 kPa) at 30° C. 2-Benzhydryloxycarbonyl-7-[(D)-α-t-butoxycarbonylaminophenylacetamido]-8-oxo-3-(2-phenyl-thiazol-5-yl)-5-thia-1-azabicyclo[4.2.0]-oct-2-ene (2.8 g) is obtained in the form of a cream-coloured solid.

Infra-red spectrum (CHBr$_3$): characteristic bands (cm$^{-1}$) at 3410, 1785, 1720, 1695, 1495, 1370, 1225 and 760.

Proton nuclear magnetic resonance spectrum (350 MHz, CDCl$_3$, δ in ppm, J in Hz): 1.43 (s, 9H, —C(CH$_3$)$_3$); 3.49 and 3.66 (2d, J=18, 2H, —S—CH$_2$—); 5.04 (d, J=4.5, 1H, —H in the 6-position);

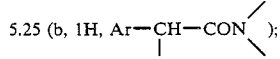

5.25 (b, 1H, Ar—CH—CON );

5.67 (d, J=6, 1H, —NH—COO—); 5.91 (dd, J=4.5 and 9, 1H, —H in the 7-position); 6.63 (b, 1H, —CO—NH— in the 7-position); 6.94 (s, 1H, —COO—CH(C$_6$H$_5$)$_2$); 7 to 7.5 (m, aromatic protons); 7.48 (s, 1H, H of the thiazole); 7.73 (dd, J=7 and 1.5, 2H, aromatic —H in the ortho-positions to the thiazole).

2-Benzhydryloxycarbonyl-7-[(D)-α-t-butoxycarbonylaminophenylacetamido]-8-oxo-3-(2-phenyl-thiazol-5-yl)-5-thia-1-azabicyclo[4.2.0]oct-2-ene (2.8 g) is treated with trifluoroacetic acid (28 cc) in the presence of anisole (2 cc) for 1 hour at between 0° and 5° C., and the mixture is then concentrated to dryness under reduced pressure (2 mm Hg; 0.27 kPa) at 35° C. The residue is triturated with isopropyl ether (35 cc), which is evaporated under reduced pressure (30 mm Hg; 4 kPa) at 30° C. This operation is repeated twice more, and the residue is then taken up in isopropyl ether (50 cc). The insoluble matter is filtered off, washed with isopropyl ether (30 cc) and ethyl ether (2×30 cc), and dried. 7-[(D)-α-Aminophenylacetamido]-2-carboxy-8-oxo-3-(2-phenyl-thiazol-5-yl)-5-thia-1-azabicyclo[4.2.0]oct-2-ene trifluoroacetate (2 g) is obtained in the form of a pale yellow solid.

Infra-red spectrum (KBr): characteristic bands (cm$^{-1}$) at 3220, 3120-2200, 1770, 1700-1680, 1615, 1520, 1450, 1205, 1140, 800 and 720.

Proton nuclear magnetic resonance spectrum (350 MHz, d$_6$ DMSO, δ in ppm, J in Hz): 3.71 and 3.80 (2d, J=18, 2H, —S—CH$_2$—);

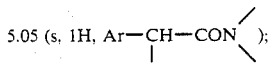
5.05 (s, 1H, Ar—CH—CON );

5.12 (d, J=5, 1H, —H in the 6-position); 5.8 (b, 1H, —H in the 7-position); 7.4 to 7.6 (m, 8H, aromatic protons); 7.88 (d, 2H, aromatic —H in the ortho-positions to the thiazole); 7.90 (s, 1H, —H or the thiazole); 8 to 10 (b smudged, —NH$_2$, —COOH); 9.64 (d, J=9, 1H, —CONH— in the 7-position).

EXAMPLE 20

Isobutyl chloroformate (1.3 cc) is added to a suspension, cooled to −10° C., of (D)-N-t-butoxycarbonyl-(4-hydroxyphenyl)-glycine (2.53 g) and triethylamine (1.33 cc) in tetrahydrofuran (40 cc) and the reaction mixture is then stirred at a temperature of between −10° and −15° C. for 1 hour, after which a solution of 7-amino-2-carboxy-8-oxo-3-(thiazol-5-yl)-5-thia-1-azabicyclo[4.2.0]oct-2-ene trifluoroacetate (3.8 g) and triethylamine (4 cc) in a mixture of tetrahydrofuran (20 cc) and distilled water (20 cc) is added in 10 minutes. The reaction mixture is stirred for 1 hour at a temperature of between 0° and 5° C. and then for 2 hours at 20° C. After evaporation of the tetrahydrofuran under reduced pressure (30 mm Hg; 4 kPa) at 30° C., a saturated sodium bicarbonate solution (50 cc) is added and the aqueous phase is washed with ethyl acetate (100 cc); it is then acidified to pH 2 with 4N hydrochloric acid and extracted with ethyl acetate (2×100 cc). The organic phase is washed with distilled water (100 cc) and a saturated sodium chloride solution (100 cc), then dried, and concentrated to dryness under reduced pressure (30 mm Hg; 4 kPa) at 30° C. Crude 7-[(D)-α-t-butoxycarbonylamino-(4-hydroxyphenyl)-acetamido]-2-carboxy-8-oxo-3-(thiazol-5-yl)-5-thia-1-azabicyclo[4.2.0]oct-2-ene (1.2 g) is obtained in the form of a yellow froth [Rf=0.35; silica gel chromatographic plate, eluant: a mixture of ethyl acetate, acetone, water and formic acid (50:10:5:5 by volume)], which is purified by conversion to its benzhydryl ester, in the following manner:

The crude product is redissolved in acetonitrile (25 cc) and is then esterified with diphenyldiazomethane (0.4 g) for 1 hour at 20° C.; after having been concentrated to 10 cc under reduced pressure (30 mm Hg; 4 kPa) at 30° C., the mixture is taken up in ethyl acetate (100 cc) and the solution is washed with 4N hydrochloric acid (50 cc), a saturated sodium bicarbonate solution (50 cc) and a saturated sodium chloride solution (2×50 cc). After having been dried over magnesium sulphate, the mixture is concentrated to dryness under reduced pressure (30 mm Hg; 4 kPa) at 30° C. and the residue is then chromatographed on a column (height: 20 cm, diameter: 2 cm) of silica gel (0.04–0.06 mm), elution being carried out under a pressure of 0.4 bar (40 kPa) with a mixture of cyclohexane and ethyl acetate (50:50 by volume) and 50 cc fractions being collected. Fractions 11 to 24, containing the pure product, are combined and concentrated to dryness under reduced pressure (30 mm Hg; 4 kPa) at 30° C. 2-Benzhydryloxycarbonyl-7-[(D)-α-t-butoxycarbonylamino-(4-hydroxyphenyl)-acetamido]-8-oxo-3-(thiazol-5-yl)-5-thia-1-azabicyclo[4.2.0]oct-2-ene (0.16 g) is obtained in the form of an amorphous yellow solid.

Infra-red spectrum (CHBr$_3$): characteristic bands (cm$^{-1}$) at 3560, 3400, 3330, 1785, 1720, 1690, 1610, 1595, 1490, 1450, 1390, 1365, 1220 and 755.

Proton nuclear magnetic resonance spectrum (350 MHz, CDCl$_3$, δ in ppm, J in Hz): 1.45 (s, 9H, —C(CH$_3$)$_3$); 3.43 and 3.63 (2d, J=18, 2H, —S—CH—); 5.03 (d, J=5, 1H, —H in the 6-position);

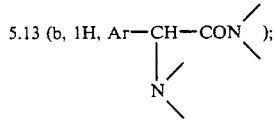
5.13 (b, 1H, Ar—CH—CON );

5.60 (b, 1H, —NH—COO—); 5.87 (dd, J=5 and 9 and b, 2H, —H in the 7-position and —OH); 6.62 (d, J=9, 1H, —CO—NH—); 6.77 (d, J=8, 2H, aromatic —H in the ortho-positions to the —OH); 6.90 (s, 1H, —COO—CH(C$_6$H$_5$)$_2$); 7 to 7.4 (m, aromatic protons); 7.52 (s, 1H, =CH—N= of the thiazole); 8.56 (s, 1H, —N=CH—S— of the thiazole).

Following the working method of Example 17, 2-benzhydryloxycarbonyl-7-[(D)-α-t-butoxycarbonylamino-(4-hydroxyphenyl)-acetamido]-8-oxo-3-(thiazol-5-yl)-5-thia-1-azabicyclo[4.2.0]oct-2-ene (0.16 g) is treated with trifluoroacetic acid (5 cc); 7-[(D)-α-amino-(4-hydroxyphenyl)-acetamido]-2-carboxy-8-oxo-3-(thiazol-5-yl)-5-thia-1-azabicyclo[4.2.0]oct-2-ene trifluoroacetate (0.082 g) is obtained in the form of a cream-coloured solid.

Infra-red spectrum (KBr): characteristic bands (cm$^{-1}$) at 3300-2200, 1775, 1675, 1610, 1515, 1200, 1135, 840, 800 and 720.

Proton nuclear magnetic resonance spectrum (350 MHz, d$_6$ DMSO, in ppm, J in Hz): 3.73 and 3.82 (2d, J=18, 2H, —CH$_2$—S—);

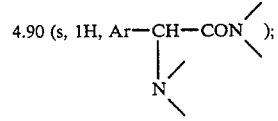
4.90 (s, 1H, Ar—CH—CON );

5.15 (s, J=5, 1H, —H in the 6-position); 5.84 (dd, J=5 and 9, 1H, —H in the 7-position); 6.80 (s, J=8, 2H, aromatic —H in the ortho-positions to the —OH); 7.30 (d, J=8, 2H, aromatic —H in the meta-positions to the —OH); 7.88 (s, 1H, =CH—N= of the thiazole); 8.60 (b, 3H, —NH$_3^\oplus$); 9.06 (s, 1H, —N=CH—S—); 9.53 (d, J=9, 1H, —CO—NH—); 9.80 (b, 1H, —OH); 13.25 (b very smudged, —COOH).

Following the working method of Example 17, starting from 7-[(D)-α-amino-(4-hydroxyphenyl)-acetamido]-2-carboxy-8-oxo-3-(thiazol-5-yl)-5-thia-1-azabicyclo[4.2.0]oct-2-ene trifluoroacetate (3.9 g) and carrying out a treatment with Amberlite IR 45 resin (in the OH$^-$ form) (25 cc) in distilled water (100 cc), followed by filtration and lyophilization, 7-[(D)-α-amino-(4-hydroxyphenyl)-acetamido]-2-carboxy-8-oxo-3-(thiazol-5-yl)-5-thia-1-azabicyclo[4.2.0]oct-2-ene (inner salt) (1.6 g) is obtained in the form of a white lyophilizate.

Infra-red spectrum (KBr): characteristic bands (cm$^{-1}$) at 3300–2200, 1765, 1690, 1610, 1520, 1390, 1250 and 840.

The proton nuclear magnetic resonance spectrum (CF$_3$CO$_2$D) is identical to that of the trifluoroacetate, recorded under the same conditions.

7-Amino-2-carboxy-8-oxo-3-(thiazol-5-yl)-5-thia-1-azabicyclo[4.2.0]oct-2-ene can be prepared in the following manner:

Following the working method described in Example 6, 2-benzhydryloxycarbonyl-7-t-butoxycarbonylamino-8-oxo-3-(thiazol-5-yl)-5-thia-1-azabicyclo[4.2.0]oct-2-ene (5.2 g) is treated with trifluoroacetic acid (80 cc). 7-Amino-2-carboxy-8-oxo-3-(thiazol-5-yl)-5-thia-1-azabicyclo[4.2.0]-oct-2-ene trifluoroacetate (4 g) is obtained in the form of a cream-coloured solid.

Infra-red spectrum (KBr): characteristic bands (cm$^{-1}$) at 3300–2200, 1785, 1680, 1620, 1205, 1180, 1140, 800 and 725.

EXAMPLE 21

A solution of 3-(2-acetylamino-thiazol-5-yl)-2-benzhydryloxycarbonyl-8-oxo-7-tritylamino-5-oxa-1-azabicyclo[4.2.0]oct-2-ene (0.54 g) and of para-toluenesulphonic acid monohydrate (0.14 g) in acetone (5 cc) is heated under reflux for 3 hours. The reaction mixture is diluted with ethyl acetate (10 cc). The organic solution is washed with a half-saturated sodium bicarbonate solution (10 cc) and with a saturated sodium chloride solution (10 cc) and is then dried over anhydrous sodium sulphate. It is filtered, the insoluble matter is washed with ethyl acetate (2×5 cc) and the organic solution is concentrated to dryness under reduced pressure (3 mm Hg; 0.4 kPa) at 40° C. The residue (0.58 g) is a chestnut-coloured froth which principally contains 7-amino-3-(2-acetylamino-thiazol-5-yl)-2-benzhydryloxycarbonyl-8-oxo-5-oxa-1-azabicyclo[4.2.0]oct-2-ene [Rf=0.11 (silica gel chromatographic plate; eluant: a 20:80 mixture of cyclohexane and ethyl acetate)]. To a solution, cooled to 0° C., of 0.58 g of the preceding product, dissolved in dry tetrahydrofuran (5 cc), is added dropwise, in the course of 2 minutes, thien-2-yl-acetyl chloride (0.117 g) dissolved in tetrahydrofuran (1 cc). The chestnut-coloured solution obtained is stirred for 5 minutes at 0° C. and triethylamine (0.073 g) dissolved in dry tetrahydrofuran (1 cc) is then added dropwise. Stirring is continued for 1 hour 15 minutes at 0° C. The mixture is then filtered and the filtrate is washed with a half-saturated sodium bicarbonate solution (25 cc), distilled water (25 cc) and a saturated sodium chloride solution (25 cc). The organic phase is dried over anhydrous sodium sulphate and filtered, and the insoluble matter is then washed with ethyl acetate (2×5 cc). The organic solution is concentrated to dryness under reduced pressure (30 mm Hg; 4 kPa) at 40° C., and the residue is chromatographed on silica gel (0.2–0.06 mm) (column diameter: 1.4 cm; height of the silica layer: 15 cm), elution being carried out with mixtures of cyclohexane and ethyl acetate in the ratios of 50:50 (500 cc), 40:60 (200 cc) and 30:70 (200 cc), and 15 cc fractions being collected. Fractions 40 to 49 are combined and the solvent is evaporated under reduced pressure. 3-(2-Acetylamino-thiazol-5-yl)-2-benzhydryloxycarbonyl-8-oxo-7-(thien-2-yl)-acetamido-5-oxa-1-azabicyclo[4.2.0]oct-2-ene (0.1 g) is obtained in the form of a chestnut-coloured powder.

Proton nuclear magnetic resonance spectrum (350 MHz, CDCl$_3$, δ in ppm, J in Hz): 2.10 (s, 3H, >N—CO—CH$_3$); 3.90 (limiting AB system, —CH$_2$—CO—N<); 3.80 and 4.20 (m, —CH$_2$—O—); 5.04 (d, J=3.5, 1H, —H in the 6-position); 5.94 (dd, J=3.5 and 10); 6.73 (s, 1H, —COO—CH(C$_6$H$_5$)$_2$); 6.8 to 6.95 (m, =CH—CH= of the thiophene); 6.9 to 7.6 (m, aromatic protons, —H of the thiazole and —S—CH= of the thiophene); 7.77 (b, 1H, —CO—NH—); 13.15 (b, 1H, —NH—CO—CH$_3$).

A solution of 3-(2-acetylamino-thiazol-5-yl)-2-benzhydryloxycarbonyl-8-oxo-7-(thien-2-yl)-acetamido-5-oxa-1-azabicyclo[4.2.0]oct-2-ene (0.1 g) in formic acid (5 cc) is heated at 50° C. for 30 minutes, with stirring. The mixture is concentrated to dryness under reduced pressure (30 mm Hg; 4 kPa) at 50° C., and the residue is dissolved in ethanol (5 cc). The suspension obtained is stirred at 50° C. for 5 minutes and the solvent is evaporated under reduced pressure (30 mm Hg; 4 kPa) at 50° C.; this operation is repeated once, and the residue thus obtained is taken up in ethanol (2 cc). The solid in suspension yields, on filtration, 3-(2-acetylamino-thiazol-5-yl)-2-carboxy-8-oxo-7-(thien-2-yl)-acetamido-5-oxa-1-azabicyclo[4.2.0]oct-2-ene (12 mg) in the form of a beige powder.

Infra-red spectrum (KBr): characteristic bands (cm$^{-1}$) at 3280, 3100, 2220, 1790, 1690, 1655, 1540, 1515 and 700.

Proton nuclear magnetic resonance spectrum (350 MHz, d$_6$-DMSO, δ in ppm, J in Hz): 2.14 (s, 3H, >N—CO—CH$_3$); 3.76 (s, 2H, —CH$_2$—CO—N<); 4.53 and 4.93 (2d, J=18, 2H, —CH$_2$—O—); 5.23 (d, J=3.5, 1H, —H in the 6-position); 5.58 (dd, J=3.5 and 9.5, 1H, —H in the 7-position); 6.85 to 7 (m, 2H, =CH—CH= of the thiophene); 7.35 (dd, =CH—S— of the thiophene); 7.61 (s, 1H, —H, of the thiazole); 8.97 (d, J=9.5, 1H, —CO—NH—).

A solution of acetyl chloride (0.11g) in dry tetrahydrofuran (2 cc) is added, in 3 minutes, to a solution, cooled to 0° C., of 3-(2-amino-thiazol-5-yl)-2-benzhydryloxycarbonyl-8-oxo-7-tritylamino-5-oxa-1-azabicyclo[4.2.0]oct-2-ene (0.80 g) in dry tetrahydrofuran (10 cc), and a solution of triethylamine (0.18 cc) in dry tetrahydrofuran (2 cc) is then added. The mixture is stirred for 30 minutes at 0° C. and is then filtered over a diatomaceous earth powder. The filtrate is diluted with ethyl acetate (50 cc) and washed with distilled water (50 cc), a half-saturated sodium bicarbonate solution (50 cc) and a saturated sodium chloride solution (50 cc). The organic phase is dried over anhydrous sodium sulphate; it is filtered, the insoluble matter is washed with ethyl acetate (10 cc) and the organic solution is concentrated under reduced pressure (30 mm Hg; 4 kPa) at 40° C. The residue (0.89 g) is chromatographed on a column (height: 24 cm; diameter: 2.2 cm) of silica (0.04–0.06 mm), elution being carried out with a 40:60 (by volume) mixture of cyclohexane and ethyl acetate under 0.4 kPa, and 60 cc fractions being collected. Fractions 5 to 11 are combined and the solvent is evaporated under reduced pressure (30 mm Hg; 4 kPa) at 40° C. 3-(2-Acetylamino-thiazol-5-yl)-2-benzhydryloxycarbonyl-8-oxo-7-tritylamino-5-oxa-1-azabicyclo[4.2.0]oct-2-ene (0.55 g) is obtained in the form of a pale chestnut-coloured froth.

Infra-red spectrum (KBr): characteristic bands (cm$^{-1}$) at 3340, 1790, 1725, 1700, 1540 and 1210.

Proton nuclear magnetic resonance spectrum (350 MHz, CDCl$_3$, δ in ppm, J in Jz): 2.16 (s, 3H, >N—

CO—CH₃); 3.14 (d, J=10, 1H, —NH—C(C₆H₅)₃); 3.89 (d, J=3.5, 1H, —H in the 6-position); 4.05 and 4.48 (d, J=18, 2H, —CH₂—O—); 4.43 (dd, J=10 and 3.5, 1H, —H in the 7-position); 6.86 (s, 1H, —COOCH(C₆H₅)₂); 7.10 (s, 1H, —H of the thiazole); 7.10 to 7.65 (m, aromatic protons); 10.93 (b, 1H, —NH—CO—CH₃).

Bromine (1.72 g) dissolved in dry methylene chloride (7 cc) is added, in 10 minutes, to a solution, cooled to −78° C., of 2-benzhydryloxycarbonyl-3-(2-dimethylamino-vinyl)-8-oxo-7-tritylamino-5-oxa-1-azabicyclo[4.2.0]-oct-2-ene, E-isomer (7.14 g), in dry tetrahydrofuran (50 cc); the mixture is stirred for 10 minutes at −78° C., the temperature is then allowed to rise to −40° C., and distilled water (0.39 cc) is added. After 10 minutes, an aliquot portion (5 cc) of the reaction mixture is taken and diluted with ethyl acetate (10 cc). This organic phase is washed with distilled water (5 cc) and then with a half-saturated sodium chloride solution (5 cc). It is then dried over anhydrous sodium sulphate and concentrated to dryness under reduced pressure (30 mm Hg; 4 kPa) at 20° C. The residue (0.61 g) is chromatographed on a column (height: 21 cm; diameter: 1.8 cm) of silica gel (0.04–0.06 mm), elution being carried out under 40 kPa with a 75:25 (by volume) mixture of cyclohexane and ethyl acetate, and 25 cc fractions being collected. Fractions 3 and 4, containing the mixture of epimers of 2-benzhydryloxycarbon-yl-3-(1-bromo-2-oxoethyl)-8-oxo-7-tritylamino-5-oxa-1-azabicyclo[4.2.0]oct-2-ene are combined and concentrated to dryness under reduced pressure (30 mm Hg; 4 kPa) at 20° C. A mixture (0.03 g) of the two bromoaldehydes is obtained in the form of a chestnut-coloured froth.

Position of the characteristic peaks of the proton nuclear magnetic resonance spectrum (350 MHz, CDCl₃, δ in ppm, J in Hz): 6.22 and 6.41 (s, 2H, >CHBr); 9.27 (s, 2H, —CHO).

A solution of thiourea (1.23 g) in a mixture of tetrahydrofuran (8 cc) and water (1.6 cc) is added, in 10 minutes, to the initial reaction mixture, kept at −20° C., and the temperature is then allowed to rise to 20° C., with stirring, in the course of 30 minutes. The mixture is then transferred into a separating funnel containing ethyl acetate (300 cc) and is washed with a half-saturated sodium bicarbonate solution (250 cc), with water (250 cc) and with a saturated sodium chloride solution (250 cc). The organic phase is then dried over anhydrous sodium sulphate; it is filtered and the filtrate is concentrated to dryness under reduced pressure (30 mm Hg; 4 kPa) at 40° C. The residue (6.48 g) is chromatographed on silica gel (0.04–0.06 mm), elution being carried out under 40 kPa with a 30:70 (by volume) mixture of cyclohexane and ethyl acetate, and 60 cc fractions being collected. Fractions 12 to 21, containing the product, are combined and the eluant is evaporated under reduced pressure (30 mm Hg; 4 kPa) at 40° C. 3-(2-Amino-thiazol-5-yl)-2-benzhydryloxycarbonyl-8-oxo-7-tritylamino-5-oxa-1-azabicyclo[4.2.0.]oct-2-ene (0.65 g) is obtained in the form of a light chestnut-coloured froth.

Infra-red spectrum (KBr): characteristic bands (cm⁻¹) at 1790, 1725, 1490, 1220, 745 and 700.

Proton nuclear magnetic resonance spectrum (350 MHz, CDCl₃, δ in ppm, J in Hz): 3.12 (d, J=10, 1H, —NH—C(C₆H₅)₃); 3.85 (d, J=3.5, 1H, —H in the 6-position); 4.05 and 4.50 (2d, J=18, 2H, —CH₂—O—); 4.39 (dd, J=3.5 and 10, 1H, —H in the 7-position); 4.88 (b, 2H, —NH₂); 6.91 (s, —COOCH(C₆H₅)₂, —H of the thiazole); 7.10 to 7.65 (m, aromatic protons).

2-Benzhydryloxycarbonyl-3-(2-dimethylamino-vinyl)-8-oxo-7-tritylamino-5-oxa-1-azabicyclo[4.2.0]oct-2-ene, E-form, can be obtained in the following manner:

A solution of 2-benzhydryloxycarbonyl-3-methyl-8-oxo-7-tritylamino-5-oxa-1-azabicyclo[4.2.0]oct-2-ene (4.25 g) in dimethylformamide (20 cc) is heated at 80° C., under nitrogen. Whilst the solution is kept stirred at 80° C., t-butoxy-bis-dimethylaminomethane (1.55 cc) is added dropwise in the course of 7 minutes. When all has been added, the mixture is stirred for a further 17 minutes at 80° C. The solution is diluted with ethyl acetate (150 cc) and the organic phase is washed with distilled water (3×60 cc) and a half-saturated sodium chloride solution (60 cc), dried over sodium sulphate, filtered and concentrated to dryness at 30° C. under reduced pressure (20 mm Hg; 2.7 kPa). The residue is triturated in ethyl ether (150 cc), the suspension obtained is filtered and the filtrate is concentrated to dryness at 30° under reduced pressure (20 mm Hg; 2.7 kPa). A crude product (3.14 g) consisting principally of 2-benzhydryloxycarbonyl-3-(2-dimethylamino-vinyl)-8-oxo-7-tritylamino-5-oxa-1-azabicyclo[4.2.0]oct-2-ene, E-form, is obtained and can be used without additional purification.

Infra-red spectrum (KBr): characteristic bands (cm⁻¹) at 1780, 1660, 1615, 1490, 1450, 745 and 700.

Proton nuclear magnetic resonance spectrum (350 MHz, CDCl₃, δ in ppm, J in Hz): 2.77 (s, 6H, —N(CH₃)₂); 3.71 (d, J=3.5, 1H, H in the 6-position); 4.12 and 4.53 (2d, J=17, 2H, —CH₂—O—); 4.26 (b, 1H, H in the 7-position); 6.24 and 6.40 (2d, J=13, 2H, —CH=CH—); 6.81; (s, 1H, —COO—CH(C₆H₅)₂).

2-Benzhydryloxycarbonyl-3-methyl-8-oxo-7-tritylamino-5-oxa-1-azabicyclo[4.2.0]oct-2-ene (7.74 g) is prepared according to a synthesis scheme described in U.S. Pat. No. 4,108,992, in which the t-butyl glyoxylate is replaced by benzhydryl glyoxylate prepared according to French Pat. No. 1,495,047.

The expected oxacephalosporin is obtained in the form of a white solid from 3-tritylamino-4-(prop-2-ynyloxy)-2-oxo-azetidine (13.2 g).

Infra-red spectrum (KBr): characteristic bands (cm⁻¹) at 3340, 1780, 1715, 1620, 1595, 1585, 1490, 1450, 1220, 745 and 700.

Proton nuclear magnetic resonance spectrum (350 MHz, CDCl₃, δ in ppm, J in Hz): 1.90 (s, 3H, —CH₃); 3.75 (d, J=3.5, 1H, H in the 6-position); 3.87 and 4.08 (2d, J=18, 2H, —CH₂—O—); 4.30 (d, J=3.5, 1H, H in the 7-position); 6.85 (s, 1H, —COO—CH(C₆H₅)₂); 7.15 to 7.4 (m, 26H, aromatic protons and —H-N—C(C₆H₅)₃).

EXAMPLE 22

A solution of acetyl chloride (1.22 cc) in dry tetrahydrofuran (10 cc) is added, in 5 minutes, to a solution, cooled to 4° C., of 3-(2-amino-thiazol-5-yl)-2-benzhydryloxycarbonyl-7-[(D)-α-t-butoxycarbonylamino-phenylacetamido]-8-oxo-5-thia-1-azabicyclo[4.2.0]oct-2-ene (10 g) in dry tetrahydrofuran (140 cc); 5 minutes thereafter, a solution of triethylamine (2.15 cc) in tetrahydrofuran (5 cc) is added. The reaction mixture is stirred for 4 hours at about 5° C. and is then filtered, partially concentrated and poured into a mixture of ethyl acetate (200 cc) and a half-saturated sodium bicarbonate solution (200 cc); the organic phase is washed with water (2×100 cc) and saturated sodium chloride solution (100 cc) and is then dried over magnesium sulphate. After evaporation of the solvent under reduced pressure (30 mm Hg; 4 kPa) at 40° C., the residue is crystallised from acetonitrile (80 cc). 3-(2-Acetylamino-thiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (2.6 g) is obtained in the form of a pale beige crystalline powder whose characteristics are identical to those of the product obtained in Example 17.

Following the procedure described in Example 17, 3-(2-acetylamino-thiazol-5-yl)-2-carboxy-7-[(D)-α-t-butoxy-carbonylaminophenylacetamido]-8-oxo-5-thia-1-azabicyclo[4.2.0]oct-2-ene can subsequently be obtained.

Bromine (2.69 g) dissolved in dry methylene chloride (5 cc) is added, in 10 minutes, to a solution, cooled to −60° C., of 2-benzhydryloxycarbonyl-7-[(D)-α-t-butoxycarbonylaminophenylacetamido]-3-(2-dimethylamino-vinyl)-8-oxo-5-thia-1-azabicyclo[4.2.0]oct-2-ene, E-isomer, (11.3 g) in dry tetrahydrofuran (80 cc). The mixture is stirred for 45 minutes whilst allowing the temperature to rise to −15° C., and thereafter a mixture of distilled water (0.6 cc) and tetrahydrofuran (3 cc) is added. After 30 minutes at −15° C., a solution of thiorea (1.93 g) in a mixture of tetrahydrofuran (18 cc) and water (4 cc) is added. The reaction mixture is stirred for 4 hours at between 5° and 20° C., then diluted with ethyl acetate (500 cc) and washed with a half-saturated sodium bicarbonate solution (300 cc), water (300 cc) and a half-saturated sodium chloride solution (300 cc). The residue obtained [after drying the solution over sodium sulphate, filtering it and evaporating it under reduced pressure (30 mm Hg; 4 kPa) at 40° C.] is chromatographed on a column (height: 30 cm; diameter: 5 cm) of silica (0.04–0.06 mm), elution being carried out under 0.4 bar (40 kPa) with a 35:65 (by volume) mixture of cyclohexane and ethyl acetate and 100 cc fractions being collected. Fractions 18 to 31, containing the pure product, are combined and concentrated to dryness under reduced pressure (30 mm Hg; 4 kPa) at 40° C. 3-(2-Amino-thiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (2.08 g) is obtained in the form of an orange froth.

Infra-red spectrum (CHBr₃): characteristic bands (cm⁻¹) at 3480, 3390, 3200, 1785, 1715, 1695, 1600, 1495, 1455, 1390, 1370, 1220, 760 and 740.

Proton nuclear magnetic resonance spectrum (350 MHz, CDCl₃, δ in ppm, J in Hz): 1.43 (s, 9H, —C(CH₃)₃); 3.36 and 3.55 (2d, J=18, 2H, —S—CH₂—); 4.94 (s broad, 2H, —NH₂); 4.98 (d, J=5, 1H, —H in the 6-position);

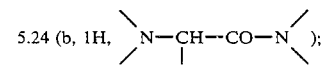
5.24 (b, 1H, \N—CH—CO—N/);

5.67 (d, J = 6, 1H, —NH—C—O—);
                                ‖
                                O 5.83 (dd, J=5 and 9, 1H, —H in the 7-position); 6.73 (b, 1H, —CO—NH—); 6.83 (s, 1H, —COO—CH(C₆H₅)₂); 6.94 (s, 1H, —H of the triazole); 7.10 to 7.50 (m, 15H, aromatic protons).

EXAMPLE 23

Tritylaminoacetyl chloride hydrochloride (4.02 g) is added to a solution of 3-(2-amino-thiazol-5-yl)-2-benzhydryloxycarbonyl-7-(3,4-dichlorophenylthio)-acetamido-8-oxo-5-thia-1-azabicyclo[4.2.0]oct-2-ene (2.05 g) in tetrahydrofuran (60 cc), cooled to 3° C., and triethylamine (3.36 cc) is then added in 5 minutes. After 30 minutes at 3° C., the reaction mixture is diluted with ethyl acetate (250 cc), washed successively with distilled water (150 cc), 0.1N hydrochloric acid (100 cc), saturated sodium bicarbonate solution (100 cc), distilled water (100 cc) and a saturated sodium chloride solution (100 cc). The organic phase is dried over sodium sulphate and concentrated to dryness under reduced pressure (30 mm Hg; 4 kPa) at 40° C., and the residue is chromatographed on a column (height: 30 cm, diameter: 4 cm) of silica gel (0.02–0.04 mm), elution being carried out under a pressure of 0.5 bar (50 kPa) with a mixture of cyclohexane and ethyl acetate (65:35 by volume), and 60 cc fractions being collected. Fractions 4 to 35, containing the pure product, are combined and concentrated to dryness under reduced pressure (30 mm Hg; 4 kPa) at 30° C., to give 2-benzhydryloxycarbonyl-7-(3,4-dichlorophenyl-thio)acetamido-8-oxo-3-(2-tritylaminoacetamido-thiazol-5-yl)-5-thia-1-azabicyclo[4.2.0]oct-2-ene (1.51 g) in the form of a white powder.

Infra-red spectrum (CHBr₃): characteristic bands (cm⁻¹) at 3350, 1785, 1725, 1685, 1535, 1500, 1460, 1450, 860, 810 and 750.

2-Benzhydryloxycarbonyl-7-(3,4-dichlorophenylthio)-acetamido-8-oxo-3-(2-tritylaminoacetamido-thiazol-5-yl)-5-thia-1-azabicyclo[4.2.0]oct-2-ene (1.61 g) is treated with formic acid (30 cc) and distilled water (3 cc) at 50° C. for 30 minutes and then concentrated to dryness under reduced pressure (2 mm Hg; 0.27 kPa) at 40° C. The residue is treated in accordance with the working method described in Example 24, to give 2-carboxy-7-(3,4-dichlorophenylthio)-acetamido-3-(2-glycylamino-thiazol-5-yl)-8-oxo-5-thia-1-azabicyclo[4.2.0]oct-2-ene (0.46 g) in the form of a yellow powder.

Proton nuclear magnetic resonance spectrum (250 MHz, d₆-DMSO, δ in ppm, J in Hz):

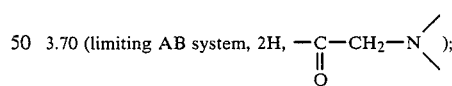
3.70 (limiting AB system, 2H, —C—CH₂—N );
                                     ‖
                                     O

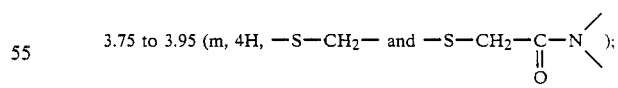
3.75 to 3.95 (m, 4H, —S—CH₂— and —S—CH₂—C—N );
                                          ‖
                                          O 5.07 (d, J=5, 1H, —H in the 6-position); 5.57 (dd, J=8 and 5, 1H, —H in the 7-position); 7.34 (dd, J=8.5 and 2, 1H, aromatic —H in the 6-position); 7.46 (s, 1H, —H of the thiazole); 7.55 (d, J=8.5, 1H, aromatic —H in the 5-position); 7.65 (d, J=2, 1H, aromatic —H in the 2-position);

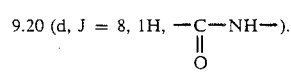
9.20 (d, J = 8, 1H, —C—NH—).
                    ‖
                    O 3-(2-Amino-thiazol-5-yl)-2-benzhydroxycarbonyl-7-(3,4-dichlorophenylthio)-acetamido-8-oxo-5-thia-1-azabicyclo[4.2.0]oct-2-ene can be prepared in the following manner:

Sodium bicarbonate (1.34 g), followed by a solution of thiourea (1.21 g) in a mixture of tetrahydrofuran (10 cc) and distilled water (10 cc), is added to a solution of 2-benzhydrocarbonyl-3-(2-chloroacetamido-thiazol-5-yl)-7-(3,4-dichlorophenylthio)-acetamido-8-oxo-5-thia-1-azabicyclo[4.2.0]oct-2-ene (11.17 g) in tetrahydrofuran (100 cc), and the reaction mixture is stirred for 3 days at 25° C. It is then diluted with ethyl acetate (300 cc) and washed with distilled water (2×200 cc) and with a saturated sodium chloride solution (100 cc). The organic phase is dried over sodium sulphate and concentrated to dryness under reduced pressure (30 mm Hg; 4 kPa) at 40° C. The residue is chromatographed on a column (diameter: 3 cm) of silica gel (0.05–0.2 mm) (140 g), elution being carried out with a mixture of cyclohexane and ethyl acetate (20:80 by volume), and 120 cc fractions being collected. Fractions 5 to 14 are combined and concentrated to dryness under reduced pressure (30 mm Hg; 4 kPa) at 30° C. to give 3-(2-amino-thiazol-5-yl)-2-benzhydryloxycarbonyl-7-(3,4-dichlorophenylthio)-acetamido-8-oxo-5-thia-1-azabicyclo[4.2.0]oct-2-ene (8 g) in the form of a pale yellow froth.

Rf=0.26 (silica gel chromatographic plate, eluted with a mixture of cyclohexane and ethyl acetate (20:80 by volume)).

EXAMPLE b 24

N,N-Diisopropylethylamine (0.17 cc) and N-t-butoxycarbonylcysteamine (0.265 g) dissolved in N,N-dimethylformamide (5 cc) are added to a solution of 2-benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene-5-oxide (0.77 g) in N,N-dimethylformamide (10 cc) at 20° C. The reaction mixture is stirred for 17 hours at 20° C. and then diluted with ethyl acetate (100 cc) and distilled water (100 cc). The organic phase is washed with saturated sodium chloride solution (100 cc), dried over sodium sulphate and concentrated to dryness under reduced pressure (30 mm Hg; 4 kPa) at 40° C. The yellow solid obtained is triturated with ethyl ether (10 cc), filtered and crystallized from acetonitrile (10 cc) to give 2-benzhydryloxycarbonyl-3-[2-(2-t-butoxycarbonylamino-ethylthioacetamido)-thiazol-5-yl]-7-(3,4-dichlorophenylthio)-acetamido-8-oxo-5-thia-1-azabicyclo[4.2.0]oct-2-ene-5-oxide (0.42 g) in the form of a yellow crystalline solid.

Infra-red spectrum (KBr): characteristic bands (cm$^{-1}$) at 1795, 1720, 1690, 1540, 1510, 1170, 870, 815, 760 and 705.

Proton nuclear magnetic resonance spectrum (250 MHz, d$_6$-DMSO, δ in ppm, J in Hz): 1.39 (s, 9H, —C(CH$_3$)$_3$); 2.67 (t, J=7, 2H, —S—C$\underline{H}_2$—CH$_2$—); 3.17 (td, J=7 and 6, 2H, —S—CH$_2$—C$\underline{H}_2$—NH—); 3.42 (s, 2H, >N—CO—CH$_2$S—CH$_2$—); 3.74 and 4.31 (2d, J=18, 2H, —S—CH$_2$—); 3.9 and 4.01 (2d, J=15, 2H, Ar—S—CH$_2$—CO—N<); 5.01 (d, J=5, 1H, —H in the 6-position); 5.97 (dd, J=5 and 9, 1H, —H in the 7-position); 6.87 (s, 1H, —COO—CH(C$_6$H$_5$)$_2$); 6.93 (t, J=6, 1H, —CH$_2$—N$\underline{H}$—COO—); 7.05 to 7.35 (m, 10H, aromatic protons); 7.36 (s and dd, J=8.5 and 2, 2H, —H of the thiazole and aromatic —H in the 6-position, respectively); 7.55 (d, J=8.5, 1H, aromatic —H in the 5-position); 7.65 (d, J=2, 1H, aromatic —H in the 2-position);

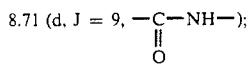
8.71 (d, J = 9, —C—NH—);

12.26 (b, 1H, —NHCO—).

A solution of 2-benzhydryloxycarbonyl-3-[2-(t-butoxycarbonylamino-ethylthioacetamido)-thiazol-5-yl]-7-(3,4-dichlorophenylthio)-acetamido-8-oxo-5-thia-1-azabicyclo[4.2.0]oct-2-ene-5-oxide (3.08 g) in a mixture of methylene chloride (50 cc) and N,N-dimethylacetamide (5 cc), cooled to 0° C., is treated with phosphorus trichloride (0.9 g) in the course of 30 minutes. The reaction mixture is poured into a mixture of distilled water (100 cc) and ethyl acetate (200 cc). The organic phase is washed with a saturated sodium chloride solution (100 cc), dried over sodium sulphate and concentrated to dryness under reduced pressure (30 mm Hg; 4 kPa) at 40° C. The residue is chromatographed on a column (diameter: 2 cm) of silica gel (0.05–0.2 mm) (70 g), elution being carried out with a mixture of cyclohexane and ethyl acetate (20:80 by volume) and 60 cc fractions being collected. Fractions 2 to 6 are combined and concentrated to dryness under reduced pressure (30 mm Hg; 4 kPa) at 30° C. to give 2-benzhydryloxycarbonyl-3-[2-(2-t-butoxycarbonylamino-ethylthioacetamido)-thiazol-5-yl]-7-(3,4-dichlorophenyl)-oacetamido-8-oxo-5-thia-1-azabicyclo[4.2.0]oct-2-ene (1.7 g in the form of a yellow froth.

Rf=0.33 (silica gel chromatographic plate, eluant: ethyl acetate).

Infra-red spectrum (KBr): characteristic bands (cm$^{-1}$) at 1795, 1720, 1690, 1540, 1510, 870, 815, 760 and 705.

Proton nuclear magnetic resonance spectrum (250 MHz, CDCl$_3$, δ in ppm, J in Hz): 1.44 (s, 9H, —C(CH$_3$)$_3$); 2.77 (t, J=7, 2H, —S—CH$_2$—CH$_2$—); 3.36 (m, 2H, —S—CH$_2$—CH$_2$—NH—);

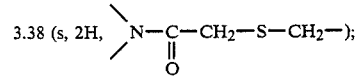
3.38 (s, 2H, N—C—CH$_2$—S—CH$_2$—);

3.51 and 3.65 (2d, J=18, 2H, —s—CH$_2$—); 3.66 and 3.76

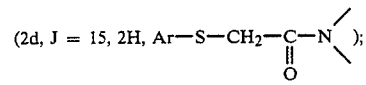
(2d, J = 15, 2H, Ar—S—CH$_2$—C—N );

5.02 (d, J=5, 1H, —H in the 6-position); 5.1 (b, 1H, —CH$_2$—NH—COO—); 5.86 (dd, J=9 and 5, 1H, —H in the 7-position); 6.91 (s, 1H, —COO—CH(C$_6$H$_5$)$_2$) 7.05 to 7.35 (m, aromatic protons, aromatic —H in the 6-position, >NH); 7.11 (s, —H of the thiazole); 7.38 (d, J=8.5, 1H, aromatic —H in the 5-position); 7.48 (d, J=2, 1H, aromatic —H in the 2-position);

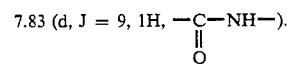
7.83 (d, J = 9, 1H, —C—NH—).

A solution of 2-benzhydryloxycarbonyl-3-[2-(2-t-butoxycarbonylamino-ethylthioacetamido)-thiazol-5-yl]-7-(3,4-dichlorophenylthio)-acetamido-8-oxo-5-thia-1-azabicyclo[4.2.0]oct-2-ene (1.7 g) in formic acid (50 cc) is heated at 50° C. for 30 minutes and then concentrated to dryness under reduced pressure (2 mm Hg; 0.27 kPa) at 40° C. The oil which remains is taken up in acetone (20 cc), which is concentrated to dryness under reduced pressure (40 mm Hg; 5.3 kPa) at 50° C.; this operation is repeated once more and the residue is then taken up in boiling acetone (20 cc). The mixture is filtered hot and the solid collected is washed with acetone (20 cc) and ethyl ether (20 cc), to give 3-[2-(2-aminoethylthioacetamido)-thiazol-5-yl]-2-carboxy-7-(3,4-dichlorophenylthio)-acetamido-8-oxo-5-thia-1-azabicyclo[4.2.0]oct-2-ene (1.15 g) in the form of a yellow solid.

Infra-red spectrum (KBr): characteristic bands (cm$^{-1}$) at 3260, 3150, 3100–2200, 1765, 1760, 1600, 1550, 1460, 880 and 810.

Proton nuclear magnetic resonance spectrum (250 MHz, d$_6$-DMSO, δ in ppm, J in Hz): 2.87 (m, 2H, —S—CH$_2$—CH$_2$—); 3.09 (m, 2H, —S—CH$_2$—CH$_2$—N>);

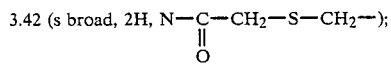

3.42 (s broad, 2H, N—C(=O)—CH$_2$—S—CH$_2$—);

3.66 and 3.76 (2d, J=18, 2H, —S—CH$_2$—); 3.78 and 3.88

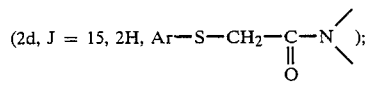

(2d, J = 15, 2H, Ar—S—CH$_2$—C(=O)—N<);

5.06 (d, J=5, 1H, —H in the 6-position); 5.55 (dd, J=5 and 9, 1H, —H in the 7-position); 7.33 (dd, J=8.5 and 2, 1H, aromatic —H in the 6-position); 7.48 (s, 1H, —H of the thiazole); 7.53 (d, J=8.5, 1H, aromatic —H in the 5-position); 7.64 (d, J=2, 1H, aromatic —H in the 2-position);

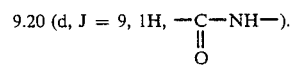

9.20 (d, J = 9, 1H, —C(=O)—NH—).

2-Benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene-5-oxide can be obtained in the following manner:

A solution of 2-benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene (2 g) in methylene chloride (50 cc) is cooled to 0° C. and treated with an 85% strength solution of meta-chloroperbenzoic acid (0.45 g) in methylene chloride (10 cc). After 30 minutes at a temperature of between 0° and 5° C., the reaction mixture is diluted with methylene chloride (100 cc) and a saturated sodium bicarbonate solution (100 cc) is added. The solid which precipitates is filtered off and taken up in methylene chloride (200 cc). The decanted organic phase is added to this solution, after having been washed with water (100 cc) and then with a saturated sodium chloride solution (100 cc) and dried over sodium sulphate, and the mixture is then concentrated under reduced pressure to a residual volume of 10 cc. The solid is filtered off and washed with ethyl acetate (20 cc) and then with ethyl ether (20 cc). 2-Benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene-5-oxide (1.48 g) is obtained in the form of a cream solid.

Infra-red spectrum (KBr): characteristic bands (cm$^{-1}$) at 3280, 3180, 3100, 2500, 1780, 1715, 1685, 1650, 1540, 1510, 1460, 1220, 850, 810, 755 and 700.

Proton nuclear magnetic resonance spectrum (250 MHz, d$_6$-DMSO, δ in ppm, J in Hz): 3.74 and 4.33 (2d, J=18, 2H, —S—CH$_2$—); 3.90 and 4.33 (2d, J=15, 2H, —S—CH$_2$—CO—N>); 4.38 (s, 2H, >N—CO—CH$_2$—Cl); 5.01 (d, J=5, 1H, —H in the 6-position); 5.98 (dd, J=5 and 9, 1H, —H in the 7-position); 6.88 (s, 1H, —COOCH(C$_6$H$_5$)$_2$); 7.05 to 7.35 (m, 10H, aromatic protons); 7.37 (dd, J=8.5 and 2, 1H, aromatic —H in the 6-position); 7.39 (s, 1H, —H of the thiazole); 7.56 (d, J=8.5, 1H, aromatic —H in the 5-position); 7.67 (d, J=2, 1H, aromatic —H in the 2-position); 8.72 (d, J=9, 1H, —CO—NH—); 12.5 (b smudged, 1H, >NH).

2-Benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene can be prepared in the following manner:

A solution of p-toluenesulphonic acid (hydrate) (11.4 g) in acetonitrile (70 cc) is added, in 40 minutes, to a suspension of 2-benzhydryloxycarbonyl-7-t-butoxycarbonylamino-3-(2-chloroacetamido-thiazol-5-yl)-8-oxo-5-thia-1-azabicyclo[4.2.0]oct-2-ene (19.2 g) in acetonitrile (290 cc) at 37° C. The mixture is stirred for 3 hours at 40° C., p-toluenesulphonic acid (5.7 g) is then added, and the reaction mixture is stirred for a further hour before it is diluted with ethyl acetate (500 cc) and a saturated sodium bicarbonate solution (300 cc). The organic phase is washed with distilled water (2×250 cc) and with a half-saturated sodium chloride solution (250 cc) and is dried over sodium sulphate, after which it is cooled to 0° C. before triethylamine (4.2 cc) is added. A solution of 3,4-dichlorophenylthioacetyl chloride (7.6 g) in ethyl acetate (50 cc) is then added in 10 minutes. The mixture is stirred for 35 minutes whilst allowing the temperature to rise to 18° C. and is then diluted with ethyl acetate (100 cc) and distilled water (400 cc). The organic layer is washed with a mixture of saturated sodium chloride solution (150 cc) and saturated sodium bicarbonate solution (150 cc), and thereafter with normal hydrochloric acid (300 cc) and with a saturated sodium chloride solution (300 cc). After having been dried over magnesium sulphate, the solution is concentrated to dryness under reduced pressure (30 mm Hg; 4 kPa) at 40° C. and the residue is chromatographed on a column (height: 77 cm, diameter: 4.5 cm) of silica gel (0.2–0.06 mm), elution being carried out with a 50:50 (by volume) mixture (1.8 liters) of cyclohexane and ethyl acetate, and then with a 20:80 (by volume) mixture, and 600 cc fractions being collected. Fractions 4 to 6, containing the product, are combined and concentrated under reduced pressure (30 mm Hg; 4 kPa) at 30° C. to give a solid (14.6 g) which is recrystallised from acetonitrile (50 cc) to give 2-benzhydryloxycarbonyl-3-(2-chloroacetamido-thiazol-5-yl)-7-(3,4-dichlorophenylthio)-acetamido-8-oxo-5-thia-1-azabicyclo[4.2.0]oct-2-ene (9.2 g) in the form of cream crystals.

Melting point =148° C.

2-Benzhydryloxycarbonyl-7-t-butoxycarbonylamino-3-(2-chloroacetamido-thiazol-5-yl)-8-oxo-5-thia-1-azabicyclo[4.2.0]oct-2-ene can be obtained in the following manner:

Chloroacetyl chloride (12.37 g) is added to a solution of 3-(2-amino-thiazol-5-yl)-2-benzhydryloxycarbonyl-7-t-butoxycarbonylamino-8-oxo-5-thia-1-azabicyclo[4.2.-

0]oct-2-ene (60 g) in tetrahydrofuran (350 cc) cooled to 0° C., and triethylamine (16.3 cc) is then added in 6 minutes. After 1 hour at 0° C., the reaction mixture is diluted with a half-saturated sodium bicarbonate solution (800 cc) and extracted with ethyl acetate (3×200 cc). The combined organic phases are washed with a saturated sodium chloride solution (250 cc) and dried, after which they are concentrated to dryness under reduced pressure (30 mm Hg; 4 kPa) at 40° C. to give an orange froth (78 g) which is recrystallised from acetonitrile (300 cc) to give cream crystals (37.4 g) of 2-benzhydryloxycarbonyl-7-t-butoxycarbonylamino-3-(2-chloroacetamido-thiazol-5-yl)-8-oxo-5-thia-1-azabicyclo[4.2.0]oct-2-ene Melting point = 244° C.

EXAMPLE 25

On treating 2-benzhydryloxycarbonylamino-3-(2-chloroacetamido-thiazol-5-yl)-7-(3,4-dichlorophenylthio)-acetamido-8-oxo-5-thia-1-azabicyclo[4.2.0]oct-2-ene-5-oxide (4.2 g) with benzhydryl (L)-N-t-butoxycarbonylamino-cysteinate (3.13 g) in the presence of N,N-diisopropylethylamine (0.93 cc), crude 2-benzhydryloxycarbonyl-3-{2-[(L)-2-benzhydryloxycarbonyl-2-t-butoxycarbonylamino-ethylthioacetamido]-thiazol-5-yl}-7-(3,4-dichlorophenylthio)-acetamido-8-oxo-5-thia-1-azabicyclo[4.2.0]oct-2-ene-5-oxide (7.61 g) is obtained in the form of a brown oil which is reduced by the action of phosphorus trichloride (0.87 cc) in accordance with the working method of Example 24, to give 2-benzhydryloxycarbonyl-3-{2-[(L)-2-benzhydryloxycarbonyl-2-t-butoxycarbonylamino-ethylthioacetamido]-thiazol-5-yl}-7-(3,4-dichlorophenylthio)-acetamido-8-oxo-5-thia-1-azabicyclo[4.2.0]oct-2-ene (3.8 g) in the form of a yellow froth.

Rf=0.63 (silica gel chromatographic plate, eluted with a 20:80 (by volume) mixture of cyclohexane and ethyl acetate).

2-Benzhydryloxycarbonyl-3-{2-[(L)-2-benzhydryloxycarbonyl-2-t-butoxycarbonylamino-ethylthioacetamido]-thiazol-5-yl}-7-(3,4-dichlorophenylthio)-acetamido-8-oxo-5-thia-1-azabicyclo[4.2.0]oct-2-ene (3.80 g) is treated with formic acid (50 cc) in accordance with the working method described in Example 24 to give 3-{2-[(L)-2-amino-2-carboxy-ethylthioacetamido]-thiazol-5-yl}-2-carboxy-7-(3,4-dichlorophenylthio)-acetamido-8-oxo-5-thia-1-azabicyclo[4.2.0]oct-2-ene (1.79 g) in the form of a cream powder.

Infra-red spectrum (KBr): characteristic bands (cm$^{-1}$) at 3300-2200, 1770, 1660, 1550, 1460, 870 and 810.

Proton nuclear magnetic resonance spectrum (250 MHz, d$_6$-DMSO, δ in ppm, J in Hz): 2.98 and 3.16 (2dd, J=14 and 7.5 and J=14 and 4 respectively, —S—CH$_2$—CH(NH$_2$)COOH); 3.50 (limiting AB system, J=15, 2H, —S—CH$_2$—CO—N>);

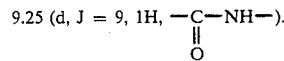

3.68 (dd, J = 7.5 and 4, 1H, —CH—COO—);

3.73 and 3.86 (2d, J=18, 2H, —S—CH$_2$—); 3.77 and 3.86

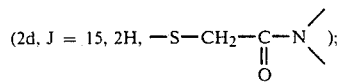

(2d, J = 15, 2H, —S—CH$_2$—C—N );

5.13 (d, J=5, 1H, —H in the 6-position); 5.67 (dd, J=5 and 9, 1H, —H in the 7-position); 7.33 (dd, J=8.5 and 2, 1H, aromatic —H in the 6-position); 7.51 (s, 1H, —H of the thiazole); 7.53 (d, J=8.5, 1H, aromatic —H in the 5-position); 7.63 (d, J=2, 1H, aromatic —H in the 2-position);

9.25 (d, J = 9, 1H, —C—NH—).

EXAMPLE 26

A mixture of 2-benzhydryloxycarbonyl-8-oxo-3-[2-(pyrid-3-ylmethyl)-thiazol-5-yl]-7-(thien-2-ylacetamido)-5-thia-1-azabicyclo[4.2.0]oct-2-ene (1.32 g), methyl iodide (1.25 cc) and dimethylformamide (7 cc) is stirred at 20° C. for 12 hours. The mixture is diluted with diethyl ether (100 cc) and this mixture is stirred for 15 minutes. The supernatant liquor is decanted and the residue is stirred for 15 minutes with ethyl ether (100 cc). The solid is filtered off, washed with diethyl ether (2×20 cc) and dried under reduced pressure (0.1 mm Hg; 0.013 kPa) at 20° C. 2-Benzhydryloxycarbonyl-3-[2-(1-methyl-3-pyridinio)-methylthiazol-5-yl]-8-oxo-7-(thien-2-yl-acetamido)-5-thia-1-azabicyclo[4.2.0]oct-2-ene iodide (2.3 g) is thus obtained in the form of an orange powder.

Infra-red spectrum (KBr): characteristic bands (cm$^{-1}$) at 3260, 3180, 1780, 1730, 1665, 1510, 1225, 750, 705 and 675.

Proton nuclear magnetic resonance spectrum (350 MHz, d$_6$-DMSO, δ in ppm, J in Hz):

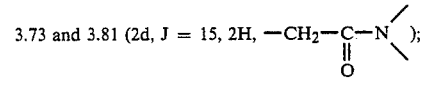

3.73 and 3.81 (2d, J = 15, 2H, —CH$_2$—C—N );

3.8 and 3.9 (2d, J=18, 2H, —S—CH$_2$—); 4.36 (s, 3H, >+N—CH$_3$); 4.44 (s, 2H, —CH$_2$—); 5.23 (d, J=5, 1H, —H in the 6-position); 5.83 (dd, J=9 and 5, 1H, —H in the 7-position); 6.86 (s, 1H, —COO—CH(C$_6$H$_5$)$_2$); 6.9 to 7 (m, 2H, —H in the 3-position and —H in the 4-position of the thiophene); 6.9 to 7.4 (m, aromatic protons and —H in the 5-position of the thiophene); 7.64 (s, 1H, —H of the thiazole); 8.12 (dd, J=8 and 5, 1H, —H in the 5-position of the pyridine); 8.46 (d, J=8, 1H, —H in the 4-position of the pyridine); 8.94 (d, J=5, 1H, —H in the 6-position of the pyridine); 9.05 (s, 1H, —H in the 2-position of the pyridine)

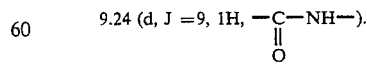

9.24 (d, J =9, 1H, —C—NH—).

Trifluoroacetic acid (18 cc) is added to a solution, cooled to 3° C., of 2-benzhydryloxycarbonyl-3-[2-(1-methyl-3 pyridinio)-methyl-thiazol-5-yl]-8-oxo-7-(thien-2-yl-acetamido)-5-thia-1-azabicyclo[4.2.0]oct-2-ene iodide (1.5 g) in anisole (1.8 cc). The mixture is stirred at 3° C. for 15 minutes and then at 20° C. for 30 minutes.

It is concentrated under reduced pressure (0.1 mm Hg; 0.013 kPa) at 20° C. The residue is taken up in ethyl acetate (50 cc) and the solution is concentrated to dryness under reduced pressure (0.1 mm Hg; 0.013 kPa). The operation is repeated and the residue is taken up in ethyl ether (50 cc). The heterogeneous mixture is stirred for 15 minutes at 22° C. and is filtered, and the solid is dried under reduced pressure (0.1 mm Hg; 0.013 kPa). 2-Carboxy-3-[2-(1-methyl-3-pyridinio)-methyl-thiazol-5-yl]-8-oxo-7-(thien-2-yl-acetamido)-5-thia-1-azabicyclo[4.2.0]oct-2-ene trifluoroacetate (1.05 g) is obtained in the form of a yellow powder.

Infra-red spectrum (KBr): characteristic bands (cm$^{-1}$) at 3300, 1780, 1680, 1510, 1180, 800, 720 and 680.

Proton nuclear magnetic resonance spectrum (350 MHz, d$_6$-DMSO, δ in ppm, J in Hz): 3.7 to 3.85

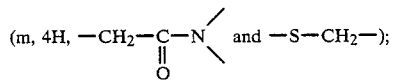

(m, 4H, —CH$_2$—C(=O)—N< and —S—CH$_2$—);

4.35 (s, 3H, ≥$_{30}$ N—CH$_3$); 4.62 (s, 2H, —CH$_2$—); 5.18 (d, J=5, 1H, —H in the 6-position); 5.75 (dd, J=8 and 5, 1H, —H in the 7-position); 6.9 to 7 (m, 2H, —H in the 3-position and —H in the 4-position of the thiophene); 7.34 (dd, J=5 and 1, 1H, —H in the 5-position of the thiophene); 7.75 (s, 1H, —H of the thiazole); 8.11 (dd, J=8 and 5, 1H, —H in the 5-position of the pyridine); 8.56 (d, J=8, 1H, —H in the 4-position of the pyridine); 8.92 (d, J=5, 1H, —H in the 6-position of the pyridine); 9.08 (s broad, 1H, —H in the 2-position of the pyridine);

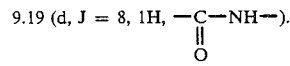

9.19 (d, J = 8, 1H, —C(=O)—NH—).

2-Benzhydryloxycarbonyl-8-oxo-3-[2-(pyrid-3-yl-methyl)-thiazol-5-yl]-7-(thien-2-yl-acetamido)-5-thia-1-azabicyclo[4.2.0]oct-2-ene can be prepared in the following manner:

Thien-2-yl-acetyl chloride (1.4 cc) is added to a solution of 7-amino-2-benzhydryloxycarbonyl-8-oxo-3-[2-(pyrid-3-ylmethyl)-thiazol-5-yl]-5-thia-1-azabicyclo[4.2.0]oct-2-ene (6.36 g) in dry tetrahydrofuran (200 cc), and triethylamine (1.58 cc) is then added. The mixture is stirred at 20° C. for 1 hour 20 minutes and is then poured into a 65:35 (by volume) mixture of ethyl acetate and a saturated sodium bicarbonate solution. The organic phase is decanted and then washed successively with distilled water (200 cc), and a saturated sodium chloride solution (200 cc) and dried over anhydrous sodium sulphate. The drying agent is filtered off and washed with ethyl acetate (10 cc) and the filtrate is concentrated to dryness under reduced pressure (20 mm Hg; 2.7 kPa) at 30° C. The residue is purified by chromatography on a column (height: 24 cm, diameter: 3 cm) of silica gel (0.05–0.2 mm), elution being carried out with ethyl acetate (2.5 liters), and 60 cc fractions being collected. Fractions 12 to 35 are combined and concentrated to dryness under reduced pressure (30 mm Hg; B 4 kPa) at 30° C. to give 2-benzhydryloxycarbonyl-8-oxo-3-[2-(pyrid-3-ylmethyl)-thiazol-5-yl]-7-(thien-2-yl-acetamido)-5-thia-1-azabicyclo[4.2.0]oct-2-ene (4.45 g) in the form of a yellow froth.

Infra-red spectrum (KBr): characteristic bands (cm$^{-1}$) at 3300, 3200, 1785, 1730, 1685, 1580, 1520, 1495, 1480, 1450, 1425, 1225, 760 and 700.

Proton nuclear magnetic resonance spectrum (250 MHz, d$_6$-DMSO, δ in ppm, J in Hz): 3.78 (limiting AB system, J=16, 2H, —CH$_2$—CO—N<); 3.78 and 3.9 (2d, J=18, 2H, —S—CH$_2$—); 4.14 and 4.24 (2d, J=17, 2H, —CH$_2$—); 5.21 (d, J=5, 1H, —H in the 6-position); 5.83 (dd, J=8 and 5, 1H, —H in the 7-position); 6.85 (s, 1H, —COO—CH(C$_6$H$_5$)$_2$); 6.9 to 7 (m, 2H, —H in the 3-position and —H in the 4-position of the thiophene); 7.05 to 7.4 (m, 12H, aromatic protons+—H in the 5-position of the thiophene and —H in the 5-position of the pyridine); 7.58 (s, 1H, —H of the thiazole); 7.64 (d broad, J=7.5, 1H, —H in the 4-position of the pyridine); 8.50 (m, 2H, —H in the 2-position and 13 H in the 6-position of the pyridine); 9.23 (d, J=8, 1H, —CO—NH—).

7-Amino-2-benzhydryloxycarbonyl-8-oxo-3-[2-(pyrid-3-ylmethyl)-thiazol-5-yl]-5-thia-1-azabicyclo[4.2.0]oct-2-ene can be prepared in the following manner:

A solution of methanesulphonic acid (10 cc) is added to a solution of 2-benzhydroxycarbonyl-7-t-butoxycarbonylamino-8-oxo-3-[2-(pyrid-3-ylmethyl)-thiazol-5-yl]-5-thia-1-azabicyclo[4.2.0]oct-2-ene (10 g) in acetonitrile (100 cc). The mixture is stirred for 5 minutes and is poured into a 50:50 (by volume) mixture (500 cc) of saturated sodium bicarbonate solution and ethyl acetate. The organic phase is decanted and then washed successively with distilled water (200 cc) and saturated sodium chloride solution (200 cc). It is dried over anhydrous magnesium sulphate and filtered, and the filtrate is concentrated to dryness under reduced pressure (30 mm Hg; 4 kPa) at 30° C. 7-Amino-2-benzhydryloxycarbonyl-8-oxo-3-[2-(pyrid-3-yl-methyl)-thiazol-5-yl]-5-thia-1-azabicyclo[4.2.0]oct-2-ene (6.36 g) is obtained in the form of a chestnut-coloured froth.

Infra-red spectrum (CHBr$_3$): characteristic bands (cm$^{-1}$) at 3400, 3340, 1780, 1725, 1620, 1495, 1480, 1450, 1425, 1220 and 760.

Proton nuclear magnetic resonance spectrum (250 MHz, d$_6$-DMSO, δ in ppm, J in Hz); 3.72 and 3.83 (2d, J=18, 2H, —S—CH$_2$—); 4.13 and 4.23 (2d, J=16, 2H, —CH$_2$—); 4.89 (d, J=5, 1H, —H in the 7-position); 5.08 (d, J=5, 1H, —H in the 6-position); 6.8 (s, 1H, —COO—CH(C$_6$H$_5$)$_2$); 7.05 to 7.4 (m, aromatic protons, —NH$_2$ and —H in the 5-position of the pyridine); 7.53 (s, 1H, —H of the thiazole); 7.64 (ddd, J=8–2.5 and 1, 1H, —H in the 4-position of the pyridine); 8.47 (dd, J=5 and 1, 1H, —H in the 6-position of the pyridine); 8.49 (d, J=2, 1H, —H in the 2-position of the pyridine).

2-Benzhydryloxycarbonyl-7-t-butoxycarbonylamino-8-oxo-3-[2-(pyrid-3-ylmethyl)-thiazol-5-yl]-5-thia-1-azabicyclo[4.2.0]oct-2-ene can be prepared in the following manner:

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the epimeric bromoaldehydes) (88.1 g) in anhydrous tetrahydrofuran (150 cc) is added to a solution of pyrid-3-yl-thioformamide (25 g) in N,N'-dimethylacetamide (200 cc). The mixture is stirred for 6 hours at 20° C. and then poured into a 50:50 (by volume) mixture (2 liters) of water and ethyl acetate. The organic phase is decanted and then washed successively with saturated sodium bicarbonate solution (500 cc), water (250 cc) and saturated sodium chloride solution (250 cc). It is dried over anhydrous magnesium sulphate and filtered, and the filtrate is concentrated to dryness under reduced pressure (30 mm Hg; 4 kPa). The residue is purified by chromatography on a column (height: 60 cm, diameter: 6 cm) of silica gel (0.05–0.2 mm), elution being carried out with ethyl acetate (7 liters) and 120 cc fractions being collected. The contents of fractions 18 to 56 are concentrated to dryness under reduced pressure (30 mm Hg; 4 kPa) at 30° C., and 2-benzhydryloxycarbonyl-7-t-butoxycarbonylamino-8-oxo-3-[2-(pyrid-3-ylmethyl)-thiazol-5-yl]-5-thia-1-azabicyclo[4.2.0]oct-2-ene (26.74 g) is obtained in the form of a cream-coloured froth.

Infra-red spectrum (CHBr$_3$): characteristic bands (cm$^{-1}$) at 3420, 1785, 1720, 1500, 1455, 1425, 1390, 1240 and 760.

Proton nuclear magnetic resonance spectrum (250 MHz, CDCl$_3$, δ in ppm, J in Hz): 1.47 (s, 9H, —C(CH$_3$)$_3$); 3.48 and 3.67 (2d, J=18, 2H, —S—CH$_2$—); 4.1 (limiting AB system, J=16, 2H, —CH$_2$—); 5.04 (d, J=5, 1H, —H in the 6-position);

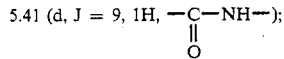

5.71 (dd, J=5 and 9, 1H, —H in the 7-position); 6.9 (s, 1H, —COO—CH(C$_6$H$_5$)$_2$); 7.05 to 7.4 (m, aromatic protons and —H in the 5-position of the pyridine); 7.39 (s, 1H, —H of the thiazole); 7.53 (ddd, J=8–2.5 and 1, 1H, —H in the 4-position of the pyridine); 8.50 (d, J=2.5, 1H, —H in the 2-position of the pyridine); 8.53 (dd, J=5 and 1, 1H, —H in the 6-position of the pyridine).

Pyrid-3-yl-thioacetamide can be prepared in the following manner:

A stream of hydrogen sulphide is bubbled for 6 hours through a solution of pyrid-3-yl-acetonitrile (50 g) and triethylamine (54 cc) in absolute ethanol (500 cc). The mixture is left to stand for 48 hours and a stream of nitrogen is then passed through it. The mixture is then concentrated to dryness under reduced pressure (30 mm Hg; 4 kPa) and the residual oil is taken up in ethanol (150 cc). This mixture is heated under reflux and filtered, and crystallisation occurs on cooling. The crystals are filtered off, washed with ethanol (10 cc) and then dried under reduced pressure (0.1 mm Hg; 0.013 kPa). Pyrid-3-yl-thioacetamide (52 g) is obtained in the form of a white crystalline powder.

Instantaneous melting point (Kofler method): 135°–136° C.

Proton nuclear magnetic resonance spectrum (60 MHz, d$_6$-DMSO, δ in ppm, J in Hz): 3.9 (s, 2H, —CH$_2$—); 7.38 (q, J=8 and 5, 1H, —H in the 5-position); 7.75 (dd, J=8 and 2, 1H, —H in the 4-position); 8.50 (dd, J=5 and 2, 1H, —H in the 6-position); 8.60 (d, J=2, 1H, —H in the 2-position); 9.50 (s broad, 2H, —NH$_2$).

EXAMPLE 27

A solution of 2-benzhydryloxycarbonyl-8-oxo-3-[2-(pyrid-3-ylamino)-thiazol-5-yl]-7-(thien-2-yl-acetamido)-5-thia-1-azabicyclo[4.2.0]oct-2-ene (0.3 g) and methyl iodide (0.3 cc) in N,N-dimethylformamide (6 cc) is stirred for 72 hours at 23° C. The reaction mixture is diluted with methylene chloride (50 cc) and the organic phase is washed with distilled water (2×50 cc) and then dried over magnesium sulphate; it is filtered and the filtrate is concentrated to dryness under reduced pressure (30 mm Hg; 4 kPa) at 30° C. The residue is dissolved in acetonitrile (3 cc) and the solution obtained is poured onto isopropyl ether (20 cc). The precipitate is filtered off, washed with isopropyl ether (2×5 cc) and dried under reduced pressure (0.5 mm Hg; 0.067 kPa). 2-Benzhydryloxycarbonyl-8-oxo-3-[2-(1-methyl-3-pyridino)-amino-thiazol-5-yl]-7-(thien-2-yl-acetamido)-5-thia-1-azabicyclo[4.2.0]oct-2-ene (0.3 g) is obtained in the form of a yellow powder.

Infra-red spectrum (KBr): characteristic bands (cm$^{-1}$) at 3200–3100, 2500, 1780, 1730, 1670, 1530, 1510, 765, 750 and 705.

Proton nuclear magnetic resonance spectrum (250 MHz, d$_6$-DMSO, δ in ppm, J in Hz): 3.79 (limiting AB system, J=15, 2H, —CH$_2$—CO—NH—); 3.82 and 3.95 (2d, J=18, 2H, —S—CH$_2$—); 4.4 (s, 3H, ≧N$^+$—CH$_3$); 5.23 (d, J=5, 1H, —H in the 6-position); 5.83 (dd, J=5 and 9, 1H, —H in the 7-position); 6.91 (s, 1H, —COO—CH(C$_6$H$_5$)$_2$); 6.95 to 7.05 (m, —H in the 3-position and —H in the 4-position of the thiophene); 6.95 to 7.35 (m, aromatic protons and >N—H); 7.27 (s, —H of the thiazole); 7.38 (dd, J=4.5 and 1, 1H, —H in the 5-position of the thiophene); 8.05 (dd, J=7.5 and 5, 1H, —H in the 5-position of the pyridine); 8.40 (dd, J=8 and 1, 1H, —H in the 4-position of the pyridine); 8.60 (d broad, J=5, 1H, —H in the 6-position of the pyridine); 9.16 (s broad, 1H, —H in the 2-position of the pyridine); 9.26 (d, J=9, 1H, —CO—NH—).

A solution of 2-benzhydryloxycarbonyl-8-oxo-3-[2-(1-methyl-3-pyridinio)-amino-thiazol-5-yl]-7-(thien-2-yl-acetamido)-5-thia-1-azabicyclo[4.2.0]oct-2-ene (0.3 g) and anisole (1 cc) in formic acid (5 cc) is stirred at 50° C. for 30 minutes. The mixture is concentrated to dryness under reduced pressure (0.1 mm Hg; 0.013 kPa) and the residue is taken up in ethanol (3×30 cc) and concentrated to dryness under reduced pressure (0.1 mm Hg; 0.013 kPa) at 30° C. on each occasion. The final residue is taken up in acetone (30 cc), washed with diethyl ether (2×30 cc) and dried under reduced pressure (0.1 mm Hg; 0.013 kPa). 2-Carboxylato-3-[2-(1-methyl-3-pyridinio)-amino-thiazol-5-yl]-8-oxo-7-(thien-2-yl-acetamido)-5-thia-1-azabicyclo[4.2.0]oct-2-ene (0.13 g) is thus obtained in the form of an ochre solid.

Infra-red spectrum (KBr): characteristic bands (cm$^{-1}$) at 3320, 3140, 2000, 1770, 1675, 1600, 1525, 1505, 710 and 675.

Proton nuclear magnetic resonance spectrum (250 MHz, d$_6$-DMSO, δ in ppm, J in Hz): 3.77 (s, 2H, —CH$_2$—CO—NH—); 3.81 and 3.93 (2d, J=18, 2H, —S—CH$_2$—); 4.36 (s, 3H, >$_+$N—CH$_3$); 5.17 (d, J=5, 1H, —H in the 6-position); 5.73 (dd, J=9 and 5, 1H, —H in the 7-position); 6.9 to 7 (m, 2H, —H in the 3-position and —H in the 4-position of the thiophene); 7.33 (dd, J=4.5 and 1, 1H, —H in the 5-position of the thiophene); 7.49 (s, 1H, —H of the thiazole); 8 (dd, J=7.5 and 5, 1H, —H in the 5-position of the pyridine); 8.47 (d broad, J=7.5, 1H, —H in the 4-position of the pyridine); 8.55 (d, J=5, 1H, —H in the 6-position of the pyridine); 9.17 (d, J=9, 1H, —CO—NH—); 9.33 (s broad, 1H, —H in the 2-position of the pyridine); 11.55 (b, 1H, >NH); 15 to 12 (b smudged, 1H, —COOH).

2-Benzhydryloxycarbonyl-8-oxo-3-[2-(pyrid-3-yl-amino)-thiazol-5-yl]-7-(thien-2-yl-acetamido)-5-thia-1-azabicyclo[4.2.0]oct-2-ene can be obtained in the following manner:

Thien-2-yl-acetyl chloride (0.88 cc) and triethylamine (0.95 cc) are added successively to a solution, cooled to 5° C., of 7-amino-2-benzhydryloxycarbonyl-8-oxo-3-[2-(pyrid-3-yl-amino)-thiazol-5-yl]-5-thia-1-azabicyclo[4.2.0]oct-2-ene (3.85 g) in dry tetrahydrofuran (100 cc), and the mixture is then stirred for 35 minutes at the same temperature. The cooling bath is removed and the mixture is stirred for 1 hour 30 minutes at 23° C. The reaction mixture is poured onto a mixture (50:50 by volume) (400 cc) of ethyl acetate and saturated sodium bicarbonate solution. The phases are allowed to separate and the organic phase is washed successively with distilled water (200 cc) and a saturated sodium chloride solution (200 cc). It is dried over anhydrous magnesium sulphate and filtered, and the filtrate is concentrated to dryness under reduced pressure (30 mm Hg; 4 kPa) at 30° C. The residue is chromatographed on a column (height: 30 cm, diameter: 3 cm) of silica gel (0.6–0.04 mm), elution being carried out with ethyl acetate (2 liters) and 100 cc fractions being collected. Fractions 5 to 8, containing the pure product, are combined and concentrated under reduced pressure (30 mm Hg; 4 kPa) at 30° C. to give 2-benzhydryloxycarbonyl-8-oxo-3-[2-(pyrid-3-yl-amino)-thiazol-5-yl]-7-(thien-2-yl-acetamido)-5-thia-1-azabicyclo[4.2.0]oct-2-ene (1.3 g) in the form of a yellow froth.

Infra-red spectrum (KBr): characteristic bands (cm$^{-1}$) at 3380, 3150, 2000, 1780, 1730, 1670, 1590, 1550, 1530, 1490, 1225, 760, 750 and 700.

Proton nuclear magnetic resonance spectrum (250 MHz, CDCl$_3$, δ in ppm, J in Hz): 3.45 and 3.60 (2d, J=18, 2H, —S—CH$_2$—);

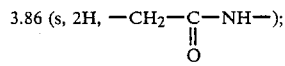
3.86 (s, 2H, —CH$_2$—C—NH—);
              ‖
              O 5.05 (d, J=5, 1H, —H in the 6-position); 5.89 (dd, J=5 and 9, 1H, —H in the 7-position);

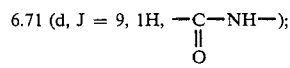
6.71 (d, J = 9, 1H, —C—NH—);
                    ‖
                    O 6.95 (s, 1H, —COO—CH(C$_6$H$_5$)$_2$); 6.95 to 7.35 (m, aromatic protons, —H in the 3-position, —H in the 4-position and —H in the 5-position of the thiophene, —H in the 5-position of the pyridine); 7.80 (ddd, J=8, 2 and 1, 1H, —H in the 4-position of the pyridine); 8.30 (dd, J=5 and 1, 1H, —H in the 6-position of the pyridine); 8.37 (b, 1H, >N—H); 8.47 (d, J=2, 1H, —H in the 2-position of the pyridine).

7-Amino-2-benzhydryloxycarbonyl-3-[2-(pyrid-3-yl-amino)-thiazol-5-yl]-8-oxo-5-thia-1-azabicyclo[4.2.0]oct-2-ene can be prepared in the following manner:

Methanesulphonic acid (37.7 cc) is added, in 5 minutes, to a solution of 2-benzhydryloxycarbonyl-7-t-butoxycarbonylamino-3-[2-(pyrid-3-yl-amino)-thiazol-5-yl]-8-oxo-5-thia-1-azabicyclo[4.2.0]oct-2-ene (37.22 g) in acetonitrile (372 cc). The mixture is stirred for 5 minutes and the reaction solution is then added to a mixture of saturated sodium bicarbonate solution (870 cc), distilled water (1740 cc) and methylene chloride (580 cc). The batch is stirred for 10 minutes and the precipitate is filtered off and washed with distilled water (4×100 cc). The product is dried and 7-amino-2-benzhydryloxycarbonyl-3-[2-(pyrid-3-yl-amino)-thiazol-5-yl]-8-oxo-5-thia-1-azabicyclo[4.2.0]oct-2-ene (27.66 g) is obtained in the form of a pale yellow crystalline powder.

Infra-red spectrum (KBr): characteristic bands (cm$^{-1}$) at 3380, 3150, 2000, 1780, 1730, 1670, 1590, 1550, 1530, 1490, 1225, 800, 760, 750 and 700.

Proton nuclear magnetic resonance spectrum (250 MHz, d$_6$-DMSO, δ in ppm, J in Hz): 2.4 (b, 2H, —NH$_2$); 3.78 (limiting AB system, J=18, 2H, —S—CH$_2$—); 4.88 (d, broad, J=5, 1H, —H in the 7-position); 5.1 (d, J=5, 1H, —H in the 6-position); 6.85 (s, 1H, —COO—CH(C$_6$H$_5$)$_2$); 7 to 7.35 (m, 11H, aromatic protons and —H of the thiazole); 7.34 (m, 1H, —H in the 5-position of the pyridine); 8.06 (ddd, J=8–2.5 and 1, 1H, —H in the 4-position of the pyridine); 8.17 (dd, J=5 and 1, 1H, —H in the 6-position of the pyridine); 8.68 (d, J=2.5, 1H, —H in the 2-position of the pyridine); 10.38 (b, 1H, —NH—).

2-Benzhydryloxycarbonyl-7-t-butoxycarbonylamino-3-[2-(pyrid-3-yl-amino)-thiazol-5-yl]-8-oxo-5-thia-1-azabicyclo[4.2.0]oct-2-ene can be prepared in the following manner:

A solution of bromine (35.96 g) in dry methylene chloride (40 cc) is added dropwise to a solution, cooled to −75° C., of 2-benzhydryloxycarbonyl-7-t-butoxycarbonylamino-3-(2-dimethylamino-vinyl)-8-oxo-5-thia-1-azabicyclo[4.2.0]oct-2-ene, E-form, (107.1 g) in dry tetrahydrofuran (600 cc). The mixture is stirred at this temperature for 10 minutes and pyrid-3-yl-thiourea (30.64 g) dissolved in a mixture (400 cc) of water and tetrahydrofuran (50:50 by volume) is then added. The cooling bath is removed and the mixture is stirred at 20° C. for 17 hours. The brown solution is diluted with ethyl acetate (1.5 liters) and is then washed successively with distilled water (1 liter), a half-saturated sodium bicarbonate solution (1 liter), distilled water (1 liter) and a saturated sodium chloride solution (500 cc). The organic phase is dried over anhydrous magnesium sulphate. After evaporation of the solvent under reduced pressure (30 mm Hg; 4 kPa) at 30° C., the residue is chromatographed on a column (height: 46 cm, diameter: 8.1 cm) of silica gel (0.06–0.20 mm), elution being carried out successively with a mixture (5 liters) of cyclohexane and ethyl acetate (50:50 by volume), a mixture (5 liters) of cyclohexane and ethyl acetate (25:75 by volume) and ethyl acetate (7 liters), 1 liter fractions being collected. Fractions 8 to 17, containing the pure product, are combined and concentrated to a residual volume of 250 cc. A yellow suspension is obtained, which is kept at 5° C. for 12 hours. The solid is filtered off, washed with ethyl ether (3×100 cc) and dried under reduced pressure (1 mm Hg; 0.13 kPa). 2-Benzhydryloxycarbonyl-7-t-butoxycarbonylamino-3-[2-(pyrid-3-yl-amino)-thiazol-5-yl]-8-oxo-5-thia-1-azabicyclo[4.2.0]oct-2-ene (14.5 g) is thus obtained in the form of a yellow powder.

Infra-red spectrum (KBr): characteristic bands (cm$^{-1}$) at 3330, 3100, 2500, 1790, 1720, 1590, 1530, 1500, 1370, 1160, 760, 745 and 705.

Proton nuclear magnetic resonance spectrum (250 MHz, d$_6$-DMSO, δ in ppm, J in Hz): 1.45 (s, 9H, —C(CH$_3$)$_3$); 3.76 and 3.88 (2d, J=18, 2H, —S—CH$_2$—); 5.18 (d, J=5, 1H, —H in the 6-position); 5.59 (dd, J=9 and 5, 1H, —H in the 7-position); 6.88 (s, 1H, —COO—CH(C$_6$H$_5$)$_2$); 7 to 7.4 (m, 11H, aromatic protons and —H of the thiazole); 7.34 (m, 1H, —H in the 5-position of the pyridine); 8.07 (ddd, J=8–2.5 and 1, 1H, —H in the 4-position of the pyridine); 8.11 (d, J=9, 1H, —CONH—); 8.19 (dd, J=5 and 1, 1H, —H in the 6-position of the pyridine); 8.69 (d, J=2, 1H, —H in the 2-position of the pyridine); 10.45 (s, 1H, =N—H).

EXAMPLE 28

A mixture of phenacyl bromide (1.19 g) and 2-benzhydryloxycarbonyl-8-oxo-3-[2-(pyrid-3-yl-amino)-thiazol-5-yl]-7-(thien-2-yl-acetamido)-5-thia-1-azabicyclo[4.2.0]oct-2-ene (1.99 g) in N,N-dimethylformamide (10 cc) is stirred for 24 hours at 20° C. The mixture is diluted with ethyl ether (200 cc). The suspension obtained is stirred at 20° C. for 30 minutes and is then filtered, and the product is washed with ethyl ether (20 cc) and dried under reduced pressure (0.1 mm Hg; 0.013 kPa). 2-Benzhydryloxycarbonyl-8-oxo-3-[2-(1-phenacyl-3-pyridinio)-amino-thiazol-5-yl]-7-(thien-2-yl-acetamido)-5-thia-1-azabicyclo[4.2.0]oct-2-ene bromide (2.3 g) is thus obtained in the form of a yellow powder.

Infra-red spectrum (KBr): characteristic bands (cm$^{-1}$) at 3200, 3120, 2500, 1780, 1725, 1695, 1665, 1600, 1570, 1530, 1505, 1450, 1230, 760, 700, 690 and 665.

Proton nuclear magnetic resonance spectrum (250 MHz, d$_6$-DMSO, δ in ppm, J in Hz):

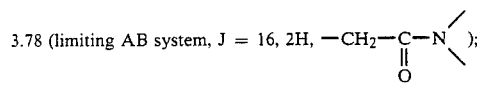

3.78 (limiting AB system, J = 16, 2H, —CH$_2$—C—N );

3.80 and 3.93 (2d, J=18, 2H, —S—CH$_2$—); 5.22 (d, J=5, 1H, —H in the 6-position); 5.82 (dd, J=8 and 5, 1H, —H in the 7-position); 6.58 (limiting AB system, J=18, 2H, ≧$_+$N—CH$_2$—CO—); 6.89 (s, 1H, —COO—CH(C$_6$H$_5$)$_2$); 6.95 to 7.05 (m, —H in the 3-position and —H in the 4-position of the thiophene); 6.95 to 7.35 (m, aromatic protons); 7.23 (s, 1H, —H of the thiazole); 7.37 (dd, J=5 and 1, 1H, —H in the 5-position of the thiophene); 7.68 (t, J=7.5, 2H, aromatic —H in the meta-positions of the phenacyl); 7.82 (t, J=7.5, 1H, aromatic —H in the para-position of the phenacyl); 8.11 (d, J=7.5, 2H, aromatic —H in the ortho-positions of the phenacyl); 8.18 (dd, J=8 and 5, 1H, —H in the 5-position of the pyridine); 8.56 (d broad, J=8, 1H, —H in the 4-position of the pyridine); 8.62 (d, J=5, 1H, —H in the 6-position of the pyridine);

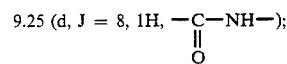

9.25 (d, J = 8, 1H, —C—NH—);

9.31 (s broad, 1H, —H in the 2-position of the pyridine).

Trifluoroacetic acid (26 cc) is added to a solution, cooled to 3° C., of 2-benzhydryloxycarbonyl-8-oxo-3-[2-(1-phenacyl)-3-pyridinio)-amino-thiazol-5-yl]-7-(thien-2-yl-acetamido)-5-thia-1-azabicyclo[4.2.0]oct-2-ene bromide (2.3 g) in anisole (2.6 cc). The mixture is stirred for 15 minutes at 3° C. and then for 30 minutes at 22° C. It is concentrated to dryness under reduced pressure (0.1 mm Hg; 0.013 kPa) at 20° C., and the residue is taken up in ethyl acetate (20 cc) and is then again concentrated to dryness under reduced pressure (0.1 mm Hg; 0.013 kPa) at 20° C. This operation is repeated twice, replacing the ethyl acetate by ethanol. The product is then diluted with ethyl ether (20 cc) and the yellow solid is filtered off, washed with ethyl ether (20 cc) and dried under reduced pressure (0.1 mm Hg; 0.013 kPa) to give 2-carboxy-8-oxo-3-[2-(1-phenacyl-3-pyridinio)-amino-thiazol-5-yl]-7-(thien-2-yl-acetamido)-5-thia-1-azabicyclo[4.2.0]oct-2-ene bromide (1.9 g) in the form of a yellow powder.

Infra-red spectrum (KBr): characteristic bands (cm$^{-1}$) at 3280, 3120, 2100, 1775, 1700, 1670, 1600, 1575, 1500, 1510, 705, 690 and 665.

Proton nuclear magnetic resonance spectrum (350 MHz, d$_6$-DMSO, δ in ppm, J in Hz):

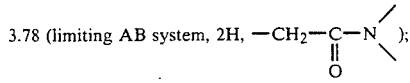

3.78 (limiting AB system, 2H, —CH$_2$—C—N );

3.81 and 3.93 (2d, J=18, 2H, —S—CH$_2$—); 5.18 (d, J=5, 1H, —H in the 6-position); 5.73 (dd, J=8 and 5, 1H, —H in the 7-position); 6.53 (s broad, 2H, ≧$_+$N—CH$_2$—); 6.93 to 7 (m, 2H, —H in the 3-position and —H in the 4-position of the thiophene); 7.35 (dd, J=5 and 1.5, 1H, —H in the 5-position of the thiophene); 7.46 (s, 1H, —H of the thiazole); 7.67 (t, J=8, 2H, aromatic —H in the meta-positions of the phenacyl); 7.79 (t, J=8, 2H, aromatic —H in the para-position of the phenacyl); 8.06 (d, J=8, 2H, aromatic —H in the ortho-positions of the phenacyl); 8.15 (dd, J=8.5 and 6, 1H, —H in the 5-position of the pyridine); 8.6 to 8.7 (m, 2H, —H in the 4-position and —H in the 6-position of the pyridine);

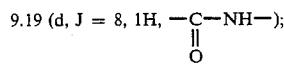

9.19 (d, J = 8, 1H, —C—NH—);

9.45 (s, 1H, —H in the 2-position of the pyridine); 11.62 (b, 1H, >N—H).

EXAMPLE 29

A solution of 2-benzhydryloxycarbonyl-8-oxo-3-[2-(pyrid-3-yl-amino)-thiazol-5-yl]-7-(thien-2-yl-acetamido)-5-thia-1-azabicyclo[4.2.0]oct-2-ene bromide (1.99 g) and t-butyl bromoacetate (0.879 cc) in N,N-dimethylformamide (10 cc) is stirred at 22° C. for 24 hours. The reaction mixture is diluted with ethyl ether (100 cc). The liquid phase is decanted and the residue is taken up in ethyl ether (100 cc). The mixture is stirred for 15 minutes at 20° C. and the solid phase is then filtered off. The precipitate is washed with ethyl ether (2×20 cc) and then dried under reduced pressure (0.1 mm Hg; 0.013 kPa) at 20° C. 2-Benzhydryloxycarbonyl-3-[2-(1-t-butoxycarbonylmethyl-3-pyridinio)-amino-thiazol-5-yl]-8-oxo-7-(thien-2-yl-acetamido)-5-thia-1-azabicyclo[4.2.0]oct-2-ene bromide (2.3 g) is thus obtained in the form of a yellow powder.

Infra-red spectrum (KBr): characteristic bands (cm$^{-1}$) at 3200, 3100, 2500, 1780, 1740, 1670, 1600, 1570, 1520, 1505, 1455, 1370, 1240, 1180, 750, 705 and 670.

Proton nuclear magnetic resonance spectrum (350 MHz,d$_6$-DMSO, δ in ppm, J in Hz): 1.5 (s, 9H, —C(CH$_3$)$_3$); 3.77 and 3.83

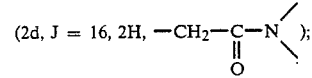

(2d, J = 16, 2H, —CH$_2$—C—N );

3.81 and 3.93 (2d, J=19, 2H, —S—CH$_2$—); 5.24 (d, J=5, 1H, in the 6-position); 5.62 and 5.69 (limiting AB system, J=16, 2H, ≧$_+$N—CH$_2$—); 5.81 (dd, J=8.5 and 5, 1H, —H in the 7-position); 6.89 (s, 1H, —COO—CH(C$_6$H$_5$)$_2$); 6.90 to 7 (m, —H in the 3-position and —H in the 4-position of the thiophene); 6.90 to 7.35 (m, aromatic protons); 7.28 (s, —H of the thiazole); 7.37 (dd, J=5 and 1, —H in the 5-position of the thiophene); 8.15 (dd, J=8.5 and 6, 1H, —H in the 5-position of the pyridine); 8.56 (dd, J=8.5 and 1.5, 1H, —H in the 4-position of the pyridine); 8.67 (d, J=6, 1H, —H in the 6-position of the pyridine);

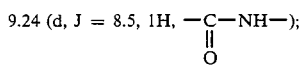

9.28 (s broad, 1H, —H in the 2-position of the pyridine).

Trifluoroacetic acid (29 cc) is added to a solution, cooled to 3° C., of 2-benzhydryloxycarbonyl-3-[2-(1-t-butoxycarbonylmethyl-3-pyridinio)-amino-thiazol-5-yl]-8-oxo-7-(thien-2-yl-acetamido)-5-thia-1-azabicyclo[4.2.0]oct-2-ene bromide (2.3 g) in anisole (2.3 cc). The mixture is stirred at 4° C. for 30 minutes and at 20° C. for 60 minutes. It is concentrated to dryness under reduced pressure (0.1 mm Hg; 0.013 kPa) at 30° C., the residue is taken up in ethyl acetate (50 cc) and the solution obtained is then again concentrated to dryness under reduced pressure (0.1 mm Hg; 0.013 kPa). The operation is repeated and the yellow solid obtained is washed with ethyl ether (50 cc) and then dried under reduced pressure (0.1 mm Hg; 0.013 kPa) at 20° C. 2-Carboxy-3-[2-(1-carboxymethyl-3-pyridinio)-amino-thiazol-5-yl]-8-oxo-7-(thien-2-yl-acetamido)-5-thia-1-azabicyclo[4.2.0]oct-2-ene trifluoroacetate (1.3 g) is obtained in the form of a yellow powder.

Infra-red spectrum (KBr): characteristic bands (cm$^{-1}$) at 3260, 3220, 3150, 2150, 1775, 1740, 1670, 1600, 1530, 1512, 1185, 1145, 800 and 709.

Proton nuclear magnetic resonance spectrum (250 MHz, d$_6$-DMSO, δ in ppm, J in Hz):

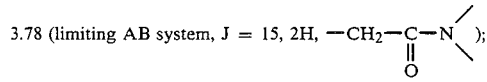

3.81 and 3.95 (2d, J=18, 2H, —S—CH$_2$—); 5.18 (d, J=5, 1H, —H in the 6-position); 5.53 (s broad, 2H, ≧$_+$N—CH$_2$—); 5.72 (dd, J=8 and 5, 1H, —H in the 7-position); 6.9 to 7 (m, 2H, —H in the 3-position and —H in the 4-position of the thiophene); 7.37 (dd, J=5 and 1, 1H, —H in the 5-position of the thiophene); 7.50 (s, 1H, —H of the thiazole); 8.07 (dd, J=8 and 5.5, 1H, —H in the 5-position of the pyridine); 8.50 to 8.65 (m, 2H, —H in the 4-position and —H in the 6-position of the pyridine);

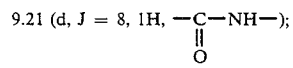

9.4 (s broad, 1H, —H in the 2-position of the pyridine); 11.77 (b, 1H, >NH).

EXAMPLE 30

A solution of 2-benzhydryloxycarbonyl-7-(3,4-dichlorophenylthio)-acetamido-3-(2-nicotinoylamino-thiazol-5-yl)-8-oxo-5-thia-1-azabicyclo[4.2.0]oct-2-ene (0.79 g) and methyl iodide (0.16 g) in N,N-dimethylformamide (3 cc) is stirred for 17 hours at 25° C. and then poured into ethyl ether (100 cc). The solid is filtered off and washed with ethyl ether (3×20 cc), giving, after drying, 2-benzhydryloxycarbonyl-7-(3,4-dichlorophenylthio)-acetamido-3-[2-(methyl-3-pyridinio)-carbonylamino-thiazol-5-yl]-8-oxo-5-thia-1-azabicyclo[4.2.0]oct-2-ene iodide (0.71 g) in the form of a yellow solid.

Infra-red spectrum (KBr): characteristic bands (cm$^{-1}$) at 3200, 3100–2500, 1785, 1725, 1660, 1550, 1500, 810, 750 and 700.

A solution of 2-benzhydryloxycarbonyl-7-(3,4-dichlorophenylthio)-acetamido-3-[2-(methyl-3-pyridinio)-carbonylamino-thiazol-5-yl]-8-oxo-5-thia-1-azabicyclo[4.2.0]oct-2-ene iodide (0.71 g) in formic acid (20 cc) is heated at 50° C. for 30 minutes and then concentrated to dryness under reduced pressure, and the residue is treated in accordance with the working method described in Example 24, to give 2-carboxylato-7-(3,4-dichlorophenylthio)-acetamido-3-[2-(methyl-3 pyridinio)-carbonylamino-thiazol-5-yl]-8-oxo-5-thia-1-azabicyclo[4.2.0]oct-2-ene (0.28 g) in the form of a yellow solid.

Proton nuclear magnetic resonance spectrum (250 MHz, d$_6$-DMSO, δ in ppm, J in Hz): 3.76 and 3.92 (2d, J=18, 2H, —S—CH$_2$—); 3.81 and 3.89 (2d, J=15, 2H, —CH$_2$—CO—N<); 4.43 (s, 3H, ≧$_+$N—CH$_3$); 5.15 (d, J=5, 1H, —H in the 6-position); 5.71 (dd, J=9 and 5, 1H, —H in the 7-position); 7.35 (dd, J=8.5 and 2, 1H, aromatic —H in the 6-position). 7.56 (d, J=8.5, 1H, aromatic —H in the 5-position); 7.63 (s, 1H, —H of the thiazole); 7.64 (d, J=2, 1H, aromatic —H in the 2-position); 8.21 (dd, J=7.5 and 5.5, 1H, —H in the 5-position of the pyridine); 9.04 (d, J=7.5, 1H, —H in the 4-position of the pyridine); 9.07 (d, J=5.5, 1H, —H in the 6-position of the pyridine);

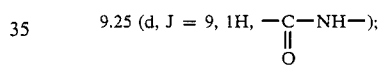

9.53 (s broad, 1H, —H in the 2-position of the pyridine).

2-Benzhydryloxycarbonyl-7-(3,4-dichlorophenylthio)-acetamido-3-(2-nicotinoylamino-thiazol-5-yl)-8-oxo-5-thia-1-azabicyclo[4.2.0]oct-2-ene can be obtained in the following manner:

A solution of 3,4-dichlorophenylthioacetyl chloride (prepared by the action of oxalyl chloride (8.4 cc) on the corresponding acid (3.99 g) in ethyl ether (48 cc), and replacement of the solvent) in ethyl acetate (20 cc) is added, in 10 minutes, to a solution of 7-amino-2-benzhydryloxycarbonyl-3-(2-nicotinoylamino-thiazol-5-yl)-8-oxo-5-thia-1-azabicyclo[4.2.0]oct-2-ene (6.43 g) in N,N-dimethylacetamide (25 cc) at 0° C. After 1 hour at 0° C. followed by 40 minutes at a temperature of between 0° and 20° C., the reaction mixture is poured into ethyl acetate (250 cc) and this mixture is washed with distilled water (3×100 cc) and then with a saturated sodium chloride solution (100 cc). The organic phase is dried and concentrated to dryness under reduced pressure (30 mm Hg; 4 kPa) at 40° C. The residue is filtered on a column of silica (0.02–0.5 mm) (40 g), elution being carried out with a mixture (2 liters) of methylene chloride and methanol (95:5 by volume). The residue obtained after concentrating to dryness under reduced pressure (30 mm Hg; 4 kPa) at 30° C. is crystallised from methylene chloride (20 cc) to give 2-benzhydryloxycarbonyl-7-(3,4-dichlorophenylthio)-acetamido-3-(2-nicotinoylamino-thiazol-5-yl)-8-oxo-5-thia-1-azabicyclo[4.2.0]oct-2-ene (2.9 g) in the form of a pale yellow crystalline solid.

Rf=0.2 (silica gel chromatographic plate, ethyl acetate eluant).

7-Amino-2-benzhydryloxycarbonyl-3-(2-nicotinoylamino-thiazol-5-yl)-8-oxo-5-thia-1-azabicyclo[4.2.0]oct-2-ene can be prepared in the following manner:

2-Benzhydryloxycarbonyl-7-t-butoxycarbonylamino-3-(2-nicotinoylamino-thiazol-5-yl)-8-oxo-5-thia-1-azabicyclo[4.2.0]oct-2-ene (9 g) in acetonitrile (134 cc) is treated with p-toluenesulphonic acid (7.6 g) according to the working method described in Example 24, to give 7-amino-2-benzhydryloxycarbonyl-3-(2-nicotinoylamino-thiazol-5-yl)-8-oxo-5-thia-1-azabicyclo[4.2.0]oct-2-ene (6.43 g) in the form of a cream powder.

Rf=0.23 (silica gel chromatographic plate, ethyl acetate eluant).

2-Benzhydryloxycarbonyl-2-t-butoxycarbonylamino-3-(2-nicotinoylamino-thiazol-5-yl)-8-oxo-5-thia-1-azabicyclo[4.2.0]oct-2-ene can be prepared in the following manner:

Nicotinoyl chloride hydrochloride (7.12 g) is added to a solution of 3-(2-amino-thiazol-5-yl)-2-benzhydryloxycarbonyl-2-t-butoxycarbonylamino-8-oxo-5-thia-1-azabicyclo[4.2.0]oct-2-ene (11.3 g) in tetrahydrofuran (300 cc) cooled to 3° C., and triethylamine (11.12 cc) is then added in 10 minutes. The reaction mixture is stirred for 1 hour at 3° C. and then for 2 hours whilst allowing the temperature to rise to 20° C. It is then poured into ethyl acetate (400 cc) and washed with distilled water (3×120 cc) and a saturated sodium chloride solution (100 cc). The organic phase is dried and concentrated to dryness under reduced pressure (30 mm Hg; 4 kPa) at 40° C. The residue is crystallised from ethyl acetate (20 cc) to give 2-benzhydryloxycarbonyl-2-t-butoxycarbonylamino-3-(2-nicotinoylamino-thiazol-5-yl)-8-oxo-5-thia-1-azabicyclo[4.2.0]oct-2-ene (7.4 g) in the form of a yellow solid.

Rf=0.24 (silica gel chromatographic plate, eluant: a mixture of cyclohexane and ethyl acetate (20:80 by volume)).

The present invention also relates to the pharmaceutical compositions which contain, as the active product, at least one product of the general formula (I) in the free form or in the form of a salt, in association with one or more pharmaceutically acceptable diluents or adjuvants. The compositions can be employed orally, parenterally or topically.

Tablets, pills, powders or granules can be used as solid compositions for oral administration. In these compositions, the active product according to the invention is mixed with one or more inert diluents or adjuvants, such as sucrose, lactose or starch. These compositions can also contain substances other than the diluents, for example a lubricant such as magnesium stearate.

As liquid compositions for oral administration it is possible to use pharmaceutically acceptable emulsions, solutions, suspensions, syrups and elixirs containing inert diluents such as water or liquid paraffin. These compositions can also contain substances other than the diluents, for example wetting agents, sweeteners or flavourings.

The compositions for parenteral administration can be sterile aqueous or non-aqueous solutions, suspensions or emulsions. As the solvent or vehicle it is possible to use propylene glycol, a polyethylene glycol, vegetable oil, in particular olive oil, and injectable organic esters, for example ethyl oleate. These compositions can also contain adjuvants, in particular wetting agents, emulsifiers or dispersing agents. Sterilisation can be effected in various ways, for example with the aid of a asepticizing filter, by incorporating sterilising agents into the composition, by irradiation or by heating. The compositions can also be prepared in the form of sterile solid compositions which are dissolved, at the time of use, in sterile water or any other injectable sterile medium.

The compositions for topical administration can be creams, ointments, lotions, suspensions or solutions, in which the active product can be combined with thickeners, agents which assist penetration, colorants and other conventional ingredients.

In human therapy, the medicaments according to the present invention are particularly useful in the treatment of infections of bacterial origin.

In general, the physician will decide the posology which he considers to be the most appropriate, as a function of the age, weight, degree of infection and other factors specific to the subject to be treated. In general, the doses are between 2 and 8 g of active product per day, administered intramuscularly or intravenously, for an adult.

The examples which follow and are given without implying a limitation, illustrate a composition according to the present invention.

EXAMPLE A

An injectable solution having the following composition is prepared:

| | |
|---|---|
| sodium salt of 2-carboxy-8-oxo-3-(2-phenyl-thiazole-5-yl)-7-(thien-2-yl-acetamido)-5-thia-1-azabicyclo[4.2.0]oct-2-ene | 261 mg |
| sodium chloride | 1.5 mg |
| injectable solvent | 2 cc |

This solution contains 250 mg of active product (calculated as free acid).

EXAMPLE B

An injectable solution having the following composition is prepared:

| | |
|---|---|
| sodium salt of 3-(2-acetamido-thiazol-5-yl)-2-carboxy-8-oxo-7-phenylacetamido-5-thia-1-azabicyclo[4.2.0]oct-2-ene | 262 mg |
| sodium chloride | 1.5 mg |
| injectable solvent | 2 cc |

This solution contains 250 mg of active product (calculated as free acid).

EXAMPLE C

An aqueous isotonic solution (100 cc) containing sodium bicarbonate (2.47 g) and, as the active product, 3-[(L-2-amino-2-carboxy-ethylthioacetamido)-thiazol-5-yl]-2-carboxy-7-(3,4-dichlorophenylthio)-acetamido-8-oxo-5-thia-1-azabicyclo[4.2.0]oct-2-ene (10 g) is prepared. After filtration on a bacteriological filter, this solution is divided aseptically between ampoules (at the rate of 10 cc per ampoule), the solution is lyophilized and the ampoules are sealed.

Each ampoule contains the equivalent of 1 g of active product in the form of its sodium salt.

We claim:

1. A cephalosporin of the formula:

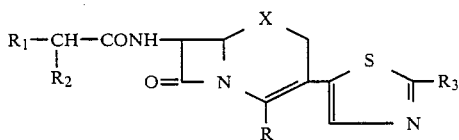

in which $R_1$ represents a radical selected from thienyl, furyl, 1,3-dithiol-2-on-4-yl, phenyl, p-hydroxyphenyl, phenoxy or dichlorophenylthio, and $R_2$ represents a hydrogen atom; or $R_1$ represents phenyl or p-hydroxyphenyl and $R_2$ represents amino; $R_3$ represents hydrogen, phenyl, alkanoylaminophenyl, alkylthio, alkylamino, dialkylamino or anilino, or $R_3$ represents alkanoylamino, benzoylamino, thenoylamino, N-alkyl-alkanoylamino, N-alkyl-benzoylamino, N-alkyl-thenoylamino, N-phenyl-alkanoylamino, N-phenyl-benzoylamino, N-phenyl-thenoylamino, alkoxycarbonylamino, dialkylaminoethylamino, dialkylaminomethyleneamino, alkylidenehydrazo, amino-acetamido, 2-aminoethylthio-acetamido or L-2-amino-2-carboxy-ethylthioacetamido, or $R_3$ represents a radical of the formula —A—$R'_3$, in which A represents —$CH_2$—, —NH— or —NHCO— amd $R'_3$ represents 1-methyl-3-pyridinio, 1-methyl-4-pyridinio, 1-benzoyl-methyl-3-pyridinio, 1-benzoylmethyl-4-pyridinio, 1-carboxymethyl-3-pyridinio or 1-carboxymethyl-4-pyridinio; R represents a carboxyl radical or a carboxylato radical if $R'_3$ is a said substituted pyridinio radical; and X represents sulphur or oxygen, it being understood that the alkyl and alkanoyl radicals and moieties mentioned above are straight or branched and contain 1 to 4 carbon atoms each, in its D,L and D, L forms if $R_2$ is other than a hydrogen atom, and its pharmaceutically acceptable non-toxic metal salts, addition salts with non-toxic nitrogen-containing bases and, where they exist, addition salts with non-toxic acids.

2. A cephalosporin according to claim 1, wherein X represents oxygen and $R_1$, $R_2$, $R_3$ and R are defined as in claim 1, or X represents sulphur, R is defined as in claim 1, and either $R_1$ and $R_2$ are defined as in claim 1 and $R_3$ represents phenyl, alkanoylaminophenyl, alkylthio, anilino, benzoylamino, thenoylamino, N-alkyl-benzoylamino, N-alkyl-thenoylamino, N-phenyl-benzoylamino, N-phenyl-thenoylamino, N-alkyl-alkanoylamino, N-phenyl-alkanoylamino, alkoxycarbonylamino, dialkylamino-ethylamino, dialkylaminomethyleneamino, alkylidenehydrazo, amino-acetamido, 2-amino-ethylthio-acetamido or L-2-amino-2-carboxy-ethylthio-acetamido or $R_3$ represents a radical of the formula —A—$R'_3$, in which A represents —$CH_2$—, —NH— or —NHCO— and $R'_3$ represents 1-methyl-3-pyridinio, 1-methyl-4-pyridinio, 1-benzoyl-methyl-3-pyridinio, 1-benzoylmethyl-4-pyridinio, 1-carboxymethyl-3-pyridinio, or 1-carboxymethyl-4-pyridinio; or $R_1$ is 1,3-dithiol-2-on-4-yl, $R_2$ is a hydrogen atom and $R_3$ is hydrogen, alkylamino, dialkylamino or alkanoylamino, in its D, L and D,L forms if $R_2$ is other than a hydrogen atom, and its pharmaceutically acceptable non-toxic metal salts, addition salts with non-toxic nitrogen-containing bases, and, where they exist, addition salts with non-toxic acids.

3. A cephalosporin according to claim 1, wherein X is sulphur, R is carboxyl, $R_3$ is hydrogen, alkylamino, dialkylamino or alkanoylamino, $R_1$ represents thienyl, furyl, phenyl, p-hydroxyphenyl, phenoxy or 3,4-dichlorophenylthio and $R_2$ represents a hydrogen atom, or $R_1$ reprsents phenyl or p-hydroxyphenyl and $R_2$ represents an amino radical, in its D, L and D,L forms if $R_2$ is other than a hydrogen atom, and its pharmaceutically acceptable non-toxic metal salts, addition salts with non-toxic nitrogen-containing bases and, where they exist, addition salts with non-toxic acids.

4. A cephalosporin according to claim 1, wherein X and R are as defined in claim 1, $R_1$ is thienyl and $R_2$ is hydrogen, or $R_1$ is phenyl or p-hydroxyphenyl and $R_2$ is amino and $R_3$ is hydrogen, phenyl, alkanoylamino, N-alkyl-alkanoylamino, N-dialkylaminoethylamino-alkanoylamino, N-(2-amino-ethylthioacetamido)alkanoylamino, or N-(L-2-amino-2-carboxy-ethylthioacetamido)alkanoylamino, or $R_3$ is a radical of the formula —A—$R'_3$, in which A and $R'_3$ are as defined in claim 1, in its D, L and D,L forms if $R_2$ is amino, and its pharmaceutically acceptable non-toxic meal salts, addition salts with non-toxic nitrogen-containing bases and, where they exist, addition salts with non-toxic acids.

5. A cephalosporin according to claim 1 which is 2-carboxy-8-oxo-3-(2-phenyl-thiazol-5-yl)-7-(thien-2-yl-acetamido)-5-thia-1-azabicyclo[4.2.0]oct-2-ene and its pharmaceutically acceptable non-toxic metal salts and addition salts with non-toxic nitrogen-containing bases.

6. A cephalosporin according to claim 1 which is 3-(2-acetamido-thiazol-5-yl)-2-carboxy-8-oxo-7-phenylacetamido-5-thia-1-aza-bicyclo[4.2.0]oct-2-ene and its pharmaceutically acceptable non-toxic metal salts and addition salts with non-toxic nitrogen-containing bases.

7. A cephalosporin according to claim 1, which is 3-[(L-2-amino-2-carboxy-ethylthioacetamido)thiazol-5-yl]-2-carboxy-7-(3,4-dichlorophenylthio)-acetamido-8-oxo-5-thia-1-aza-bicyclo[4.2.0]oct-2-ene and its pharmaceutically acceptable non-toxic metal salts and addition salts with non-toxic nitrogen-containing bases and addition salts with non-toxic acids.

8. An anti-bacterial pharmaceutical composition comprising an effective amount of at least one cephalosporin according to claim 1, in association with one or more compatible, pharmaceutically acceptable diluents or adjuvants.

9. Method of controlling gram-positive bacteria which comprises exposing said bacteria to the action of a cephalosporin as claimed in claim 1.

* * * * *